US008518989B2

(12) United States Patent
Ganapathy et al.

(10) Patent No.: US 8,518,989 B2
(45) Date of Patent: Aug. 27, 2013

(54) PRODRUGS OF SHORT-CHAIN FATTY ACIDS AND TREATMENT METHODS

(75) Inventors: Vadivel Ganapathy, Martinez, GA (US); Puttur D. Prasad, Martinez, GA (US); Robert G. Martindale, Portland, OR (US)

(73) Assignee: Georgia Health Sciences University Research Institute, Inc., Augusta, GA (US)

( * ) Notice: Subject to any disclaimer, the term of this patent is extended or adjusted under 35 U.S.C. 154(b) by 0 days.

(21) Appl. No.: 13/039,661

(22) Filed: Mar. 3, 2011

(65) Prior Publication Data

US 2011/0245339 A1 Oct. 6, 2011

Related U.S. Application Data

(62) Division of application No. 11/813,343, filed as application No. PCT/US2006/001963 on Jan. 17, 2006, now abandoned.

(60) Provisional application No. 60/644,186, filed on Jan. 14, 2005, provisional application No. 60/683,330, filed on May 20, 2005.

(51) Int. Cl.
*A61K 31/22* (2006.01)
*A61K 31/16* (2006.01)

(52) U.S. Cl.
USPC .......................................... 514/551; 514/629

(58) Field of Classification Search
None
See application file for complete search history.

(56) References Cited

U.S. PATENT DOCUMENTS

| | | | |
|---|---|---|---|
| 5,431,904 A | | 7/1995 | Laney |
| 5,800,804 A | * | 9/1998 | Laney ............................. 424/65 |
| 5,958,886 A | | 9/1999 | Carter et al. |
| 8,003,683 B2 | * | 8/2011 | Chandran ..................... 514/423 |
| 2004/0142317 A1 | | 7/2004 | Ganapathy et al. |
| 2005/0095240 A1 | | 5/2005 | Ganapathy et al. |
| 2005/0137141 A1 | | 6/2005 | Hilfinger |
| 2006/0019241 A1 | | 1/2006 | Ganapathy et al. |
| 2009/0123388 A1 | | 5/2009 | Ganapathy et al. |
| 2010/0137236 A1 | | 6/2010 | Ganapathy et al. |
| 2010/0305184 A1 | | 12/2010 | Ganapathy et al. |

FOREIGN PATENT DOCUMENTS

| | | |
|---|---|---|
| WO | WO 02/083060 A2 | 10/2002 |
| WO | WO 02/083060 A3 | 7/2003 |
| WO | WO 2004/048925 A2 | 6/2004 |
| WO | WO 2004/048925 A3 | 1/2005 |
| WO | WO 2005/114217 A2 | 12/2005 |
| WO | WO 2005/114217 A3 | 6/2006 |
| WO | WO 2006/076734 A2 | 7/2006 |
| WO | WO 2006/076734 A3 | 2/2007 |
| WO | WO 2008/144423 A2 | 11/2008 |
| WO | WO 2008/144423 A3 | 9/2009 |
| WO | WO 2010/042685 A2 | 4/2010 |
| WO | WO 2010/042685 A3 | 8/2010 |

OTHER PUBLICATIONS

Ambs et al., "Frequent nitric oxide synthase-2 expression in human colon adenomas: implication for tumor angiogenesis and colon cancer progression," (1998) *Cancer Res.* 58:334-341.
Ambs et al., "Relationship between p53 mutations and inducible nitric oxide synthase expression in human colorectal cancer," (1999) *J. Natl. Cancer Inst.* 91:86-88.
Augenlicht et al., "Short-chain fatty acid metabolism, apoptosis, and Apc-initiated tumorigenesis in the mouse gastrointestinal mucosa," (1999) *Cancer Res.* 59:6005-6009.
Barbarat and Podevin, "Stoichiometry of the renal sodium-L-lactate cotransporter," (1988) *J. Biol. Chem.* 263:12190-12193.
Barnard and Warwick, "Butyrate rapidly induces growth inhibition and differentiation in HT29 cells," (1993) *Cell Growth Differ.*, 4:495-501.
Basson et al., "Identification and comparative analysis of human colonocyte short-chain fatty acid response genes," (2000) *J. Gastrointest. Surg.* 4:501-512.
Bing et al., "Nitric oxide, prostanoids, cyclooxygenase, and angiogenesis in colon and breast cancer," (2001) *Clin. Cancer Res.* 7:3385-3392.
Blottiere et al., "Molecular analysis of the effect of short-chain fatty acids on intestinal cell proliferation," (2003) *Proc. Nutr. Soc.* 62:101-106.
Bongaerts et al., "Role of bacteria in the pathogenesis of short bowel syndrome-associated D-lactic acidemia," (1997) *Microb. Pathog.* 22:285-293.
Bush et al., "Synthesis of addition polymers derived from enantiomerically pure amino acids," (1998) *Polymer* 39(4):933-941.
Chen et al., "Short-chain fatty acid inhibitors of histone deacetylases: promising anticancer therapeutics?" (2003) *Curr. Cancer Drug Targets* 3:219-236.
Cianchi et al., "Cyclooxygenase-2 activation mediates the proangiogenic effect of nitric oxide in colorectal cancer," (2004) *Clin. Cancer Res.* 10:2694-2704.
Closs et al., "Substrate supply for nitric-oxide synthase in macrophages and endothelial cells: role of cationic amino acid transporters," (2000) *Mol. Pharmacol.* 57:68-74.

(Continued)

*Primary Examiner* — James D Anderson
(74) *Attorney, Agent, or Firm* — Mueting, Raasch & Gebhardt P.A.

(57) ABSTRACT

Prodrugs made up of biologically-active short-chain fatty acids or derivatives thereof conjugated to neutral or cationic amino acids capable of intracellular transport by $ATB^{0,+}$ are provided. The short-chain fatty acid or derivative thereof can be attached to the amino acid through a hydroxyl group of the amino acid to form a fatty acid ester of the amino acid, or it can be attached through the amino group of the amino acid to form a fatty-acid amide of the amino acid. Serine butyrate (O-butyryl serine) is a preferred prodrug. These prodrugs are useful for treatment of colon cancer, inflammatory bowel disease, ulcerative colitis, Crohn's disease, lung cancer, cervical cancer, and cancers resulting from metastases from primary colon cancer sites. Methods of delivering biologically-active short-chain fatty acids or derivatives thereof to cells in need of these molecules and methods of treating diseases using the prodrugs of this invention are also provided.

23 Claims, 32 Drawing Sheets

(56) References Cited

OTHER PUBLICATIONS

Coady et al., "The tumor suppressor gene SLC5A8 expresses a Na+-monocarboxylate cotransporter," (2004) *J. Physiol.* (Lond.) 557:719-731.
Cobbs, et al., "Expression of nitric oxide synthase in human central nervous system tumors" (1995) *Cancer Res.* 55:727-730.
Conley et al., "Phase I study of the orally administered butyrate prodrug, tributyrin, in patients with solid tumors," (1998) *Clin Cancer Res.* 4:629-634.
Cook et al., "Overall mechanism and rate equation for O-acetylserine sulfhydrlase," (1977) *J. Biol. Chem.* 252:3459.
Coradini et al., "Sodium butyrate modulates cell cycle-related proteins in HT29 human colonic adenocarcinoma cells," (2000) *Cell Prolif.* 33(3):139-146.
Crowell et al. "Is inducible nitric oxide synthase a target for chemoprevention?" (2003) *Mol. Cancer Ther.* 2: 815-823.
Davie, "Inhibition of histone deacetylase activity by butyrate," (2003) *J. Nutr.* 133:2485S-2493S.
DeWald et al., "Some new esters of serine with various acids," (1959) *J. Am. Chem. Soc.* 81:4367-4370.
Doi et al., "Excessive production of nitric oxide in rat solid tumor and its implication in rapid tumor growth," (1996) *Cancer* 77:1598-1604.
Drummond et al., "Clinical development of histone deacetylase inhibitors as anticancer agents," (2005) *Annu. Rev. Pharmacol. Toxicol.* 45:495-528. Available online on Sep. 27, 2004.
El-Gayar et al., "Translational control of inducible nitric oxide synthase by IL 13 and arginine availability in inflammatory macrophages," (2003) *J. Immunol.* 171:4561-4568.
Emenaker et al., "Short-chain fatty acids inhibit invasive human colon cancer by modulating uPA, TIMP-1, TIMP-2, mutant p53, Bcl-2, Bax, p21 and PCNA protein expression in an in vitro cell culture model," (2001) *J. Nutr.* 131:3041S-3046S.
Emmanuel et al. "Functional characterization of human receptors for short chain fatty acids and their role in polymorphonuclear cell activation," (2003) *J. Biol. Chem.* 278(28):25481-25489.
Fraga et al., "Loss of acetylation at Lys16 and trimethylation at Lys20 of histone H4 is a common hallmark of human cancer," (2005) *Nat. Genet.* 37:391-400. Available online on Mar. 13, 2005.
Franchi et al., "Inducible nitric oxide synthase expression in laryngeal neoplasia: correlation with angiogenesis," (2002) *Head Neck* 24:16-23.
Ganapathy et al., "Biological functions of SLC5A8, a candidate tumour suppressor," (2005) *Biochem. Soc. Trans.* 33:237-240.
Gatenby and Gillies, "Why do cancers have high aerobic glycolysis?" (2004) *Nat. Rev. Cancer* 4:891-899.
Geschwind et al., "Novel therapy for liver cancer: direct intraarterial injection of a potent inhibitor of ATP production," (2002) *Cancer Res* 62(14):3909-3913.
Giugliano et al., "The vascular effects of L-arginine in humans. The role of endogenous insulin," (1999) *J. Clin. Invest.* 99:433-438.
Giuliano et al., "The apoptotic effects and synergistic interaction of sodium butyrate and MG132 in human retinoblastoma Y79 cells," (1999) *Cancer Res.* 59:5586-5595.
Glass et al., "Comparative biochemical studies of milks. V. The triglyceride composition of milk fats," (1969) *Comp. Biochem. Physiol.* 28:783-786.
Gopal et al. "Expression of slc5a8 in kidney and its role in Na+-coupled transport of lactate," (2004) *J. Biol. Chem.* 279:44522-44532.
Gopal et al. "Sodium-coupled and electrogenic transport of B-complex vitamin nicotinic acid by slc5a8, a member of the Na/glucose co-transporter gene family," (2005) *Biochem. J.* 388:309-316.
Gupta et al., "SLC5A8 (SMCT1)-mediated transport of butyrate forms the basis for the tumor suppressive function of the transporter," (2006) *Life Sci.* 78:2419-2425. Available online on Dec. 20, 2005.
Halestrap and Price, "The proton-linked monocarboxylate transporter (MCT) family: structure, function and regulation," (1999) *Biochem. J.* 343:281-299.

Hatanaka et al., "$Na^+$—and $Cl^-$ -coupled active transport of nitric oxide synthase inhibitors via amino acid transport system $B^{0,+}$," (2001) *J. Clin. Invest.* 107(8): 1035-1043.
Hatanaka et al., "Evidence for the transport of neutral as well as cationic amino acids by ATA3, a novel and liver-specific subtype of amino acid transport system," (2001) *A. Biochim. Biophys. Acta* 1510:10-17.
Hatanaka et al., "Transport of D-serine via the amino acid transporter $ATB^{(o,+)}$ expressed in the colon," (2002) *Biochem. Biophys. Res. Commun.* 291(2):291-295.
Hatanaka et al., "Transport of amino acid-based prod rugs by the $Na^+$—and $Cl^-$ -coupled amino acid transporter ATBo.+ and expression of the transporter in tissues amenable for drug delivery," (2004) *J. Pharmacol. Exp. Ther.* 308:1138-1147.
Hellmuth et al., "Nitric oxide differentially regulates pro- and anti-angiogenic markers in DLD-1 colon carcinoma cells," (2004) *FEBS Lett.* 563:98-102.
Hinnebusch et al., "The effects of short-chain fatty acids on human colon cancer cell phenotype are associated with histone hyperacetylation," (2002) *J. Nutr.* 132:1012-101.
Hong et al., "Shared epigenetic mechanisms in human and mouse gliomas inactivate expression of the growth suppressor SLC5A8," (2005) *Cancer Res.* 65:3617-3623. Publication date of May 1, 2005.
Inoue et al., "Enhanced hepatic amino acid transport in tumor-bearing rats is partially blocked by antibody to tumor necrosis factor," (1995) *Cancer Res.* 55:3525-3530.
Inoue et al., "Functional features and genomic organization of mouse NaCT, a sodium-coupled transporter for tricarboxylic acid cycle intermediates," (2004) *Biochem. J.* 378:949-957.
International Preliminary Report on Patentability issued Jul. 17, 2007, in International Patent Application No. PCT/US2006/001963, filed Jan. 17, 2006.
International Search Report issued Nov. 9, 2006, in International Patent Application No. PCT/US2006/001963, filed Jan. 17, 2006.
Insinga et al., "Inhibitors of histone deacetylases induce tumor-selective apoptosis through activation of the death receptor pathway," (2005) *Nat. Med.* 11:71-76.
Jan et al., "Propionibacteria induce apoptosis of colorectal carcinoma cells via short-chain fatty acids acting on mitochondria," (2002) *Cell Death Differ.* 9:179-188.
Jaiswal et al., "Inflammatory cytokines induce DNA damage and inhibit DNA repair in cholangiocarcinoma cells by a nitric oxide-dependent mechanism," (2000) *Cancer Res.* 60:184-190.
Jemal et al., "Cancer statistics, 2004," (2004) *CA Cancer J. Clin.* 54:8-29.
Jenkins et al., "Roles of nitric oxide in tumor growth," (1995) *Proc. Natl. Acad. Sci. USA* 92:4392-4396.
Jozkowicz et al., "Involvement of nitric oxide in angiogenic activities of vascular endothelial growth factor isoforms," (2004) *Growth Factors* 22:19-28.
Kimura et al., "Increased expression of an inducible isoform of nitric oxide synthase and the formation of peroxynitrite in colonic mucosa of patients with active ulcerative colitis," (1998) *Gut* 42:180-187.
Kimura et al., "Orphan G protein-coupled receptor, GPR41, induces apoptosis via a p53/Bax pathway during ischemic hypoxia and reoxygenation," (2001) *J. Biol. Chem.* 276(28):26453-26460.
Kitano et al., "Expression of inducible nitric oxide synthase in human thyroid papillary carcinomas," (1999) *Thyroid* 9:113-117.
Ko et al., "Advanced cancers: eradication in all cases using 3-bromopyruvate therapy to deplete ATP," (2004) *Biochem. Biophys. Res. Commun.* 324(1):269-75.
Kojima et al., "Nitric oxide synthase expression and nitric oxide production in human colon carcinoma tissue," (1999) *J. Surg. Oncol.* 70:222-229.
Kuefner et al., "Carboxypeptidase-mediated release of methotrexate from methotrexate α-peptides," (1989) *Biochemistry* 28:2288-2297.
Kuramoto et al., "Etiology-specific gene expression profiles in rat mammary carcinomas," (2002) *Cancer Res.* 62:3592-3597.
Lagares-Garcia et al., "Nitric oxide synthase as a marker in colorectal carcinoma," (2001) *Am. Surg.* 67:709-713.
Lala, "Significance of nitric oxide in carcinogenesis, tumor progression and cancer therapy," (1998) *Cancer Metastasis Rev.* 17:1-6.

Lee et al., "Translational control of inducible nitric oxide synthase expression by arginine can explain the arginine paradox," (2003) *Proc. Natl. Acad. Sci. USA* 100:4843-4848.

Li et al., "SLC5A8, a sodium transporter, is a tumor suppressor gene silenced by methylation in human colon aberrant crypt foci and cancers," (2003) *Proc. Natl. Acad. Sci. USA* 100(14):8412-8417.

Madesh et al., "Nitric oxide prevents anoxia-induced apoptosis in colonic HT29 cells," (1999) *Arch. Biochem. Biophys.* 366:240-248.

Manning and Gibson, "Microbial-gut interactions in health and disease," (2004) *Prebiotics Best Pract. Res. Clin. Gastroenterol.* 18:287-298.

Marks et al., "Histone deacetylases and cancer: causes and therapies," (2001) *Nat. Rev. Cancer* 1:194-202.

McDonald et al., "A caveolar complex between the cationic amino acid transport 1 and endothelial nitric-oxide synthase may explain the 'arginine paradox'," (1997) *J. Biol. Chem.* 272:31213-31216.

Menchen et al., "N-(3-(aminomethyl)benzyl)acetamidine, an inducible nitric oxide synthase inhibitor, decreases colonic inflammation induced by dinitrobenzene sulphonic acid in rats," (2001) *Life Sci.* 69:479-491.

Micheel et al. "Degradation of serine to pyruvic acid," (1958) *Chemische Berichte*) 91:985-987. See Abstract at Chemical Abstracts. 1960, vol. 54, Abstract No. 1336d-f. Caplus Accession No. 1960-6697.

Miyauchi et al., "Functional identification of SLC5A8, a tumor suppressor down-regulated in colon cancer, as a Na+-coupled transporter for short-chain fatty acids," (2004) *J. Biol. Chem.* 279:13293-13296.

Murata et al., "Nitric oxide as a carcinogen: analysis by yeast functional assay of inactivating p53 mutations induced by nitric oxide," (1997) *Mutat. Res.* 379:211-218.

Nakata et al., "Histone deacetylase inhibitors upregulate death receptor 5/TRAIL-R2 and sensitize apoptosis induced by TRAIL/AP02-L in human malignant tumor cells," (2004) *Oncogene* 23:6261-6271.

Nakanishi et al., "$Na^+$—and $Cl^-$ -coupled active transport of carnitine by the amino acid transporter $ATB^{0,+}$ from mouse colon expressed in HRPE cells and *Xenopus* oocytes," (2001) *J. Physiol.* 532:297-304.

Nakano et al., "Butyrate activates the WAF1/Cip1 gene promoter through Sp1 sites in a p53-negative human colon cancer cell line," (1997) *J. Biol. Chem.* 272(35):22199-22206.

Nebbioso et al., "Tumor-selective action of HDAC inhibitors involves TRAIL induction in acute myeloid leukemia cells," (2005) *Nat. Med.* 11:77-84.

Nelson, "3-Bromopyruvate kills cancer cells in animals," (2002) *Lancet. Oncol.* 3(9):524.

Porra et al., "Silencing of the tumor suppressor gene SLC5A8 is associated with BRAF mutations in classical papillary thyroid carcinomas," (2005) *J. Clin. Endocrinol. Metab.* 90:3028-3035. Available online on Feb. 1, 2005.

Porter et al., "Molecular markers in ductal carcinoma in situ of the breast," (2003) *Mol. Cancer Res.* 1:362-375.

Rachmilewitz et al., "Enhanced colonic nitric oxide generation and nitric oxide synthase activity in ulcerative colitis and Chrohn's disease," (1995) *Gut* 36:718-723.

Radisavljevic, "Nitric oxide suppression triggers apoptosis through the FKHRL1 (FOXO3A)/ROCK kinase pathway in human breast carcinoma cells," (2003) *Cancer* 97:1358-1363.

Rajendran and Binder, "Characterization and molecular localization of anion transporters in colonic epithelial cells," (2000) *Ann. N. Y. Acad. Sci.* 915:15-29.

Rao et al., "Chemoprevention of colonic aberrant crypt foci by an inducible nitric oxide synthase-selective inhibitor," (1999) *Carcinogenesis* 20:641-644.

Rao et al., "Chemopreventive properties of a selective inducible nitric oxide synthase inhibitor in colon carcinogenesis, administered alone or in combination with celecoxib, a selective cyclooxygenase-2 inhibitor," (2002) *Cancer Res.* 62:165-170.

Rodriguez et al., "Identification and characterization of a putative human iodide transporter located at the apical membrane of thyrocytes," (2002) *J. Clin. Endocrinol. Metab.* 87:3500-3503.

Scott et al., "Single amino acid (arginine) deprivation: rapid and selective death of cultured transformed and malignant cells," (2000) *Br. J. Cancer* 83:800-810.

Sellin, "SCFAs: the enigma of weak electrolyte transport in the colon," (1999) *News Physiol. Sci.* 14:58-64.

*Sigma Biochemicals and Reagents Catalog.* Sigma-Aldrich Corporation, St.Louis, MO 2000-2001.

Sloan and Mager, "Cloning and functional expression of a human $Na^+$—and $Cl^-$ -dependent neutral and cationic amino acid transporter $B^{0,+}$," (1999) *J. Biol. Chem.* 274: 23740-23745.

Sloan, et al., "Expression of the amino acid transporter AT $B^{0,+}$ in lung: possible role in luminal protein removal," (2003) *Am. J. Physiol.* 284:L39-49.

Sterneck et al., "Selectively enhanced contextual fear conditioning in mice lacking the transcriptional regulator CCAAT/enhancer binding protein delta," (1998) *Proc. Natl. Acad. Sci. USA* 95:10908-10913.

Stubbs et al., "Causes and consequences of tumour acidity and implications for treatment," (2000) *Mol. Med. Today* 6:15-19.

Sugawara et al., "Structure and function of ATA3, a new subtype of amino acid transport system A, primarily expressed in the liver and skeletal muscle," (2000) *Biochim. Biophys. Acta* 1509:7-13.

Takahashi et al., "Increased expression of inducible and endothelial constitutive nitric oxide synthases in rat colon tumors induced by azoxymethane," (1997) *Cancer Res.* 57:1233-1237.

Thangaraju et al., "Comparison of mammary gland involution between 129S1 and C57BL/6 inbred mouse strains: differential regulation of Bcl2al, Trp53, Cebpb, and Cebpd expression," (2004) *Oncogene* 23:2548-2553.

Thangaraju et al., "C/EBPdelta is a crucial regulator of pro-apoptotic gene expression during mammary gland involution," (2005) *Development* 132:4675-4685. Available online on Sep. 28, 2005.

Thomsen et al., "Nitric oxide synthase activity in human gynecological cancer," (1994) *Cancer Res.* 54:1352-1354.

Thomsen et al., "Selective inhibition of inducible nitric oxide synthase inhibits tumor growth in vivo: studies with 1400W, a novel inhibitor," (1997) *Cancer Res.* 57:3300-3304.

Thomsen and Miles, "Role of nitric oxide in tumour progression: lessons from human tumours," (1998) *Cancer Metastasis Rev.* 17:107-118.

Thomsen et al., "Nitric oxide synthase activity in fresh cells from ovarian tumour tissue: relationship of enzyme activity with clinical parameters of patients with ovarian cancer," (1998) *Biochem. Pharmacol.* 56:1365-1370.

Topping and Clifton, "Short-chain fatty acids and human colonic function: roles of resistant starch and nonstarch polysaccharides," (2001) *Physiol. Rev.* 81:1031-1064.

Ueno et al., "Aberrant methylation and histone deacetylation associated with silencing of SLC5A8 in gastric cancer," (2004) *Tumour Biol.* 25:134-140.

Umapathy et al., "Transport of amino acid esters and the amino-acid-based prodrug valganciclovir by the amino acid transporter $ATB^{0,+}$," (2004) *Pharm. Res.* 21:1303-1310.

Uribarri et al., "D-lactic acidosis. A review of clinical presentation, biochemical features, and pathophysiologic mechanisms," (1998) *Medicine* (Baltimore) 77:73-82.

Vigushin and Coombes, "Histone deacetylase inhibitors in cancer treatment, " (2002) *Anti-cancer Drugs* 13:1-13.

Vodovotz et al., "Inactivation of nitric oxide synthase after prolonged incubation of mouse macrophages with IFN-gamma and bacterial lipopolysaccharide," (1994) *J. Immunol.* 152:4110-4118.

Wachtershauser and Stein, "Rationale for the luminal provision of butyrate in intestinal diseases," (2000) *Eur. J. Nutr.* 39:164-171.

Wang et al. "Characteristics of $\beta,\beta$-difluoroalanine and $\beta,\beta,\beta$-trifluorialanine as suicide substrates for *Escherichia coli* B alanine racemase," (1981) *Biochemistry* 20:7539-7546.

Wang et al., "Structure, function, and genomic organization of human Na(+)-dependent high-affinity dicarboxylate transporter," (2000) *Am. J. Physiol. Cell Physiol.* 278:C1019-C103.

Wang and Friedman, "Short-chain fatty acids induce cell cycle inhibitors in colonocytes," (1998) *Gastroenterology* 114:940-94.

Wellman et al., "Nitric oxide and reactive oxygen species exert opposing effects on the stability of hypoxia-inducible factor-1 alpha (HIF-1 alpha) in explants of human pial arteries," (2004) *FASEB J.* 18:379-381.

Wenzel et al., "Nitric oxide suppresses apoptosis in human colon cancer cells by scavenging mitochondrial superoxide anions," (2003) *Int. J. Cancer* 106:666-675.

Wenzel et al., "Nitric oxide levels in human preneoplastic colonocytes determine their susceptibility toward antineoplastic agents," (2003) *Mol. Pharmacol.* 64:1494-1502.

Wright and Turk, "The sodium/glucose cotransport family SLC5," (2004) *Pflügers Arch. Eur. J. Physiol.* 447(5):510-518. Available online on May 14, 2003.

Written Opinion issued Nov. 9, 2006, in International Patent Application No. PCT/US2006/001963, filed Jan. 17, 2006.

Wu et al., "Functional characteristics and tissue distribution pattern of organic cation transporter 2 (OCTN2), an organic cation/carnitine transporter," (1999) *J. Pharm. and Exp. Ther.* 290:1482-1492.

Yagihashi et al., "Increased in situ expression of nitric oxide synthase in human colorectal cancer," (2000) *Virchows Arch.* 436:109-114.

Zhao et al., "Inhibitors of histone deacetylases target the Rb-E2F1 pathway for apoptosis induction through activation of proapoptotic protein Bim," (2005) *Proc. Natl. Acad. Sci. USA* 102:16090-16095.

\* cited by examiner

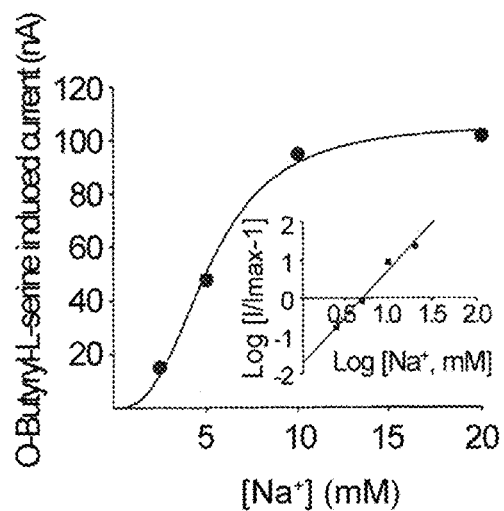
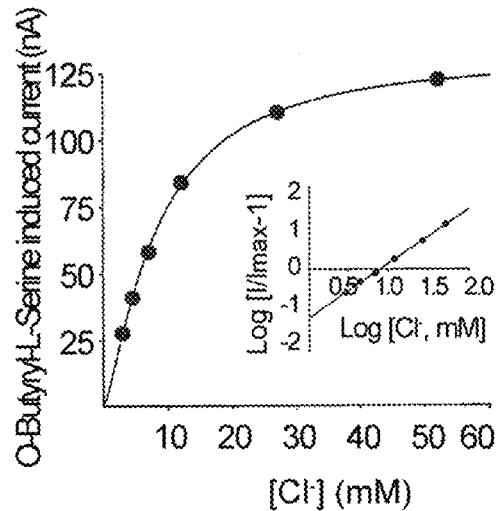
FIG. 12A  FIG. 12B
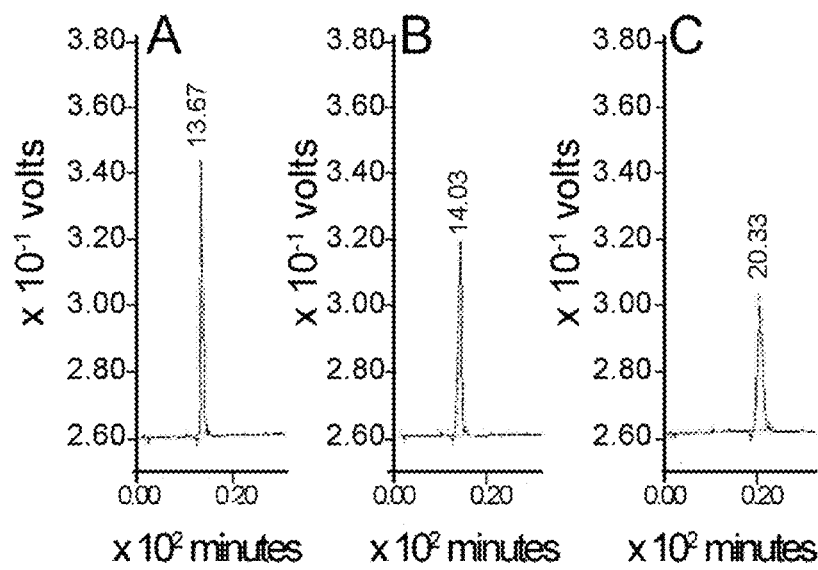
FIG. 13

IP: Histone H4
IB: Acetyl-H4-Lys16

SEQUENCE LISTING

```
<160> NUMBER OF SEQ ID NOS: 16

<210> SEQ ID NO 1
<211> LENGTH: 22
<212> TYPE: DNA
<213> ORGANISM: Homo sapiens

<400> SEQUENCE: 1
gaaggagaaa gtgtcggctt ca                                              22
```

-continued

```
<210> SEQ ID NO 2
<211> LENGTH: 22
<212> TYPE: DNA
<213> ORGANISM: Homo sapiens

<400> SEQUENCE: 2
taccaccttg ccagacgatt tg                                            22

<210> SEQ ID NO 3
<211> LENGTH: 24
<212> TYPE: DNA
<213> ORGANISM: Homo sapiens

<400> SEQUENCE: 3
ctggccaggg tggaagcggt aaca                                          24

<210> SEQ ID NO 4
<211> LENGTH: 24
<212> TYPE: DNA
<213> ORGANISM: Homo sapiens

<400> SEQUENCE: 4
caccaccaac agcagccgtt cctc                                          24

<210> SEQ ID NO 5
<211> LENGTH: 21
<212> TYPE: DNA
<213> ORGANISM: Homo sapiens

<400> SEQUENCE: 5
ccagatagct acatcgggat a                                             21

<210> SEQ ID NO 6
<211> LENGTH: 20
<212> TYPE: DNA
<213> ORGANISM: Homo sapiens

<400> SEQUENCE: 6
caggtagagg gcagggtatt                                               20

<210> SEQ ID NO 7
<211> LENGTH: 31
<212> TYPE: DNA
<213> ORGANISM: Homo sapiens

<400> SEQUENCE: 7
gatatatagc catggacacg ccacggggca t                                  31

<210> SEQ ID NO 8
<211> LENGTH: 30
<212> TYPE: DNA
<213> ORGANISM: Homo sapiens

<400> SEQUENCE: 8
cgcgaagctt cacaaacgag tcccattgct                                    30

<210> SEQ ID NO 9
<211> LENGTH: 26
<212> TYPE: DNA
<213> ORGANISM: Mus musculus

<400> SEQUENCE: 9
```

```
gatatatagc catggacgcg tcgcgg                                               26

<210> SEQ ID NO 10
<211> LENGTH: 26
<212> TYPE: DNA
<213> ORGANISM: Mus musculus

<400> SEQUENCE: 10
aagcttcaca agcgagtccc attgat                                               26

<210> SEQ ID NO 11
<211> LENGTH: 26
<212> TYPE: DNA
<213> ORGANISM: Mus musculus

<400> SEQUENCE: 11
gacgccgcca tgagcgccgc gctttt                                               26

<210> SEQ ID NO 12
<211> LENGTH: 26
<212> TYPE: DNA
<213> ORGANISM: Mus musculus

<400> SEQUENCE: 12
aagcttttac cggcagtcgg cgccgc                                               26

<210> SEQ ID NO 13
<211> LENGTH: 26
<212> TYPE: DNA
<213> ORGANISM: Homo sapiens

<400> SEQUENCE: 13
acgcgtatag ccatggacac gccacc                                               26

<210> SEQ ID NO 14
<211> LENGTH: 26
<212> TYPE: DNA
<213> ORGANISM: Homo sapiens

<400> SEQUENCE: 14
cagctgtcac aaacgagtcc cattgc                                               26

<210> SEQ ID NO 15
<211> LENGTH: 26
<212> TYPE: DNA
<213> ORGANISM: Homo sapiens

<400> SEQUENCE: 15
gacgccgcca tgagcgccgc gctctt                                               26

<210> SEQ ID NO 16
<211> LENGTH: 23
<212> TYPE: DNA
<213> ORGANISM: Homo sapiens

<400> SEQUENCE: 16
aagcttttac cggcagtctg tcc                                                  23
```

PRODRUGS OF SHORT-CHAIN FATTY ACIDS AND TREATMENT METHODS

CROSS-REFERENCE TO RELATED APPLICATIONS

This application is a divisional application of Ser. No. 11/813,343, Confirmation No. 1130, filed on Sep. 21, 2007, which is a submission to enter the national state under 35 U.S.C. 371 for PCT Application No. PCT/US2006/001963, filed on Jan. 17, 2006 and published in English on Jul. 20, 2006 as WO 2006/076734, which claims priority to U.S. Provisional Application No. 60/644,186, filed Jan. 14, 2005, and U.S. Provisional Application No. 60/683,330, filed May 20, 2005, all of which are incorporated herein to the extent that there is no inconsistence with the present disclosure. U.S. patent application Ser. No. 10/467,893, first filed on Apr. 12, 2002 as Patent Cooperation Treaty Application PCT/JP02/03678, and published on Jul. 22, 2004 with Publication No. 2004/0142317 A1, is incorporated by reference herein to the extend not inconsistent herewith.

STATEMENT REGARDING FEDERALLY SPONSORED RESEARCH

This invention was made with government support under Grant Numbers HD44404, HL64196, AI49849 and GM64176, awarded by the National Institutes of Health (NIH). The United States government has certain rights in this invention.

BACKGROUND

Colorectal cancer is the second most common cause of new cancer cases and cancer deaths in the United States, with an estimated 146,940 new cases and 56,730 deaths in 2004 (Jemal, A. et al. (2004), Cancer statistics, 2004, CA *Cancer J. Clin.* 54:8-29).

Butyrate is a short-chain fatty-acid produced in the colon by bacterial fermentation of dietary fiber and required for colonic health. Tributyrin (glyceryl tributyrate) is a prodrug of butyrate that is hydrolyzed to butyrate in the intestine. It has been suggested as a therapeutic to prevent colon cancer (Conley, B. A., et al. (1998), *Clin. Cancer Res.* 4:629-634) and inflammatory bowel disease. Butyrate-producing bacteria have also been used to treat these conditions.

Short-chain fatty acids, including butyrate, are produced at high concentrations in the colonic lumen by bacterial fermentation of dietary fiber (Mortensen, P. B. & Clausen, M. R. "Short-chain fatty acids in the human colon: relation to gastrointestinal health and disease," (1996) *Scand. J. Gastroenterol.* 216, 132-148; Manning, T. S. & Gibson, G. R. "Microbial-gut interactions in health and disease," (2004) *Prebiotics. Best Pract. Res. Clin. Gastroenterol.* 18, 287-298). Of these, acetate is the most abundant, but butyrate plays the most important role in colonic physiology. In the proximal large bowel, butyrate represents the preferred respiratory fuel in the intestine through β-oxidation.

Apart from the function of butyrate as a dominant energy source for colonocytes, it also inhibits cellular proliferation and induces apoptosis by regulating the key proteins controlling the cell cycle (Coradini et al., (2000) *Cell Prolif.* 33(3): 139-146). It induces differentiation in colon epithelial cells, but causes apoptosis in colon cancer cells (Gupta, N., Martin, P. M., Prasad, P. D. & Ganapathy, V. "SLC5A8 (SMCT1)-mediated transport of butyrate forms the basis for the tumor suppressive function of the transporter," *Life Sci.* in press (2005)). The sodium salt of butyrate, sodium butyrate, is known to inhibit cell growth by favoring cell cycle arrest and promotes differentiation in normal as well as transformed cells (Barnard & Warwick, "Butyrate rapidly induces growth inhibition and differentiation in HT29 cells," (1993) *Cell Growth Differ.*, 4:495-501). Moreover, sodium butyrate induces apoptosis in a number of cancer cells (Mandal, M. and Kumar, R., "Bcl-2 expression regulates sodium butyrate-induced apoptosis in human MCF-7 breast cancer cells," (1996) *Cell Death Differ.* 7:311-318; Bernhard, D. et al. "Apoptosis induced by the histone deacetylase inhibitor sodium butyrate in human leukemic lymphoblasts," (1999) *FASEB J.* 13:1991-2001; Giuliano, M. et al., "The apoptotic effects and synergistic interaction of sodium butyrate and MG132 in human retinoblastoma Y79 cells," (1999) *Cancer Res.* 59:5586-5595). Previous studies demonstrated that deficiency in the availability or utilization of butyrate causes colitis and may be involved in colon carcinogenesis (Soergel, K. H., (1994) *Clin. Invest.* 72:742-748).

Due to its growth-inhibiting and differentiation-inducing ability, butyrate was tested in the treatment of leukemia and solid tumors, together with analogues that have better pharmacodynamic properties, alone or in combination with other anti-cancer drugs (Miller et al., "Clinical pharmacology of sodium butyrate in patients with acute leukemia," (1987) *Euro J. Cancer Clin. Oncol.* 23:1283-1287; Conley et al. "Phase I study of the orally administered butyrate prodrug, tributyrin, in patients with solid tumors," (1998) *Clin Cancer Res.* 4:629-634). Butyrate was also shown to induce WAF1/Cip1 (a potent inhibitor of cyclin-dependent kinases) mRNA in a human colorectal cancer cell line (WiDr), and cause G1-phase arrest (Katsunori N. et al., (1997) *JBC* 272(35): 22199-22206). Due to its antiproliferative effects and lack of toxicity, butyrate has received attention as a potential cancer therapeutic agent.

G protein-coupled receptors are under intense scrutiny as potential targets of drug research, mostly because of the sheer size and diversity of this receptor family as well as the recognized high levels of specificity and sensitivity attainable by drugs targeting these receptors. Recently, Emmanuel et al. "Functional Characterization of Human Receptors for Short Chain Fatty Acids and Their Role in Polymorphonuclear Cell Activation," (2003) *J. Biol. Chem.* 278(28):25481-25489, characterized two previously-designated orphan G protein-coupled receptors, GPR41 and GPR43, as receptors for SCFAs. Both butyrate and propionate are agonists for GPR41, whereas acetate was more selective for GPR43. The four genes encoding these receptors are intronless and are clustered onto chromosomal region 19q13.1. Although little information is available concerning these receptors, GPR41 was shown to induce apoptosis via the p53/Bax pathway in an ischemia/reperfusion paradigm (Kimura et al., (2001) *J. Biol. Chem.* 276(28):26453-26460).

Membrane transport in cells is a fundamental biological process that is mediated by various transporter and channel proteins. A major type of such proteins is a secondary active membrane transporter that uses a solute gradient to drive the translocation of other substrates (Mitchell, P., (1963) *Biochem Soc. Symp.* 22:141). Successful drug delivery will achieve an appropriate drug concentration at the target to elicit a desired level of response. Delivery of drugs through known transport systems has been under investigation for many years.

$ATB^{0,+}$ is a broad substrate-specificity transporter that recognizes neutral as well as cationic amino acids as substrates. $ATB^{0,+}$ is expressed primarily in the colon, lung and eye (Hatanaka, T. et al., (2003) *J. Pharmacol. Exp. Ther.* 308(3):

1138-1147). ATB$^{0,+}$ transports D-amino acids (Hatanaka, T. et al., (2002) *Biochem. Biophys. Res. Commun.* 291-295,), nitric acid synthase (NOS) inhibitors (Hatanaka, T. et al., (2001) *J. Clin. Invest.* 107(8):1035-1043,), and carnitine and its esters (Nakanishi et al., (2001) *J. Physiol.* 532(Pt 2):297-304).

SLC5A8 (SLC stands for solvent-linked carrier) was recently identified as a candidate tumor suppressor gene in humans that is silenced by methylation in colon cancer (Li, H, et al. (2003) *Proc. Natl. Acad. Sci. USA* 100, 8412-8417). The protein encoded by SLC5A8 is a putative transporter belonging to the Na$^+$/glucose cotransporter gene family. (Wright, E. M., and Turk, E. (2003) *Pflugers Arch. Eur. J. Physiol.* (Epub ahead of print, May 14, 2003)). SLC5A8 has been shown to transport Na$^+$ when expressed in *Xenopus* oocytes (Li, H, et al. (2003), supra), but the cotransported organic/inorganic substrate has not been identified. Interestingly, the cloning of an identical cDNA has been reported independently by Rodriguez et al. (Rodriguez, A. M., et al. (2002) *J. Clin. Endocrinol. Metab.* 87, 3500-3503) who claimed that the cDNA codes for an uncoupled passive transporter for iodide. This reported functional feature of SLC5A8 as a passive iodide transporter has apparently led to the labeling of this transporter as SLC5A11 in a recent review by Wright and Turk (2003), supra). The findings by Li et al., (2003), supra that SLC5A8 is a Na$^+$ transporter are in contradiction with those by Rodriguez et al., (2003), supra that the same protein functions as an uncoupled (i.e. no Na$^+$ involvement in the transport process) iodide transporter.

SLC5A8 is a candidate tumor suppressor in human colon and silencing of its expression by epigenetic mechanisms represents an early event in the progression of colorectal cancer (Li, H, et al. (2003) *Proc. Natl. Acad. Sci. USA* 100, 8412-8117). Re-expression of the gene in colon tumor cell lines prevents colony formation. This is the first time a plasma membrane transporter has been postulated to function as a tumor suppressor. SLC5A8 is a Na+-coupled transporter for short-chain fatty adds (acetate, propionate, and butyrate), lactate, pyruvate, and nicotinate (Miyauchi, S., Gopal, E., Fei, Y. J. & Ganapathy, V. "Functional identification of SLC5A8, a tumor suppressor down-regulated in colon cancer, as a Na$^+$-coupled transporter for short-chain fatty acids," *J. Biol. Chem.* 279, 13293-13296 (2004); Coady, M. J. et al. "The tumor suppressor gene SLC5A8 expresses a Na$^+$-monocarboxylate cotransporter," *J. Physiol. (Lond.)* 557, 719-731 (2004); Gopal, E. et al. "Expression of slc5a8 in kidney and its role in Na+-coupled transport of lactate," *J. Biol. Chem.* 279, 44522-11532 (2004); Gopal, E. et al. "Sodium-coupled and electrogenic transport of B-complex vitamin nicotinic acid by slc5a8, a member of the Na/glucose co-transporter gene family," *Biochem. J.* 388, 309-316 (2005)). Accordingly, SLC5A8 has been named SMCT1 (Sodium-coupled monocarboxylate transporter 1). As used herein, the terms SLC5A8 and SMCT1 are used interchangeably and refer to the same Na+-coupled transporter. It is not clearly known, however, how the transport function of SLC5A8 is related to its putative tumor suppressive role.

Pyruvate is the anionic form of the three-carbon organic acid, pyruvic acid. Pyruvate is a key intermediate in the glycolytic and pyruvate dehydrogenase pathways, which are involved in biological energy production. Pyruvate serves as a biological fuel by being converted to acetyl coenzyme A, which enters the tricarboxylic acid or Krebs cycle where it is metabolized to produce ATP aerobically. Energy can also be obtained anaerobically from pyruvate via its conversion to lactate. It has been suggested that 3-bromopyruvate may be effective as a cancer suppressor (Nelson, K. "3-Bromopyruvate kills cancer cells in animals," (2002) *Lancet. Oncol.* 3(9):524; Geschwind et al. "Novel therapy for liver cancer: direct intraarterial injection of a potent inhibitor of ATP production," (2002) *Cancer Res* 62(14):3909-13; Ko et al. "Advanced cancers: eradication in all cases using 3-bromopyruvate therapy to deplete ATP," (2004) *Biochem. Biophys. Res. Commun.* 324(1):269-75). As shown herein, the tumor suppressive role of SLC5A8 is associated with pyruvate-dependent inhibition of histone deacetylases (HDACs).

Butyrate is also an inhibitor of HDACs. HDAC inhibitors have shown promise in the treatment of cancer (Marks, P. et al. "Histone deacetylases and cancer: causes and therapies," (2001) *Nat. Rev. Cancer* 1, 194-202; Vigushin, D. M. & Coombes, R. C. "Histone deacetylase inhibitors in cancer treatment," (2002) *Anti-cancer Drugs* 13, 1-13; Davie, J. R. "Inhibition of histone deacetylase activity by butyrate," (2003) *J. Nutr.* 133, 2485S-2493S; Drummond, D. C. et al., "Clinical development of histone deacetylase inhibitors as anticancer agents," (2005) *Annu. Rev. Pharmacol. Toxicol.* 45, 495-528). The tumor-selective sensitization of cells to apoptosis by butyrate involves the tumor cell-specific induction of death receptor pathway or activation of the pro-apoptotic protein Bim (Nakata, S. et al. "Histone deacetylase inhibitors upregulate death receptor 5/TRAIL-R2 and sensitize apoptosis induced by TRAIL/APO2-L in human malignant tumor cells," (2004) *Oncogene* 23, 6261-6271; Insinga, A. et al. "Inhibitors of histone deacetylases induce tumor-selective apoptosis through activation of the death receptor pathway," (2005) *Nat. Med.* 11, 71-76; Nebbioso, A. et al. "Tumor-selective action of HDAC inhibitors involves TRAIL induction in acute myeloid leukemia cells," (2005) *Nat. Med.* 11, 77-84; Zhao, Y. et al., "Inhibitors of histone deacetylases target the Rb-E2F1 pathway for apoptosis induction through activation of proapoptotic protein Bim," (2005) *Proc. Natl. Acad. Sci. USA* 102, 16090-16095). Therefore, the entry of butyrate into colonic epithelial cells via SLC5A8 may explain the tumor suppressive role of the transporter in the colon.

As shown herein, SLC5A8 controls histone acetylation and apoptosis by mediating the entry of endogenous HDAC inhibitors, such as butyrate and pyruvate, into cells. Since SLC5A8, which transports butyrate from the colonic lumen into colonic epithelial cells, is downregulated in colon cancer, tributyrin, butyrate or similar tumor suppressors cannot be effectively targeted to colon cancer cells. Compositions and methods are needed for targeting biologically active molecules to cells where they are needed, especially under conditions in which the normal transport mechanisms for these molecules are impaired.

SUMMARY OF THE INVENTION

This invention is based in part on the discovery that the amino acid transporter ATB$^{0,+}$ is upregulated in colon cancer, inflammatory bowel disease, Crohn's disease, ulcerative colitis, cervical cancer, lung cancer, and other cancers resulting from metastasis from primary colon cancer sites. It is also based on the discovery that this transport system can be used to transport an amino acid that has been modified to comprise a short-chain fatty acid moiety, such as butyrate or pyruvate, into affected cells where the short-chain fatty acids can exert their effects.

This invention is also based in part on the inventors' discovery that SCL5A8 (SMCT1) is the normal butyrate transporter. Since SLC5A8 is downregulated in colon cancer, use of the ATB$^{0,+}$ transporter to transport short-chain fatty acid moieties is especially effective for treatment of colon cancer by administering an amino acid that has been modified to comprise butyrate or pyruvate.

Because the $ATB^{0,+}$ transporters natural function is as an arginine transporter that provides the nitric oxide from arginine needed to keep blood vessels dilated where cells are rapidly proliferating, its upregulation in all types of cancers is indicated. It can thus be used to transport and target any known anticancer agent to cancer cells, thus reducing the dosage of these toxic chemicals required and reducing their damaging effects to healthy tissue. Examples of anticancer drugs that can be conjugated to amino acids for delivery to cancer cells include nucleoside drugs whose final groups can be attached to amino acids, and other anticancer drugs known to the art, e.g., 5' fluorouracil, doxorubicin, daunorubicin, vinblastine, and cysplatin.

Preferably, this invention provides prodrugs of biologically active short-chain fatty acids and their derivatives that are capable of intracellular transport by $ATB^{0,+}$. The prodrugs comprise an amino acid (which may be a modified amino acid, i.e., an amino acid modified to provide a site, such as an OH group, for attachment of the short-chain fatty acid) capable of intracellular transport by $ATB^{0,+}$ attached to the short-chain fatty acid. Pharmaceutically-acceptable salts of such prodrugs are also provided.

Preferably, the short-chain fatty acid is attached to the amino acid through a hydroxyl group of the amino acid to form an ester with the amino acid, although it may also be attached through the amino group of the amino acid to form an amide with the amino acid.

The $ATB^{0,+}$ transporter is capable of transporting both neutral and cationic amino acids, including modified amino acids. Neutral cationic amino acids known to the art are amino acids which are not charged at physiological pH, and include glycine, alanine, valine, leucine, isoleucine, phenylalanine, tyrosine, tryptophan, proline, serine and threonine. Amino acids which are cationic are lysine, arginine, histidine, and ornithine.

A useful class of amino acid moieties for the prodrugs of this invention is made up of the L-enantiomers of alanine, serine, methionine, leucine, tryptophan, threonine, histidine, phenylalanine, glutamine, asparagine, lysine, arginine, valine, tyrosine, and isoleucine and the D-enantiomers of alanine, serine, methionine, leucine, and tryptophan.

A preferred class of amino acid moieties for the prodrugs of this invention is made up of the L-enantiomers of serine, threonine and tyrosine.

In one embodiment, this invention provides a prodrug of a biologically active anticancer drug, short-chain fatty acid or derivative thereof, wherein said prodrug is capable of intracellular transport by $ATB^{0,+}$; and said prodrug comprises an amino acid or derivative thereof capable of intracellular transport by $ATB^{0,+}$ attached to said anticancer drub, short-chain fatty acid or derivative thereof; and pharmaceutically acceptable salts of said prodrug. Preferably the short-chain fatty acid or derivative thereof is selected from the group consisting of acetate, propionate, pyruvate, and butyrate. In a further embodiment, the short-chain fatty acid or derivative thereof is 3-bromopyruvate.

In one embodiment, the prodrug is serine butyrate, also referred to herein as O-butyryl serine. Other preferred prodrugs are serine propionate, also referred to herein as O-propionyl serine, serine acetate, also referred to herein as O-acetyl serine, and serine pyruvate.

This invention also provides a method for delivering a biologically-active short-chain fatty acid or other anticancer drug to cells of a patient in which the taffy acid or other anticancer drug can exhibit biological activity, the method comprising attaching the fatty acid or other anticancer drug to an amino acid capable of being transported by $ATB^{0,+}$ to form a prodrug as described above, and administering an effective amount of this prodrug to the patient.

The method is preferably used to treat a condition in which the $ATB^{0,+}$ transport system is upregulated, such as colon cancer, inflammatory bowel disease, ulcerative colitis, Crohn's disease, lung cancer, cervical cancer, and cancers caused by metastases from primary colon cancer sites. The method may also be used to deliver short-chain fatty acids to patients in need of these compounds for use as energy substrates for cell metabolism, or as therapeutic compounds to treat diseases in which the $ATB^{0,+}$ system is not upregulated.

This invention further provides method for treating a disease condition characterized by upregulation of $ATB^{0,+}$ comprising administering to a patient having said disease a therapeutically-effective amount of a fatty-acid-amino acid prodrug as described above. In a further embodiment, the disease condition is characterized by downregulation of SLC5A8.

BRIEF DESCRIPTION OF THE FIGURES

FIG. 4. Immunohistochemical analysis of ATB$^{0,+}$ protein expression in hepatic and lymph node metastases.

FIG. 9A shows saturation kinetics for ATB$^{0,+}$-mediated glycine uptake in the absence (•) and presence of 5 mM L-serine (○), 5 mM O-acetyl-L-serine (▼), 5 mM O-propionyl-L-serine (∇) and 5 mM O-butyryl-L-serine (■).

FIG. 12. Na$^+$- and Cl$^-$-activation kinetics of O-butyryl-L-serine-induced currents in Xenopus oocytes expressing rat ATB$^{0,+}$. Rat ATB$^{0,+}$ was expressed in Xenopus oocytes heterologously. For Na$^+$-activation kinetics (FIG. 12A), the current induced by 2 mM O-butyryl-L-serine was measured in the presence of increasing concentrations of Na$^+$ with a fixed concentration of Cl$^-$ (100 mM). Inset: Hill plot. For Cl$^-$ activation kinetics (FIG. 12B), the current induced by 2 mM O-butyl-L-serine was measured in the presence of increasing concentration of Cl$^-$ with a fixed concentration of Na$^+$ (100 mM).

FIG. 13. Purity of the preparations of the L-serine esters of SCFA. Amino acid analysis of (A) L-serine, (B) O-propionyl-L-serine and (C) O-butyryl-L-serine was conducted using Beckman High Performance Amino Acid Analyzer.

FIG. 19. Expression of SMCT1 and HDAC inhibition during mammary gland involution in wild type (c/ebpδ$^{+/+}$) and c/ebpδ$^{-/-}$ mice.

FIG. 21. Differential expression of C/EBPδ and SMCT1 in non-transformed and transformed mammary epithelial cell lines and its relevance to HDAC inhibition and apoptosis in breast cancer cells.

FIG. 23. Induction of C/EBPδ/SMCT1 and apoptosis in breast cancer cell lines by HDAC inhibitors.

FIG. 25. Pyruvate functions as a HDAC inhibitor and a tumor suppressor.

Figure 1A:
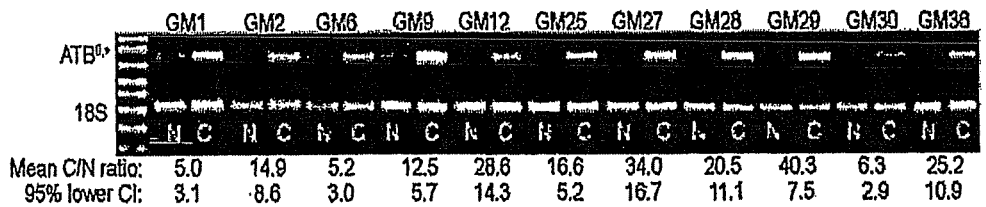
FIG. 1. Semi-quantitative RT-PCR of paired normal and cancer tissue from colorectal cancer and metastasis. $ATB^{0,+}$ (FIG. 1A) and iNOS (FIG. 1B) mRNA expression was assessed by semi-quantitative RT-PCR and shown to be increased in colorectal cancer and metastasis. Representative gels from normal (N) and cancer (C) tissue from each patient are shown in these composites. The patient's serial numbers (GM1, GM2, etc.) are given above the gels. The size of the $ATB^{0,+}$-specific RT-PCR product is 754 bp and the size of the iNOS-specific RT-PCR product is 1281 bp. 18S rRNA is the internal control and the size of its specific RT-PCR product is 315 bp. The DNA size ladder is in the first lane of each composite. The mean ratio of mRNA expression in cancer tissue compared to normal tissue (mean C/N ratio), after normalization with 18S rRNA levels, is shown below each pair. The lower limit of the 95% confidence interval (95% CI) is shown below the mean ratio for each patient's pair of samples.
(FIG. 1C) Overall, colorectal cancer showed a 22.9±3.0-fold increase in $ATB^{0,+}$ mRNA expression (p<0.0001) and a 5.2±1.1-fold increase in iNOS mRNA expression (p<0.002) compared to patient-matched normal colorectal tissue. PCR was repeated with each DNA sample at least 4 times under identical conditions to obtain the cumulative data shown.

DETAILED DESCRIPTION (The upregulation of $ATB^{0,+}$ in cancer makes this transporter useful for the delivery of chemotherapeutic agents. It has been shown previously that $ATB^{0,+}$ is a versatile delivery system for a variety of drugs and prodrugs (Hatanaka, T., et al. "Transport of amino acid-based prodrugs by the $Na^+$- and $Cl^-$-coupled amino acid transporter $ATB^{0,+}$ and expression of the transporter in tissues amenable for drug delivery," (2004) *J. Pharmacol. Exp. Ther.* 308: 1138-1147; Umapathy, N. S., et al. "Transport of amino acid esters and the amino-acid-based prodrug valganciclovir by the amino acid transporter $ATB^{0,+}$," (2004) *Pharm. Res.* 21: 1303-1310). $ATB^{0,+}$ is also highly suitable for the delivery of NOS inhibitors into cells (Hatanaka, T. et al. "$Na^+$- and $Cl^-$-coupled active transport of nitric oxide synthase inhibitors via amino acid transport system $B^{0,+}$," (2001) *J. Clin. Invest.* 107: 1035-1043). This class of compounds is useful in cancer chemotherapy (Crowell, J. A. et al. "Is inducible nitric oxide synthase a target for chemoprevention?" (2003) *Mol. Cancer. Ther.* 2: 815-823). NOS inhibitors are substrates for $ATB^{0,+}$ and therefore instead of arginine entering the cancer cells via this transporter, NOS inhibitors gain access into cells. Once inside the cells, NOS inhibitors block the function of iNOS and suppress the generation of NO. As the expression of $ATB^{0,+}$ is markedly and specifically elevated in cancer cells, the actions of NOS inhibitors is directed primarily to cancer cells. The compositions and methods of this invention are also relevant to the treatment of patients with lymphatic spread or hepatic metastasis from colonic primaries. Normal lymph nodes and liver expresses very little $ATB^{0,+}$ (Sloan, J. L. and Mager, S. "Cloning and functional expression of a human $Na^+$- and $Cl^-$-dependent neutral and cationic amino acid transporter $B^{0,+}$," (1999) *J. Biol. Chem.*, 274: 23740-23745), but the expression of the transporter is markedly enhanced in colorectal cancer metastases in the lymph nodes and liver. Perimetastatic regions of the liver, free of metastasis, also express high levels of $ATB^{0,+}$ thus ensuring a 'kill zone' around the metastasis where chemotherapy agents can be delivered in a manner similar to establishing negative margins after surgical resection. Using this transporter for pharmacotherapy is therefore beneficial in patients with colon cancer with and without lymphatic spread and hepatic metastasis.

The butyrate prodrug of this invention is especially useful for the treatment of colon cancer. As discussed above, the transport system used in the colon to transfer butyrate from the colonic lumen to colon epithelial cells, is SLC5A8 (Li, et al. "SLC5A8, a sodium transporter, is a tumor suppressor gene silenced by methylation in human colon aberrant crypt foci and cancers," (2003) *PNAS* 100(14):8412-8417). Because this transporter is downregulated in colon cancer, butyrate and known prodrugs of butyrate such as tributyrin (glyceryl tributyrate), are of limited therapeutic effectiveness in treating colon cancer because they are not effectively transported into the affected cells by this downregulated transporter. In addition, tributyrin is not effective for targeting the therapeutically effective butyrate to colon cancer because tributyrin must be hydrolyzed to butyrate in the digestive system before it can be transported by SLC5A8. In contrast, the amino acid-butyrate conjugates of this invention accumulate preferentially in colon cancer cells (i.e., ten times more than in other cells), where they are readily hydrolyzed by cellular enzymes to butyrate.

As reported herein, $ATB^{0,+}$ is upregulated in colon cancer. It can be used as a transport system for a prodrug of butyrate wherein butyrate is conjugated to an amino acid moiety capable of being transported by $ATB^{0,+}$.

The term "biologically active" means capable of causing an observable change in the structure, function, or composition of a cell upon uptake by the cell. Such observable changes include inhibition or activation of an enzyme, inhibition or activation of binding between members of a binding pair, an increased or decreased rate of synthesis of a metabolite, increased or decreased cell respiration, metabolism, proliferation, and other effects known to the art.

A prodrug of this invention is a biologically-active short-chain fatty acid or other anticancer drug attached to an amino acid by means of a linkage that is releasable. The biologically-active short-chain fatty acid is biologically inactive until the linkage is released, e.g., by hydrolysis or other cleaving reaction known to the art. The attachment may be of any type known to the art. Preferably, the attachment is a covalent bond such as an ester or amide linkage that can be released inside the target cell by endogenous enzymes.

A short-chain fatty acid as used herein refers to a fatty acid having 1-8 carbon atoms in the carbon chain. As used herein, preferred short-chain fatty acids are butyrate, acetate, pyruvate and propionate. Butyrate has a therapeutic effect in the treatment and prevention of colon cancer and other diseases as described above. Acetate and propionate are biologically active in serving as energy substrates for cells. In addition propionate is an appetite suppressant.

Biologically active derivatives of short-chain fatty acids or other anticancer drugs, e.g., having substituents on the carbon chain such as O, S, N, methyl, ethyl, halogen, and other groups that either do not interfere with their biological activity or which cause them to be biologically active, and also do not interfere with their ability to be transported by $ATB^{0,+}$, may also be used to form the prodrugs of this invention. In one embodiment, this invention comprises pyruvate or a pyruvate derivative, such as 3-bromopyruvate, attached to an amino acid by means of a linkage that is releasable. In one embodiment, this invention comprises a pyruvate ester of an amino acid.

The prodrugs of this invention may be prepared by methods known to the art, and by the methods disclosed herein and analogous methods.

As used herein, "pharmaceutically acceptable salts" refer to derivatives of the disclosed compounds wherein the parent compound, i.e., a prodrug of this invention, is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the fine acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

The term "amino acid" as used herein includes both naturally-occurring amino acids and modified amino acids that have been modified to have side chains capable of linking with the biologically-active short-chain fatty acid moieties. The addition of a hydroxyl moiety to an amino acid to allow the formation of an amino acid ester of the amino acid is a preferred modification. The term "amino acid" also includes both the L-enantiomers and D-enantiomers thereof. Such modified amino acids may be prepared by methods well-known to the art.

The L-enantiomer of serine butyrate is a preferred prodrug of this invention because butyrate has received FDA approval as safe and effective and, in addition, L-serine is not toxic. Although the D-enantiomer of serine and other amino acids may be used, as discussed above. D-serine has biological activity which might be contraindicated in particular patients (Hatanaka, T., et al. "Transport of D-serine via the amino acid transporter ATB$^{0,+}$ expressed in the colon," (2002) *Biochem. Biophys. Res. Commun.* 291(2): 291-295).

A "patient" as used herein is an animal of any species, preferably a mammal such as a livestock animal or personal companion animal, and more preferably a human.

The prodrugs of this invention may be administered in a pharmaceutically acceptable carrier, such as an oral delivery carrier, a suppository delivery carrier, an intravenous delivery carrier, or an aerosol carrier. Excipients, adjuvants, and the like for the prodrugs can be included in the prodrug compositions of this invention. Preferably, the composition will be about 5% to 75% by weight of a compound or compounds of the invention, with the remainder consisting of suitable pharmaceutical excipients. Appropriate excipients can be tailored to the particular composition and route of administration by methods well known in the art, e.g., *Remington's Pharmaceutical Sciences,* 18th Ed., Mack Publishing Co., Easton, Pa. (1990).

For oral administration, such excipients include pharmaceutical grades of mannitol, lactose, starch, magnesium stearate, sodium saccharine, talcum, cellulose, glucose, gelatin, sucrose, magnesium carbonate, and the like. The composition may take the form of a solution, suspension, tablet, pill, capsule, powder, sustained-release formulation, and the like.

In some embodiments, the pharmaceutical compositions take the form of a pill, tablet or capsule, and thus, the composition can contain, along with the biologically active prodrug, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof.

The active compounds of the formulas may be formulated into a suppository comprising, for example, about 0.5% to about 50% of a compound of the invention, disposed in a polyethylene glycol (PEG) carrier (e.g., PEG 1000 [96%] and PEG 4000 [4%]).

Liquid compositions can be prepared by dissolving or dispersing the prodrug of this invention (e.g., about 0.5% to about 20%), and optional pharmaceutical adjuvants in a carrier, such as, for example, aqueous saline (e.g., 0.9% w/v sodium chloride), aqueous dextrose, glycerol, ethanol and the like, to form a solution or suspension, e.g., for intravenous administration. The active compounds may also be formulated into a retention enema.

If desired, the composition to be administered may also contain minor amounts of non-toxic auxiliary substances such as wetting or emulsifying agents, pH buffering agents, such as, for example, sodium acetate, sorbitan monolaurate, or triethanolamine oleate.

For topical administration, the composition is administered in any suitable format, such as a lotion or a transdermal patch. For delivery by inhalation, the composition can be delivered as a dry powder (e.g., Inhale Therapeutics) or in liquid form via a nebulizer.

Methods for preparing such dosage forms are known or will be apparent to those skilled in the art; for example, see Remington's Pharmaceutical Sciences, 17th ed., Mack Publishing Company, Easton, Pa., 1985, p. 1418, and similar publications. The composition to be administered will, in any event, contain a quantity of the prodrug in a pharmaceutically effective amount for relief of the condition being treated when administered in accordance with the teachings of this invention.

Serine butyrate is suitable for oral administration because it withstands digestive enzymes. It can be delivered as an aerosol because the ATB$^{0,+}$ transport system works in the lungs. It can be given as a rectal suppository if the site of the cancer is in the rectum. For cervical cancer it can be administered as a topical cream. It can also be administered intravenously for these and other cancers, e.g., cancers resulting from metastases from primary colon cancer sites.

Generally, the compounds of the invention are administered in a therapeutically effective amount, i.e., a dosage sufficient to effect treatment, which will vary depending on the individual and condition being treated. Typically, a therapeutically effective daily dose is from 0.1 to 100 mg/kg of body weight per day of drug. Most conditions respond to administration of a total dosage of between about 1 and about 30 mg/kg of body weight per day, or between about 70 mg and 2100 mg per day for a 70 kg person.

The fatty-acid esters and amides of neutral and cationic amino acids making up the prodrugs of this invention may be synthesized by means known to the art without undue experimentation.

Overproduction of nitric oxide (NO) has been implicated in the pathogenesis of a variety of cancers, including colorectal cancer (Thomsen, L. L. and Miles, D. W., "Role of nitric oxide in tumour progression: lesions from human tumours," (1998) Cancer Metastasis Rev. 17:107-118; Ambs, S. et al., "Frequent nitric oxide synthase-2 expression in human colon adenomas: implication for tumor angiogenesis and colon cancer progression," (1998) Cancer Res. 58:334-341; Jaiswal, M. et al, "Inflammatory cytokines induce DNA damage and inhibit DNA repair in cholangiocarcinoma cells by a nitric oxide-dependent mechanism," (2000) Cancer Res. 60:184-190; Lala, P. K., "Significance of nitric oxide in carcinogenesis, tumor progression and cancer therapy," (1998) Cancer Metastasis Rev. 17:1-6; Murata, J. et al., "Nitric oxide as a carcinogen: analysis by yeast functional assay of inactivating p53 mutations induced by nitric oxide," (1997) Mutat. Res. 379:211-218; Ambs, S. et al., "Relationship between p53 mutations and inducible nitric oxide synthase expression in human colorectal cancer," (1999) J. Natl. Cancer Inst. 91:86-88; Jenkins, D. C. et al., "Roles of nitric oxide in tumor growth," (1995) Proc. Natl. Acad. Sci. USA 92:4392-4396). NO is synthesized from arginine by nitric oxide syntheses (NOS).

Of the three NOS isoforms, overactivity of the inducible NOS (iNOS) isoform is associated with colorectal cancer development (Ambs, S. et al., "Frequent nitric oxide synthase-2 expression in human colon adenomas: implication for tumor angiogenesis and colon cancer progression," (1998) Cancer Res. 58:334-341; Kojima, M. et al., "Nitric oxide synthase expression and nitric oxide production in human colon carcinoma tissue," (1999) J. Surg. Oncol. 70:222-229; Yagihashi, N. et al., "Increased in situ expression of nitric oxide synthase in human colorectal cancer," (2000) Virchows Arch. 436:109-114; Lagares-Garcia, J. A. et al., "Nitric oxide synthase as a marker in colorectal carcinoma," (2001) Am. Surg. 67:709-713). Increased iNOS expression and NO levels in azoxymethane-induced rat colon cancer has been demonstrated by Takahashi et al., "Increased expression of inducible and endothelial constitutive nitric oxide synthases in rat colon tumors induced by azoxymethane," (1997) Cancer Res. 57:1233-1237. Kojima et al. demonstrated a significant increase in iNOS mRNA expression in human colon cancer tissue compared to matched normal colonic epithelium from the same subjects (Kojima, M. et al., "Nitric oxide synthase expression and nitric oxide production in human colon carcinoma tissue," (1999) J. Surg. Oncol. 70:222-229). The expression in cancer was almost twice that in normal colon. Further immunohistochemical studies demonstrated that iNOS protein and nitrotyrosine residues were markedly increased in colon cancer, though it showed some variation from region to region in the cancer. (Jenkins, D. C. et al., Human colon cancer cell lines show a diverse pattern of nitric oxide synthase gene expression and nitric oxide generation, (1994) Br. J. Cancer 70:847-849.)

The studies reported herein confirmed previous findings with regard to increased expression inducible nitric oxide synthases (iNOS) and increased levels of cellular proteins containing nitrotyrosine in colorectal cancer. Since nitric oxide (NO) is unstable, the levels of proteins containing nitrotyrosine represent a reliable indicator of in vivo exposure of the cellular proteins to NO and its metabolites such as peroxynitrite. The present studies provide evidence for increased expression of iNOS in liver metastasis from colonic primaries. The biochemical phenotype of the colonic primaries is maintained in even the metastatic tissue.

$ATB^{0,+}$ is a transporter of arginine. While there is convincing evidence in the literature for increased demand for the amino acid arginine in cancer tissues, very little information is available on the molecular mechanisms available in colon cancer tissue to meet the increased demand for this amino acid. Previously-published studies in the area of arginine uptake were done with colon cancer cell lines rather than native colon cancer tissue specimens. One of the original studies to identify arginine transport mechanisms in colon cancer using cell lines came from Condon et al., "Characterization and growth factor stimulation of L-arginine transport in a human colon cancer cell line," (1995) Ann. Surg. Oncol. 2:257-265. These investigators characterized arginine transport before and after a mitogenic stimulus in SW480, a primary human colon adenocarcinoma cell line. This cell line is characterized by high levels of constitutive expression of iNOS and NO production (Jenkins, D. C. et al., "Roles of nitric oxide in tumor growth," (1995) Proc. Natl. Acad. Sci. USA 92:4392-4396). Arginine transport in unstimulated cells occurred via $Na^+$-independent and $Na^+$-dependent transport systems, the former contributing to a majority of total transport (70%). However, when stimulated with TGF-α and EGF, $Na^+$-dependent arginine transport increased by 100% and 66%, respectively, while $Na^+$-independent transport showed no change. The stimulus also caused cell proliferation (37% and 27%, respectively). Since a majority of arginine transport was mediated by $Na^+$-independent systems even in stimulated cells, that emphasis of the study was not directed to the $Na^+$-dependent arginine transport systems. In a follow-up study, these investigators used the SW620 cells, a metastatic NO-producing colon cancer cell line derived from the same patient as was the SW480 cell line (Cendan. J. C. et al., "Increased L-arginine transport in a nitric oxide-producing metastatic colon cancer cell line," (1996) Ann. Surg. Oncol. 3:501-508). In this cell line, 80% of arginine transport was $Na^+$-independent and 15% was $Na^+$-dependent. When the transport of arginine via $Na^+$-independent and $Na^+$-dependent processes were compared between the two cell lines, the authors noted that transport via $Na^+$-independent systems was much higher in the more proliferative, metastatic SW620 cells than in the primary colon cancer cell line SW480. Based on these findings, the authors concluded that $Na^+$-independent transport systems are more relevant than $Na^+$-dependent transport systems for the delivery of arginine into colon cancer cells.

The present studies focused on the $Na^+Cl^-$-dependent amino acid transport systems $ATB^{0,+}$. Paired native normal colon and colorectal cancer tissue specimens were used instead of colon cancer cell lines in these studies. This transporter is expressed in the brush border membrane of normal colonocytes and has unique characteristics with respect to arginine transport (Hatanaka, T. et al., "Transport of D-serine via the amino acid transporter $ATB^{0,+}$ expressed in the colon," (2002) Biochem. Biophys. Res. Commun. 291:291-295). The transport of arginine via $ATB^{0,+}$ is coupled to transmembrane gradients of $Na^+$ and $Cl^-$ and to membrane potential. Inventors hereof have found that the $Na^+:Cl^-$:amino acid stoichiometry is 2:1:1 irrespective of whether the transported amino acid is a neutral amino acid or a cationic amino acid. With this stoichiometry, the number of positive charges transferred into cells varies depending on the transported amino acid substrate. If it is a zwitterionic neutral amino acid such as glycine, the transport process is associated with the transfer of a single positive charge into cells per transport cycle. In contrast, if it is a cationic amino acid such as arginine, the transport process is associated with the transfer of two positive charges into cells per transport cycle. This increases the contribution of membrane potential as the driving force for the cellular uptake of cationic amino acids and thus enhances the concentrative ability of ATB$^{0,+}$ for arginine compared to neutral amino acids. Since cancer tissues express high levels of NOS and generate markedly high levels of NO, ATB$^{0,+}$ with its unique properties in terms of its ability to mediate the influx of arginine into cells was thought to be ideally suited to meet the increased demands for arginine in cancer cells. This formed the rationale for the present studies.

The present studies have shown unequivocally that, in each and every colorectal cancer specimen examined, the expression of ATB$^{0,+}$ is increased several-fold compared to corresponding control specimens from the same patients. The increase in expression is about 20-fold in terms of steady-state levels of ATB$^{0,+}$ mRNA. The increase in mRNA levels is accompanied by a parallel increase in ATB$^{0,+}$ protein. The enhanced expression of ATB$^{0,+}$ protein is also seen in each and every colorectal cancer specimen with no exception. These findings are remarkable for their consistency and reproducibility in all of the patients included in the study. The data from liver and lymph node metastases from colonic primaries are also equally interesting. The increased expression of ATB$^{0,+}$ protein is clearly evident in the metastases. The detection of enhanced ATB$^{0,+}$ in the histologically normal perimetastatic region of the liver tissue suggests that cancer cells elaborate certain factors that act on the adjacent liver cells to induce the expression of the transporter.

SNAT4 is a transporter that has the ability to accumulate arginine inside the cells by a process energized by an electrochemical Na$^+$ gradient (T. Hatanaka, et al. "Evidence for the transport of neutral as well as cationic amino acids by ATA3, a novel and liver-specific subtype of amino acid transport system," (2001) *A. Biochim. Biophys. Acta* 1510:10-17). This transporter is however expressed normally only in liver (M. Sugawara, et al. "Structure and function of ATA3, a new subtype of amino acid transport system A, primarily expressed in the liver and skeletal muscle," (2000) *Biochim. Biophys. Acta* 1509:7-13; T. Hatanaka, et al. "Evidence for the transport of neutral as well as cationic amino acids by ATA3, a novel and liver-specific subtype of amino acid transport system," (2001) *A. Biochim. Biophys. Acta* 1510:10-17). There is no information available in the literature on cancer-associated alterations in the expression of this transporter in tumor tissues. In the present study, we investigated the expression of SNAT4 in control and paired cancer tissues from patients with colorectal cancer. In a majority of cases, the expression of this transporter was not altered in association with cancer. There was however one case in which the expression was increased in cancer tissue compared to the corresponding cancer tissue. Since this transporter is expressed predominantly in the liver under normal conditions, we examined the expression of the transporter in liver metastasis of colon cancer. We found the expression to be decreased in liver metastatic tissue compared to the control liver tissue. Thus, the cancer-associated changes in the expression of SNAT4 were not uniform in all cancer samples.

Extracellular arginine supports NO production in a variety of cell types even though intracellular concentrations of arginine are several hundred μM and all three isoforms of NOS have a $K_m$ for arginine in the range of 3-30 μM (Closs, E. I. et al., "Substrate supply for nitric-oxide synthase in macrophages and endothelial cells: role of cationic amino acid transporters," (2000) *Mol. Pharmacol.* 57:68-74). NOS should be expected to function at maximal levels under these conditions because the enzyme would be saturated with arginine at these concentrations. Therefore, extracellular arginine should have no effect on NO production via NOS. But, exposure of cells to extracellular arginine does lead to increased production of NO. These apparently contradicting findings, originally observed in endothelial cells which express endothelia NOS (eNOS) are well-known in the field of NO research as the "arginine paradox" (Forstermann, U. et al., "Nitric oxide synthase isozymes. Characterization, purification, molecular cloning, and functions," (1994) *Hypertension* 23:1121-1131).

It is believed compartmentalization of eNOS and cytosolic arginine limits access to cytosolic arginine in endothelial cells. Co-localization of eNOS with the Na$^+$-independent arginine transporter CAT-1 (one of the three isoforms of arginine transporters responsible for system y$^+$ transport activity) is believed to underlie the observed findings that extracellular arginine increases NO production via eNOS (McDonald, K. K. et al., "A caveolar complex between the cationic amino acid transport 1 and endothelial nitric-oxide synthase may explain the 'arginine paradox'," (1997) *J. Biol. Chem.* 272: 31213-31216). There may be additional molecular mechanisms involved in this process as well (Giugliano, D. et al., "The vascular effects of L-arginine in humans. The role of endogenous insulin," (1999) *J. Clin. Invest.* 99:433-438). The levels of NO generated by eNOS are several orders of magnitude lower than those generated by NOS. Therefore, NO production via iNOS would be expected to depend on extracellular arginine even more than that seen with eNOS. CAT-1 with its limited ability to concentrate arginine in cells is not suited to meet the demands for arginine in cells over-expressing iNOS. ATB$^{0,+}$ is the transporter that is responsible for delivering arginine to iNOS for production of micromolar levels of NO in cancer cells.

The present studies showing marked upregulation of ATB$^{0,+}$ expression in colorectal cancer are important not only in terms of increased demands of cancer cells for arginine for NO production but also in terms of arginine serving as an essential amino acid to support the growth and proliferation of cancer cells. Depletion of arginine in extracellular medium by arginase is known to have beneficial effect in the control of cancer cell growth (Bach, S. J. and Swaine, D., "The effect of arginase on the retardation of tumour growth," (1965) *Br. J. Cancer* 19:379-386; Umeda, M. et al., "Inhibition of the growth of cultured cells by arginase and soluble proteins from mouse skin," (1968) *Isr. J. Med. Sci.* 4:1216-1222). Cancer cells upregulate the expression of ATB$^{0,+}$ with its unique characteristics for arginine transport to obtain this amino acid from the extracellular medium to support growth as well as NO production. Arginine, as an essential amino acid for cancer cells, is obligatory to sustain cancer cell growth (Wheatley, D. N. et al., "Single amino acid (arginine) restriction: growth and death of cultured HeLa and human diploid fibroblasts," (2000) *Cell Physiol. Biochem.* 10:37-55; Scott, L. et al., "Single amino acid (arginine) deprivation: rapid and selective death of cultured transformed and malignant cells," (2000) *Br. J. Cancer* 83:800-810; Tanaka, H. et al., "Influence of the deprivation of a single amino acid on cellular proliferation and survival in rat 3Y1 fibroblasts and their derivatives transformed by a wide variety of agents," (1988) *J. Cell Physiol.* 136:421-430).

The striking colocalization of ATB$^{0,+}$ and iNOS in cancer specimens observed in the present study underscores the functional relationship between the arginine delivery process (ATB$^{0,+}$) and NO synthesizing machinery (iNOS). Arginine is also an essential amino acid for cancer cells to sustain cancer cell growth (Wheatley, D. N., et al. "Single amino acid (arginine) restriction: growth and death of cultured HeLa and human diploid fibroblasts," (2000) Cell. Physiol. Biochem. 10:37-55). Cancer cells upregulate the expression of $ATB^{0,+}$ to obtain this amino acid from the extracellular medium to support growth as well as excess NO production. The present studies have shown convincingly that the expression of $ATB^{0,+}$ is upregulated in colorectal cancer, both at the mRNA level and at the protein level. This upregulation is accompanied with a parallel increase in transport function, enhancing the delivery of extracellular arginine into Cancer cells.

NO, with its ability to enhance vascular permeability (Doi, K. et al., "Excessive production of nitric oxide in rat solid tumor and its implication in rapid tumor growth," (1996) Cancer 77:1598-1604), dilate blood vessels and to induce angiogenesis either through the induction of factors such as vascular endothelial growth factor (Jozkowicz, A. et al., "Involvement of nitric oxide in angiogenic activities of vascular endothelial growth factor isoforms," (2004) Growth Factors 22:19-28), interleukin-8 (Hellmuth, M. et al., "Nitric oxide differentially regulates pro- and anti-angiogenic markers in DLD-1 colon carcinoma cells," (2004) FEBS Lett. 563:98-102) and cyclooxygenase-2 (Cianchi, F. et al., "Cyclooxygenase-2 activation mediates the proangiogenic effect of nitric oxide in colorectal cancer," (2004) Clin. Cancer Res. 10:2694-2704) or the stabilization of hypoxia-inducible factor-1 alpha (Wellman, T. L. et al., "Nitric oxide and reactive oxygen species exert opposing effects on the stability of hypoxia-inducible factor-1 alpha (HIF-1 alpha) in explants of human pial arteries," (2004) FASEB J. 18:379-381), is essential to enhance the delivery of nutrients to the fast-growing cancer cells or to promote their invasiveness.

This obligatory role of $ATB^{0,+}$ in the growth and maintenance of tumor growth makes this transporter useful for cancer chemotherapy. When the transport of arginine via $ATB^{0,+}$ into cancer cells is blocked by specific compounds, such compounds are useful in the management of cancer.

$ATB^{0,+}$ is versatile in terms of its ability to serve as a delivery system for a variety of drugs and prodrugs. (Hatanaka, T. et al., "Transport of amino acid-based prodrugs by the $Na^+$- and $Cl^-$-coupled amino acid transporter $ATB^{0,+}$ and expression of the transporter in tissues amendable for drug delivery," (2004) J. Pharmacol. Exp. Ther. 308; 1138-1147; Umapathy, N. S. et al., "Transport of amino acid esters and the amino-acid-based prodrug valganciclovir by the amino acid transporter $ATB^{0,+}$," (2004) Pharm. Res. 21:1303-1310; U.S. Patent Publication No. 2004/0142317, Ganapathy et al., Jul. 22, 2004.) Of importance to cancer chemotherapy are the findings that $ATB^{0,+}$ is highly suitable for the delivery of NOS inhibitors into cells (Hatanaka, T., "$Na^+$- and $Cl^-$-coupled active transport of nitric oxide synthase inhibitors via amino acid transport system $B^{0,+}$," (2001) J. Clin. Invest. 107:1035-1043). This class of compounds is useful in cancer chemotherapy (Thomsen, L. L. et al., "Selective inhibition of inducible nitric oxide synthase inhibits tumor growth in vivo: studies with 1400W, a novel inhibitor," (1997) Cancer Res. 57:3300-3304; Rao, C. V. et al., "Chemoprevention of colonic aberrant crypt foci by an inducible nitric oxide synthase-selective inhibitor," (1999) Carcinogenesis 20:641-644; Rao, C. V. et al., "Chemopreventive properties of a selective inducible nitric oxide synthase inhibitor in colon carcinogenesis, administered alone or in combination with celecoxib, a selective cyclooxygenase-2 inhibitor," (2002) Cancer Res. 62:165-170; Crowell, J. A. et al., "Is inducible nitric oxide synthase a target for chemoprevention?," (2003) Mol. Cancer Ther. 2:815-823).

NOS inhibitors are substrates for $ATB^{0,+}$ and therefore block the entry of arginine into cells via $ATB^{0,+}$. Instead of arginine entering the cells via the transporter, NOS inhibitors gain access into cells via the same transporter. Once inside the cells, these compounds block the function of iNOS and suppress the generation of NO. As the expression of $ATB^{0,+}$ is markedly elevated in cancer cells in a specific manner, the actions of NOS inhibitors are restricted primarily to cancer cells with relatively little or no effect on normal cells. These data are also relevant to the treatment of patients with advanced disease, with lymphatic spread or hepatic metastasis from colonic primaries. Lymphatic spread is a major determinant of successful locoregional control after surgical resection of colorectal cancer. Liver is the most common site of distant metastasis and a major cause of mortality and morbidity from colorectal cancer. Normal lymph nodes and liver expresses very little $ATB^{0,+}$ (Sloan, J. L. and Mager, S., "Cloning and functional expression of a human $Na^+$ and $Cl^-$-dependent neutral and cationic amino acid transporter B(0+)," (1999) J. Biol. Chem. 274:23740-23745), but the expression of the transporter is markedly enhanced in colon cancer metastases in the lymph nodes and liver. Perimetastatic regions of the liver, free of metastasis, also express high levels of $ATB^{0,+}$, thus ensuring a "kill zone" around the metastasis where chemotherapy can be delivered in a manner similar to establishing negative margins after surgical resection. Using this transporter for pharmacotherapy therefore is beneficial in patients with colon cancer with or without lymphatic spread and hepatic metastasis.

EXAMPLES

Example 1

Upregulation of $ATB^{0,+}$ (SLC6A14) in Colorectal Cancer and Metastasis $ATB^{0,+}$ (SLC6A14) is a $Na^+/Cl^-$-coupled transporter expressed at low levels in the normal colon. It transports arginine in a $Na^+/Cl^-$-dependent manner. Since arginine is the substrate for nitric oxide synthases (NOS) and since nitric oxide (NO) plays a critical role in cancer, the expression of $ATB^{0,+}$ in colorectal cancer was examined. Paired normal and cancer tissues from colectomy specimens of ten patients with colorectal cancer and from the liver tissue of one patient with hepatic metastasis from a colonic primary were used for the analysis of the levels of $ATB^{0,+}$ mRNA, inducible NOS (iNOS) mRNA and the corresponding proteins. Tissue samples from the colon, liver and lymph nodes of an additional patient with metastatic colon cancer were analyzed for $ATB^{0,+}$ protein alone. The levels of nitrotyrosylated proteins were also examined. The $ATB^{0,+}$ mRNA increased 22.9±3.0 fold in colorectal cancer compared to normal tissue and the increase was evident in each of the ten cases examined. iNOS mRNA increased 5.2±1.1 fold in cancer specimens. This was associated with an increase in $ATB^{0,+}$ iNOS and nitrotyrosylated proteins. The increased expression of $ATB^{0,+}$ and iNOS was also demonstrated in liver and lymph node specimens with metastases from colonic primaries.

Evidence suggests that chronically elevated levels of nitric oxide (NO) are associated with protumorigenic effects (Thomsen, L. L. and Miles, D. W., "Role of nitric oxide in tumour progression: lesions from human tumours," (1998) Cancer Metastasis Rev. 17:107-118; Ambs, S. et al., "Frequent nitric oxide synthase-2 expression in human colon adenomas: implication for tumor angiogenesis and colon cancer progression," (1998) Cancer Res. 58:334-341; Jaiswal, M. et al., "Inflammatory cytokines induce DNA damage and inhibit DNA repair in cholangiocarcinoma cells by a nitric oxide-dependent mechanism," (2000)Cancer Res. 60:184-190;

Lela, P. K., "Significance of nitric oxide in carcinogenesis, tumor progression and cancer therapy," (1998) *Cancer Metastasis Rev.* 17:1-6; Murata, J. et al., "Nitric oxide as a carcinogen: analysis by yeast functional assay of inactivating p53 mutations induced by nitric oxide," (1997) *Mutat. Res.* 379:211-218; Ambs, S. et al., "Relationship between p53 mutations and inducible nitric oxide synthase expression in human colorectal cancer," (1999) *J. Natl. Cancer Inst.* 91:86-88; Jenkins, D. C. et al., "Roles of nitric oxide in tumor growth," (1995) *Proc. Natl. Acad. Sci. USA* 92:4392-4396), proinflammatory effects (Kimura, H. et al., "Increased expression of an inducible isoform of nitric oxide synthase and the formation of peroxynitrite in colonic mucosa of patients with active ulcerative colitis," (1998) *Gut* 42:180-187; Rachmilewitz, D. et al., "Enhanced colonic nitric oxide generation and nitric oxide synthase activity in ulcerative colitis and Chrohn's disease," (1995) *Gut* 36:718-723; Menchen, L. A. et al., "N-(3-(aminomethyl)benzyl)acetamidine, an inducible nitric oxide synthase inhibitor, decreases colonic inflammation induced by dinitrobenzene sulphonic acid in rats," (2001) *Life Sci.* 69:479-491), and anti-apoptotic effects (Radisavljevic, Z., "Nitric oxide suppression triggers apoptosis through the FKHRL1 (FOXO3A)/ROCK kinase pathway in human breast carcinoma cells," (2003) *Cancer* 97:1358-1363; Madesh, M. et al., "Nitric oxide prevents anoxia-induced apoptosis in colonic HT29 cells,"(1999) *Arch. Biochem. Biophys.* 366:240-248; Wenzel, U. et al., "Nitric oxide suppresses apoptosis in human colon cancer cells by scavenging mitochondrial superoxide anions;" (2003) *Int. J. Cancer* 106:666-675; Wenzel, U. et al., "Nitric oxide levels in human preneoplastic colonocytes determine their susceptibility toward antineoplastic agents," (2003) *Mol. Pharmacol.* 64:1494-1502).

NO is produced from arginine by nitric oxide syntheses (NOSs). The calcium-independent cytokine-inducible NOS (iNOS or NOS2) generates much higher levels of NO than the other two NOS isoforms (Nathan, C., "Nitric oxide as a secretory product of mammalian cells," (1992) *FASEB J.* 6:3051-3064). iNOS is also the only isoform capable of maintaining micromolar levels of NO for several days (Vodovotz, Y. et al., "Inactivation of nitric oxide synthase after prolonged incubation of mouse macrophages with IFN-gamma and bacterial lipopolysaccharide," (1994) *J. Immunol.* 152:4110-4118). The expression and activity of iNOS are increased in malignancies found in the breast (Bing, R. J. et al., "Nitric oxide, prostanoids, cyclooxygenase, and angiogenesis in colon and breast cancer," (2001) *Clin. Cancer Res.* 7:3385-3392; Thomsen, L. L. et al., "Nitric oxide synthase activity in human breast cancer," (1995) *Br. J. Cancer* 72:41-44), head and neck (Franchi, A. et al., "Inducible nitric oxide synthase expression in laryngeal neoplasia: correlation with angiogenesis," (2002) *Head Neck* 24:16-23; Kitano, H. et al., "Expression of inducible nitric oxide synthase in human thyroid papillary carcinomas," (1999) *Thyroid* 9:113-117), ovary (Thomsen, L. L. et al., "Nitric oxide synthase activity in fresh cells from ovarian tumour tissue: relationship of enzyme activity with clinical parameters of patients with ovarian cancer," (1998) *Biochem. Pharmacol.* 56:1365-1370; Thomsen, L. L. et al., "Nitric oxide synthase activity in human gynecological cancer," (1994) *Cancer Res.* 54:1352-1354), brain (Cobbs, C. S. et al., "Expression of nitric oxide synthase in human central nervous system tumors," (1995) *Cancer Res.* 55:727-730), and colon (Ambs, S. et al., "Frequent nitric oxide synthase-2 expression in human colon adenomas: implication for tumor angiogenesis and colon cancer progression," (1998) *Cancer Res.* 58:334-341; Bing, R. J. et al., "Nitric oxide, prostanoids, cyclooxygenase, and angiogenesis in colon and breast cancer," (2001) *Clin. Cancer Res.* 7:3385-3392; Kojima, M. et al., "Nitric oxide synthase expression and nitric oxide production in human colon carcinoma tissue," (1999) *J. Surg. Oncol.* 70:222-229; Yagihashi, N. et al., "Increased in situ expression of nitric oxide synthase in human colorectal cancer," (2000) *Virchows Arch,* 436:109-114; Lagares-Garcia, J. A. et al., "Nitric oxide synthase as a marker in colorectal carcinoma," (2001) *Am. Surg.* 67:709-713). Increased iNOS activity means increased demand for arginine. Recent studies have shown that sustained availability of high levels of arginine is required not only as the substrate for iNOS but also for enhanced synthesis of iNOS protein at the level of mRNA translation (Lee, J. et al., "Translational control of inducible nitric oxide synthase expression by arginine can explain the arginine paradox," (2003) *Proc. Natl. Acad. Sci. USA* 100:4843-4846; El-Gayar, S. et al., "Translational control of inducible nitric oxide synthase by IL13 and arginine availability in inflammatory macrophages," (2003) *J. Immunol.* 171:4561-4568). The mechanism by which this increased demand for arginine is met in malignant tissues remains unknown.

Transport of arginine into mammalian cells is mediated by several amino acid transport systems (Ganapathy, V. et al., "Intestinal transport of peptides and amino acids," (2001) In *Current Topics in Membranes*, K. E. Barrett and M. Donowitz, editors, Academic Press, New York USA 379-412; Ganapathy, V. et al., "Protein digestion and assimilation (2003) In *Textbook of Gastroenterology*, T. Yamada, editor, Lipincott Williams & Wilkins, Philadelphia, USA 438-448; Ganapathy, V. et al., "Cellular uptake of amino acids: system and regulation," (2004) in *Metabolic and Therapeutic Aspects of Amino Acids in Clinical Nutrition*, L. A. Cynober, editor, CRC Press, Boca Raton, USA 63-78). These include $y^+$, $y^+L$, $b^{0,+}$, and $B^{0,+}$. Of these, only system $B^{0,+}$ is capable of mediating arginine entry into cells in a $Na^+/Cl^-$-coupled manner whereas the other transporters facilitate arginine entry into cells only by a membrane potential-dependent mechanism. The transporter responsible for system $B^{0,+}$ has been identified at the molecular level (Sloan, J. L. and Mager, S., "Cloning and functional expression of a human $Na^+$ and $Cl^-$-dependent neutral and cationic amino acid transporter (B(0+))," (1999) *J. Biol. Chem.* 274:23740-23745; Nakanishi, T. et al., "$Na^+$- and $Cl^-$-coupled active transport of carnitine by the amino acid transporter $ATB^{0,+}$ from mouse colon expressed in HRPE cells and *Xenopus* oocytes," (2001) *J. Physiol.* 532: 297-304). It is known as $ATB^{0,+}$ (amino acid transporter $B^{0,+}$). Because of the energization of $ATB^{0,+}$ by three different driving forces ($Na^+$ gradient, $Cl^-$ gradient, and membrane potential), this transporter has the ability to concentrate arginine inside the cells several-fold higher than in the extracellular medium. The gene coding for this transporter is located on human chromosome Xq34-q24 (Sloan, J. L. and Mager, S., "Cloning and functional expression of a human $Na^+$ and $Cl^-$-dependent neutral and cationic amino acid transporter B(0+))," (1999) *J. Biol. Chem.* 274:23740-23745).

Previous studies of mechanisms of arginine delivery in cancer cells have so far focused on transporters other than $ATB^{0,+}$ (Inoue, Y. et al., "Enhanced hepatic amino acid transport in tumor-bearing rats is partially blocked by antibody to tumor necrosis factor," (1995) *Cancer Res.* 55:3525-3530; Cendan, J. C. et al., "Characterization and growth factor stimulation of L-arginine transport in a human colon cancer cell line," (1995) *Ann. Surg. Oncol.* 2:257-265). Since these $Na^+/Cl^-$-independent transporters are not highly concentrative, they may not be ideally suited to meet the extraordinary demands of cancer cells for arginine to feed into the iNOS-mediated NO synthetic pathway. Therefore, the unique ability of ATB$^{0,+}$ to concentrate arginine inside the cells makes this transporter ideal to be associated with cancer for delivering arginine to iNOS and hence for generating markedly high levels of NO in cancer cells. This was tested by comparing the expression of ATB$^{0,+}$ mRNA and protein between paired normal and cancer tissues harvested from colectomy specimens of patients with colorectal cancer. These studies show that in each of the patients examined, the expression of ATB$^{0,+}$ is upregulated in colon cancer. In addition, the upregulation of ATB$^{0,+}$ is also detected in liver and lymph node metastases from colonic primaries.

Methods

Patients. This study received the Medical College of Georgia institutional review board's approval. Patients were recruited from the adult general surgery services at the Medical College of Georgia after obtaining their informed consent. These patients had been scheduled for elective surgical removal of their disease prior to being approached for participation in this study. Ten adult patients with histopathologically-confirmed colorectal adenocarcinoma, without polyposis or a history of prior chemoradiation, and two adult patients with hepatic metastasis from colonic primaries were included in this study. One of the patients with hepatic metastasis also had lymph node involvement.

Tissue collection and processing. Normal colorectal epithelium, grossly free of cancer, and tissue from the luminal surface of the colorectal cancers were harvested from the freshly resected surgical specimen of each patient in the operating room. The histopathology of all specimens was confirmed by a pathologist as soon as they were harvested. Portions of the tissue (0.3 to 0.5 g from each site) from eleven patients were immediately processed for total RNA extraction using TRIzol® reagent (Invitrogen Life Technologies, Carlsbad, Calif., USA) according to the manufacturers instructions. Tissues from each site were also fixed by immersion in neutral buffered formalin for immunohistochemical studies. Tissues from the single patient with hepatic and lymph node metastases were collected in neutral buffered formalin for immunohistochemistry alone.

Semi-quantitative RT-PCR. Total RNA was denatured at 70° C. for 10 min and at 4° C. for 5 min in a GeneAmp PCR System 9700 thermocycler (PerkinElmer Life and Analytical Sciences, Shelton, CT, USA) in the presence of oligo-dT and random hexamers (Promega Corporation, Madison, WI, USA). Reverse transcription was done using the Maloney murine leukemia virus-reverse transcriptase (Promegal) at 42° C. for 60 min, followed by 10 cycles of 65° C. for 50 sec and 42° C. for 5 min. Incubating at 95° C. for 5 min inactivated the reverse transcriptase. The PCR primers for human ATB$^{0,+}$ and iNOS were designed based on published sequences (GenBank accession numbers: AF_151978 and NM_153292, respectively). The primers for ATB$^{0,+}$ were: 5'GAAGG AGAAAGTGTCGGCTTCA-3' (sense) (SEQ ID NO.1) and 5'-TACCACCTTGCCAGACGATTTG-3' (antisense) (SEQ ID NO:2). The expected size of the amplicon is 754 bp. These primers encompass a region within the sequence coding for the protein and therefore the expected RT-PCR product is likely to represent the long transcript (4.5 kb) as well as the short transcript (2 kb) of human ATB$^{0,+}$ (J.L. Sloan, S. Mager "Cloning and functional expression of a human Na$^{+-\,and\,Cl-}$dependent neutral and cationic amino acid transporter B$^{0,+}$," (1999) *J Biol. Chem.* 274:23740-23745). The iNOS primers were: 5'-CTGGCCAGGGTGGAAGCG-GTAACA-3' (sense) (SEQ ID NO:3) and 5'-CACCACCAA-CAGCAGCCGTTCCTC-3' (antisense) (SEQ ID NO:4). The expected size of the amplicon is 1281 bp. The primers for SNAT4 were: 5'-CCAGATAGCTACATCGGGATA-3' (sense) (SEQ ID NO:5) and 5'-CAGGTAGAGGGCAGGG-TATT-3' (antisense) (SEQ ID NO:6). These primers were based on the published sequence for human SNAT4 (GenBank accession no. NM_018018) and the expected size of the amplicon is 688 bp. The PCR cycle number was determined such that the PCR amplification occurred within the linear range. As an internal control, 18S rRNA was amplified with a primer-competimer combination from Quantum-RNA™ Universal 18S rRNA Internal Standards Kit (Ambion Inc, Austin, TX, USA) according to the manufacturer's instructions for semi-quantitative RT-PCR. This kit supplies both 18S primers and competimers, the latter of which have been modified to block extension by DNA polymerase and thus reduce the efficiency of PCR amplification of the 18S cDNA. The optimum primer-competimer ratio was determined by serial dilutions such that 18S cDNA was amplified at a level similar to that of the target of interest. By thus equalizing the amplification efficiency of 18S and the target gene, multiplex PCR could be performed without competitive interference for primers limiting the quanitification process. PCR with each pair of normal and cancer template cDNA was done using a cocktail of 18S rRNA primer-competimer (in the ratio 1:9), 10x PCR buffer with Mg$^{2+}$, dNTP, forward and reverse primers, and TaKaRa Taq polymerase (Takara Bio Inc, Shiga, Otsu, Japan). Aliquots from the master mixture were added to cDNA from normal tissue and the corresponding cancer tissue. Negative controls were processed under identical conditions but without the addition of reverse transcriptase. The PCR protocol consisted of 3 min at 94° C. followed by 30 cycles of denaturing at 94° C. for 60 sec, annealing at 58° C. for 60 sec for ATB$^{0,+}$ and 62.5° C. for 60 sec for iNOS, and extension at 72° C. for 60 sec, followed by a single run of 72° C. for 10 min. The resultant multiplex PCR products (18S and either ATB$^{0,+}$ or iNOS) were run in agarose gels, stained with ethidium bromide and the intensities of the bands measured by densitometry using a SpectraImager 5000 Imaging system and AlphaEase 32-bit software (Alpha Innotech, San Leandro, CA, USA). The expression levels of ATB$^{0,+}$ and iNOS were normalized to the corresponding 18S rRNA, and the relative expression of the target genes in colon cancer compared to normal tissue from the same patient was determined. The RT-PCR products for ATB$^{0,+}$ and iNOS were sequenced to confirm their molecular identity. These RT-PCR products were then used as probes for Northern blot analysis.

Northern Blot Analysis. Total RNA was used to prepare poly(A)+ RNA using oligo(dT)-microbeads (Miltenyi Biotec Inc., Auburn, Calif., USA). 5 µg of poly(A)$^+$ RNA from each specimen was then size-fractionated and transferred to Hybond N$^+$ nylon membrane (Amersham Biosciences, Piscataway, N.J., USA) according to the manufacturer's instructions. The nylon membrane was pre-hybridized for three hours at 42° C. with ULTRA-hyb hybridization solution (Ambion Inc., Austin, Tex., USA) followed by hybridization for 18 hours in the same buffer containing a $^{32}$P-labeled cDNA probe specific for human ATB$^{0,+}$ or iNOS. The cDNA probes were labeled by random priming using the Ready-to-go Oligo labeling beads (Amersham Biosciences) and α[$^{32}$P]-dCTP (Amersham Biosciences). The membrane was washed twice at 60° C. for thirty minutes apiece in a low stringency buffer [2× saline-sodium citrate (SSC), 0.5% w/v sodium dodecylsulfate (SDS)] and then washed twice in a high stringency buffer (0.2×SSC, 0.5% SDS). The membrane was exposed to Biomax-MS film (Eastman Kodak Company, Rochester, N.Y., USA) for 48 hours (ATB$^{0,+}$) or 24 hours (iNOS) at −80° C. mRNA levels were determined by densitometry using SpectraImager 5000 Imaging system and AlphaEase 32-bit software (Alpha Innotech, San Leandro, Calif., USA). After quantifying the hybridization signal by densitometry, the membrane was stripped and reprobed with a $^{32}$P-labeled cDNA probe specific for β-actin as an internal control. The hybridization signals were expressed as a ratio of the target mRNA signal to the β-actin mRNA signal. The ATB$^{0,+}$-specific cDNA fragment resulting from the PCR represents a part of the region coding for the protein and this fragment overlaps with the probe used by Sloan and Mager, supra, which detected two different splice variants of ATB$^{0,+}$ transcripts in human tissues.

Immunohistochemistry. Tissue samples obtained for immunohistochemistry were fixed in 10% neutral-buffered formalin and embedded in paraffin. Sections (5 μm), cut from the paraffin block, were deparaffinized in xylene and rehydrated through graded alcohols. Normal and cancer tissue from the same patient were mounted on the same slide to ensure identical conditions. Endogenous peroxidase activity was quenched with methanol/$H_2O_2$. Immunostaining was performed using rabbit polyclonal antibodies specific for ATB$^{0,+}$ (Sloan, J. L. et al, "Expression of the amino acid transporter ATB$^{0,+}$ in lung: possible role in luminal protein removal," (2003) *Am. J. Physiol.* 284:L39-49), mouse monoclonal anti-NOS antibody (Santa Cruz Biotechnology, Inc., Santa Cruz, Calif., USA), and rabbit polyclonal anti-nitrotyrosine antibody (Upstate Cell Signaling Solutions, Lake Placid, N.Y.). Nitrosylated tyrosine residues are reflective of in situ NO levels. Immunohistochemistry was performed using the Labeled Streptavidin-Biotin 2 (LSAB2) detection system (DAKO Corp., Carpenteria, Calif.). 3,3-diaminobenzidine tetrahydrochloride was used as the chromogen. Negative controls unexposed to primary antibodies were processed in the same manner.

Statistical Analysis. RT-PCR was repeated at least four times under identical conditions with each of the 11 pairs of specimens. The log of the ratio of relative expression by RT-PCR and Northern blotting was analyzed using a linear mixed model that included subject and gel dates as random effects. Means and standard errors were calculated, and t-tests used as appropriate.

Results

Patient Information. Ten adult patients with colorectal cancer, one patient (GM12) with a hepatic metastasis from a previously resected colon cancer, and one patient with liver and lymph node metastases (GM38) were enrolled in the study (Table 1). The serial numbers were allocated consecutively when the patient consented to participation in this study. The samples in this study are not numbered consecutively, though these samples were collected consecutively, because the tissue bank includes patients with diagnoses other than colorectal cancer, whose tissue was collected for other studies. Factors like postponement or cancellation of surgery after enrollment in the study, inadequate tissue upon resection, a delay or change in diagnosis after final histopathology, or a history of confounding factors (prior chemoradiation, polyposis, etc.) also contributed to the non-consecutive serial numbers.

There were eight African-Americans and four Caucasians, seven females and five males. The average age was 62 years (range 37-82 years). Final pathology reports demonstrated that a range of poor, moderate and well-differentiated adenocarcinomas involving all areas of the colon, from the ascending colon to the rectum, were included in the present investigation. All four stages of colorectal cancer, according to the TNM (Tumor, Node, Metastasis) classification developed by the American Joint Committee for Cancer Staging and End Results Reporting and approved by the International Union Against Cancer, were present. The patient with a hepatic metastasis from a previously resected colonic primary (GM12) had had the colonic resection done in another institute, and colonic tissue was not available for testing. In this case, normal and malignant hepatic tissue from the resected hepatic specimen was harvested and compared. Histopathology of the resected specimens confirmed normal hepatic tissue and hepatic metastasis from a mucinous colonic adenocarcinoma primary. The patient with lymph nodal and hepatic metastases (GM38) yielded specimens from the normal colon, the primary tumor as well as both the metastatic sites for immunohistochemistry alone.

Expression of ATB$^{0,+}$ and iNOS mRNA in normal and cancer tissue. Semi-quantitative RT-PCR for the analysis of mRNA levels for ATB$^{0,+}$ (FIG. 1A) and iNOS (FIG. 1B) was performed and expression in normal colorectal epithelium and normal hepatic tissue was compared to that of tissue from the luminal surface of colorectal cancer or the metastasis, respectively, from the same patient, standardizing each mRNA with 18S rRNA. The size of the ATB$^{0,+}$-specific RT-PCR product was 754 bp. The molecular identity of the product was established by sequencing. Normal colon and liver had minimal but detectable, ATB$^{0,+}$ mRNA expression. The expression in cancer consistently showed several-fold increase over the expression in the corresponding normal tissue in all eleven patients (colonic tissues from ten patients and liver tissue from one patient). Overall the ten patients with colorectal cancer showed a 22.9±3.0-fold increase in ATB$^{0,+}$ mRNA expression over normal tissue as assessed by RT-PCR ($p<0.0001$). Hepatic metastasis from a colonic primary (GM12) showed a 28.6-fold increase in ATB$^{0,+}$ mRNA expression compared to normal hepatic tissue.

The size of the iNOS-specific RT-PCR product was 1281 bp, and the molecular identity of this product was also confirmed by sequencing. The expression in cancer consistently showed an increase over the expression in the corresponding normal tissue in all eleven patients. Overall, the ten patients with colorectal cancer showed a 5.2±1.1-fold increase in the expression of iNOS mRNA over normal tissue as assessed by RT-PCR ($p<0.002$). Hepatic metastasis from a colonic primary (GM12) showed a 9.7-fold increase in iNOS mRNA expression compared to normal hepatic tissue.

Figure 2:
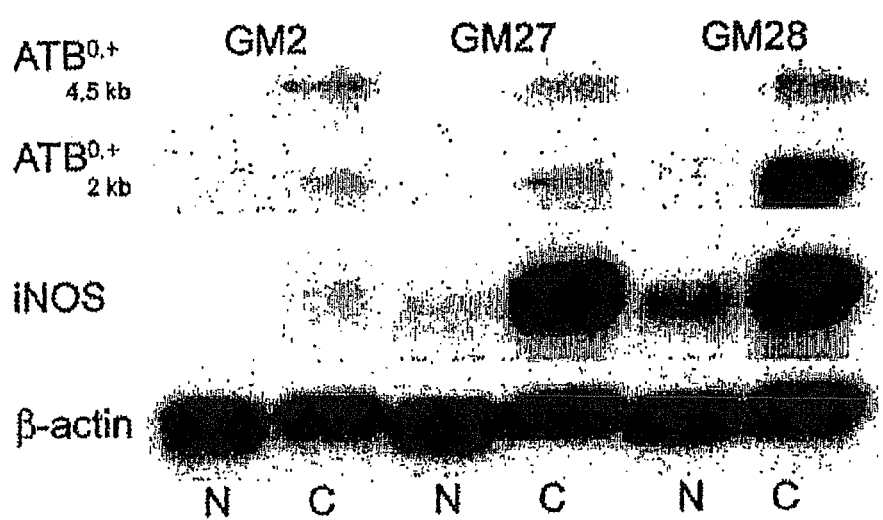
FIG. 2. Northern blot analysis of $ATB^{0,+}$ and iNOS mRNA expression in normal colon (N) and colorectal cancer (C) tissue. The blot was hybridized sequentially under high stringency conditions with [$^{32}$P]-labeled cDNA probes specific for $ATB^{0,+}$, iNOS, and β-actin. $ATB^{0,+}$ has two transcripts, 4.5 kb and 2 kb in size, as detected by the cDNA probe representing a part of the coding region. The 4.5 kb transcript shows an overall 19.8±5.1-fold increase in cancer. The 2 kb $ATB^{0,+}$ transcript shows a corresponding 5.8±1.9-fold increase in colorectal cancer. iNOS shows an overall 5.2±2-fold increase in colorectal cancer. The patients' serial numbers are listed above the blots. N:Normal colorectal epithelium, C:Colorectal cancer.

Semi-quantitative RT-PCR results were confirmed by Northern blot analysis, using paired samples from three patients (FIG. 2). As reported by Sloan, J. L. and Mager, S., "Cloning and functional expression of a human Na$^+$ and Cl$^-$-dependent neutral and cationic amino acid transporter B(0+)," (1999) *J. Biol. Chem.* 274:23740-23745, ATB$^{0,+}$ had two different transcripts (2 kb and 4.5 kb in size) arising from alternative splicing. The steady-state levels of both transcripts increased in cancer. After normalization with β-actin mRNA levels, the larger transcript showed an increase of 19.8±5-fold in cancer compared to normal. The corresponding value for the shorter transcript was a 5.8±1.9-fold. Similarly, the semi-quantitative RT-PCR results for iNOS expression were also confirmed by Northern blot analysis. The increase in iNOS mRNA expression was 5.2±2-fold in cancer compared to normal.

There was no statistically significant correlation between the steady-state levels of ATB$^{0,+}$ mRNA and iNOS mRNA in cancer tissue or in normal tissue. Similarly, there was no statistical correlation between the increases in the levels of ATB$^{0,+}$ mRNA and iNOS mRNA and the location, stage or grade of colorectal cancer. There was also no significant correlation of ATB$^{0,+}$ mRNA and iNOS mRNA expression with age, sex, or race of the patient, or location of the cancer. In the cancer specimens as well as in the metastasis specimens, the sites of increased expression of iNOS protein were close to the apical and basolateral membranes of epithelial cells.

Expression of SNAT4. SNAT4 is also a transporter, for arginine and this transporter is energized by a transmembrane electrochemical Na$^+$ gradient (M. Sugawara, et al., "Structure and function of ATA3, a new subtype of amino acid transport system A, primarily expressed in the liver and skeletal muscle," (2000) *Biochim. Biophys. Acta* 1509:7-13; T. Hatanaka, et al., "Evidence for the transport of neutral as well as cationic amino acids by ATA3, a novel and liver-specific subtype of amino acid transport system A"(2001) *Biochim. Biophys. Acta* 1510:10-17). Since SNAT4 has the ability to accumulate arginine inside the cells in a Na$^+$-coupled manner, we were interested to find out if the expression of this transporter is altered in colorectal cancer. We therefore compared the steady-state levels of SNAT4 mRNA in control and cancer samples by semi-quantitative RT-PCR (data not shown). With four different paired samples of colorectal cancer (GM1, GM2, GM6, and GM9) and one paired sample of liver metastasis (GM12), we found that the steady-state levels of SNAT4 mRNA did not change in three samples of colorectal cancer (GM1, GM6, and GM9) and that the levels increased in one sample (GM2). In the case of liver metastasis, the steady-state levels of SNAT4 mRNA decreased significantly in cancer compared to normal tissue. Thus, the changes in the expression levels of SNAT4 were not uniform in colorectal cancer.

Figure 3:
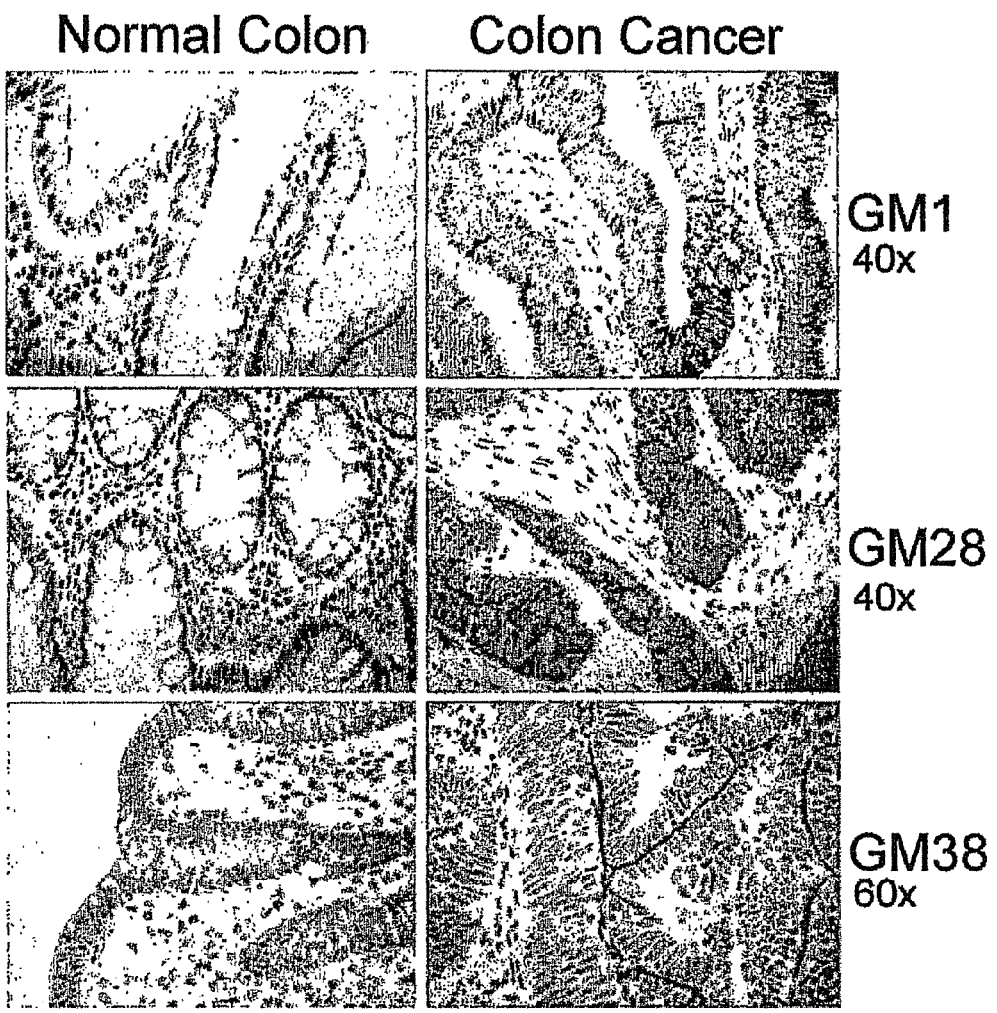
FIG. 3. Immunohistochemical analysis of $ATB^{0,+}$ protein expression in normal colon and colon cancer using rabbit polyclonal antibodies specific for $ATB^{0,+}$. $ATB^{0,+}$ protein expression is increased in cancer by immunohistochemistry, as shown in representative slides from three patients. For each patient, negative controls unexposed to primary antibody are shown in the first column. Normal colonic epithelium, shown in the middle column, demonstrates minimal ATB$^{0,+}$ protein in the brush border. In the third column, cancer tissue from each patient shows a marked increase in ATB$^{0,+}$ protein expression, specifically in the apical and basal regions of the epithelial cells. ATB$^{0,+}$ protein is detectable in the brush border of normal colonic epithelium. In cancer tissue from the same patient, ATB$^{0,+}$ expression is markedly increased in the glandular elements, and specifically in the apical and basal regions of the cells.
Figure 4A:
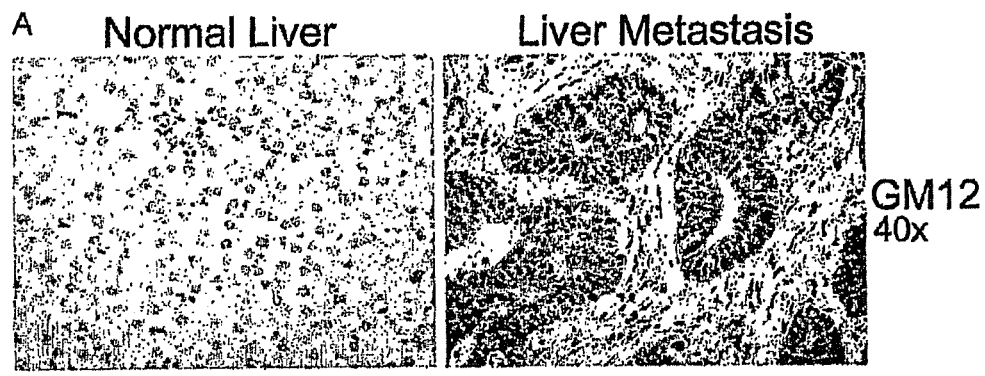
In FIG. 4A, ATB$^{0,+}$ protein is not detected in normal liver tissue harvested from an area non-adjacent to the metastasis. The epithelial cells of the metastasis show intense staining for ATB$^{0,+}$, while the stromal tissue shows none. The cellular distribution of ATB$^{0,+}$ in hepatic metastasis is similar to that in primary colon cancer cells, with localization to the apical and basolateral regions of the cell membrane.

Expression of ATB$^{0,+}$ protein. Representative immunohistochemical stains for ATB$^{0,+}$ protein in normal and cancer colon tissues from three patients are shown in FIG. 3. Normal colonic epithelium from all three patients showed low, but detectable, expression of ATB$^{0,+}$ at the apical membrane as well as in the cytoplasm. The cancer tissue from the corresponding patients showed markedly elevated levels of ATB$^{0,+}$ protein. The increased expression in cancer specimens was evident especially in the apical and basolateral membranes of colonic epithelial cells. Similarly, normal liver tissue far removed from the metastasis expressed very low levels of ATB$^{0,+}$ (FIG. 4A), but the expression of the transporter protein was robust in the liver metastasis itself. The distribution pattern of ATB$^{0,+}$ in the liver metastasis was similar to that seen in the primary colon cancer with increased prominence in the apical membrane and in the basolateral membrane compared to other regions of the epithelium.

Figure 4B:
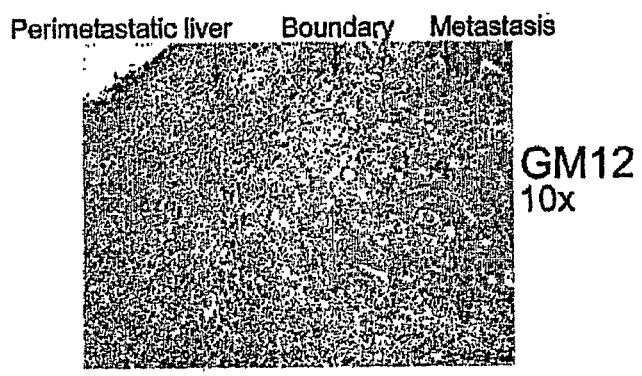
In FIG. 4B, histologically normal perimetastatic liver showed increased expression of ATB$^{0,+}$.
Figure 4C:
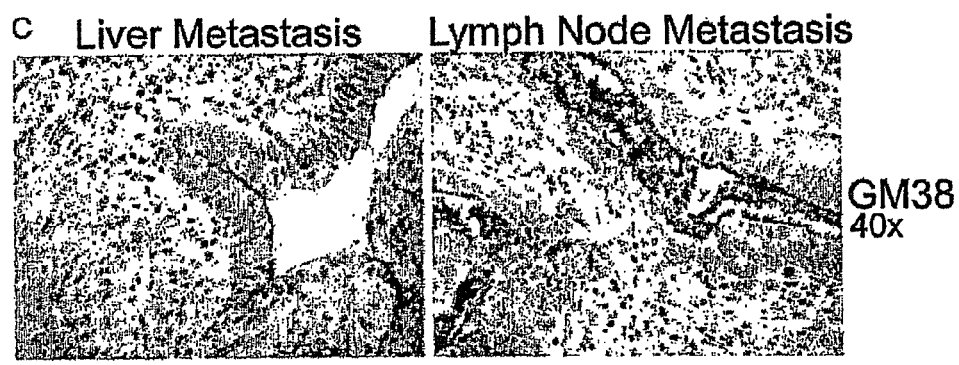
In FIG. 4C, increased ATB$^{0,+}$ protein expression is also shown in the liver and lymph node metastases from another patient.

Interestingly, the increased expression of ATB$^{0,+}$ protein was seen not only in the liver metastasis but also in the immediately adjoining perimetastatic hepatic tissue that was microscopically free of cancer (FIG. 4B). This metastasis-free, histologically normal, perimetastatic hepatic tissue expressed much higher levels of ATB$^{0,+}$ protein than normal hepatic tissue from a site far removed from the metastasis. The boundary of compressed tissue between the metastasis and the perimetastatic liver did not show expression of ATB$^{0,+}$ protein. Elevated levels of ATB$^{0,+}$ protein were also demonstrated in liver and lymph node metastases (FIG. 4C) in another patient (GM38), where the distribution pattern of ATB$^{0,+}$ protein was similar to that seen in the primary cancer.

Figure 5A:
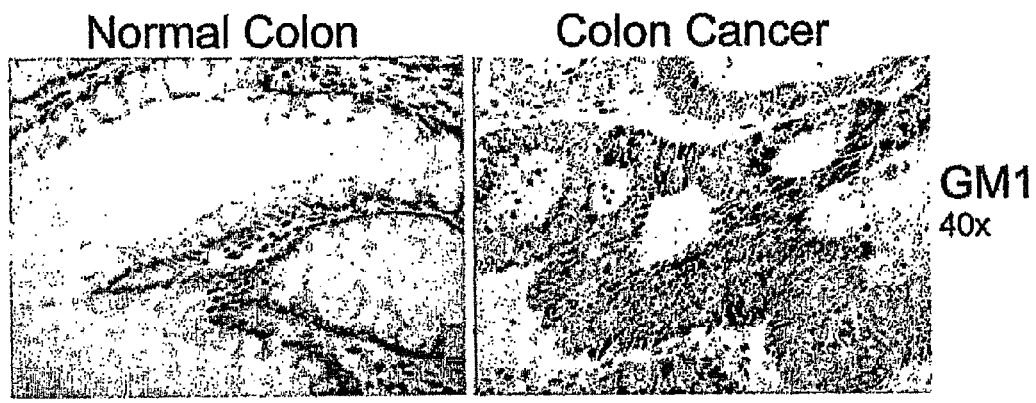
FIG. 5. Immunohistochemical analysis of iNOS protein expression in colon cancer and hepatic metastasis using a mouse monoclonal antibody specific for iNOS. Sections of normal colon and cancer tissue (FIG. 5A) were stained for iNOS protein. Similarly, sections of normal liver and metastasis of liver cancer (FIG. 5B) were also stained for iNOS. Negative controls were performed by omitting the primary antibody. Omission of the primary antibody resulted in undetectable signals (data not shown). The expression of iNOS is increased in colon cancer and hepatic metastasis and its distribution mimics that of ATB$^{0,+}$, with expression localized near the apical and basolateral membranes.
Figure 5B:
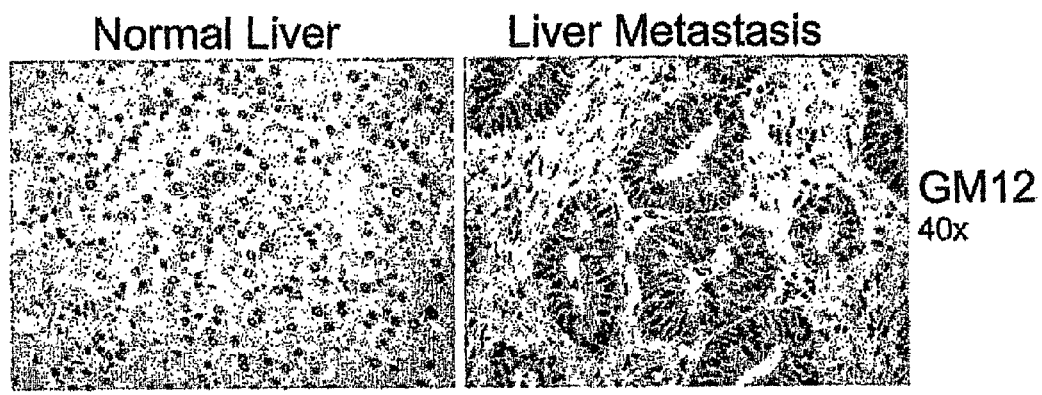

Expression of iNOS protein. Normal colonic epithelium from all patients expressed detectable levels of iNOS, staining with a diffuse, blush-like pattern. The cancer tissue from each subject showed increased, focally intense iNOS staining with an uneven distribution in the cytoplasm of the tumor cells. Representative immunohistochemical stains from one patient (GUN) are shown in FIG. 5A. Normal liver showed very little iNOS protein expression (FIG. 5B), but the hepatic metastasis demonstrated intense staining for iNOS protein with an intracellular distribution similar to the pattern seen in the colon primary cancer. In the cancer specimens as well as in the metastasis specimens, the sites of increased expression of iNOS protein were close to the apical and basolateral membranes of epithelial cells.

Figure 6:
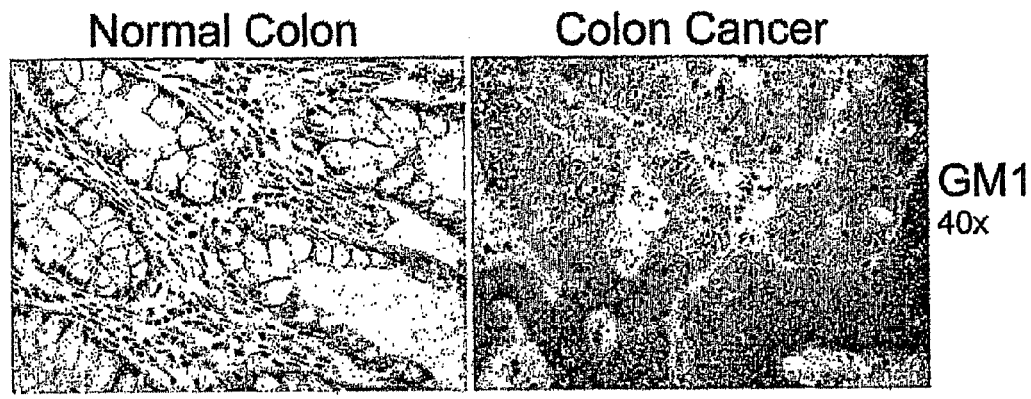
FIG. 6. Immunohistochemical analysis of nitrotyrosylated proteins in colon cancer. The relative levels of nitrotyrosylated proteins in control colon tissue and corresponding cancer tissue were analyzed and shown to be increased by immunostaining using a polyclonal antibody specific for nitrotyrosine. Negative controls were performed without the addition of the primary antibody. Omission of the primary antibody failed to give any detectable signals (data not shown).
Figure 7:
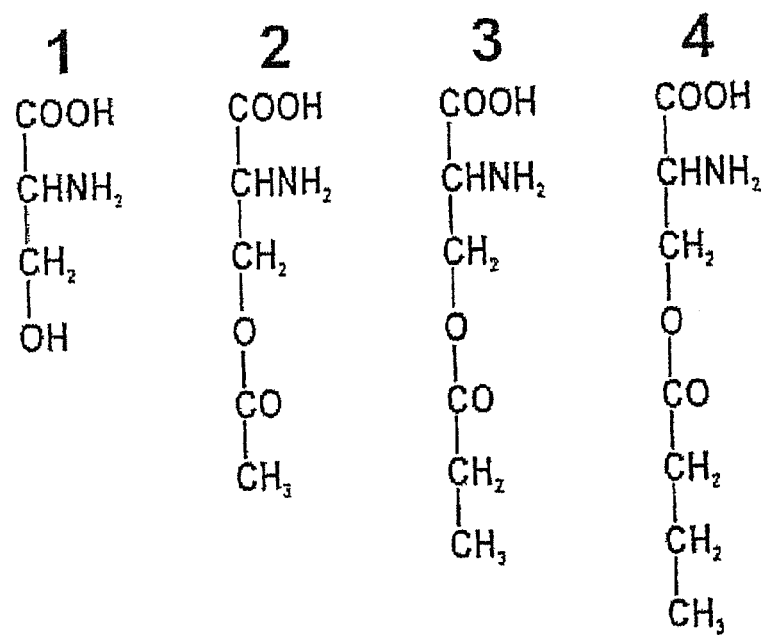
FIG. 7. Structures of L-serine (1) and its esters of acetate (2), propionate (3), and butyrate (4).

NO levels in cancer compared to normal tissue. Immunohistochemical analysis with an anti-nitrotyrosine antibody demonstrated increased staining in cancer tissue compared to normal in all patients. A representative immunostain from one patient (GM1) is shown (FIG. 6). The nitrotyrosylated tyrosine residues were present throughout the cytoplasm in a diffuse pattern in nearly all of the malignant epithelial cells.

TABLE 1

Patient Information

| Patient | Age (yrs) | Race | Sex | Histopathologic grading | TNM | Stage |
|---------|-----------|------|-----|-------------------------|-----|-------|
| GM1 | 78 | B | M | Well-differentiated sigmoid adenocarcinoma | T4N0Mx | II |
| GM2 | 54 | B | F | Moderately to well-differentiated sigmoid adenocarcinoma | T3N0Mx | II |
| GM6 | 53 | W | F | Moderately to well-differentiated rectal adenocarcinoma | T3N1M1 | IV |
| GM9 | 50 | B | F | Moderately to well-differentiated ascending colon adenocarcinoma | T1N0M1 | IV |
| GM12 | 54 | W | F | Hepatic metastasis from mucinous adenocarcinoma colon primary | TxNxM1 | IV |
| GM25 | 73 | W | F | Moderately to well-differentiated sigmoid colon adenocarcinoma | T3N0Mx | II |
| GM27 | 37 | W | M | Poor to moderately-differentiated ascending colon adenocarcinoma | T3N0Mx | II |
| GM28 | 73 | B | M | Moderately-differentiated descending colon adenocarcinoma | T3N1Mx | IIIb |
| GM29 | 56 | B | M | Moderately to well-differentiated ascending colon adenocarcinoma | T2N2Mx | IIIc |
| GM30 | 77 | B | F | Moderately-differentiated ascending colon adenocarcinoma | T2N0Mx | I |
| GM36 | 82 | B | M | Moderately-differentiated transverse colon adenocarcinoma | T1N0Mx | I |
| GM38 | 60 | B | F | Moderately-differentiated ascending colon adenocarcinoma | T4N1M1 | IV |

TNM, Tumor, Node, Metastasis classification of cancer stage, developed by the American Joint Committee for Cancer Staging and End Results Reporting and approved by the International Union Against Cancer.

Example 2

Transport of Short-chain Fatty Acids in the Form of L-serine Esters Via Amino Acid Transporter ATB$^{0,+}$ The results of Example 1 prompted evaluation of the utility of the ATB$^{0,+}$ transporter as a potential candidate for delivering the amino acid prodrug of butyrate, namely O-butyryl-L- serine instead of butyrate in cancers. This approach was evaluated as a drug delivery mechanism by examining the interaction of ATB$^{0,+}$ with a variety of α-carboxyl esters of L-serine, showing that the SCFAs esters of L-serine are indeed transportable by the ATB$^{0,+}$ transporter.

Materials and Methods $^3$H-glycine was purchased from NEN Life Science Products, Boston, Mass., USA. L-serine, O-acetyl-L-serine and TLC plates (Cat #T-6520) were purchased from SIGMA Chemical Company, St. Louis, Mo., US. Ninhydrin was purchased from Pierce Chemical Company, Rockford, Ill. O-propionyl-L-serine and O-butyryl-L-serine were synthesized by Peakdale Molecular Ltd (Peakdale Science Park, Sheffield Road, Chapel-en-le-Frith, High Peak, SK23 OPG, UK). All other chemicals used were of analytical grade.

Functional Expression of ATB$^{0,+}$ in HRPE Cells:

Cloned rat ATB$^{0,+}$ was functionally expressed in the human retinal pigment epithelial (HRPE) cell line using the vaccinia virus functional expression technique (Wu, X. et al., (1998) *Biochem. Biophys. Res. Commun.* 246:589-595; Wu, X. et al., (1999) *J. Pharm. and Exper. Therapeutic* 290:1482-1492) in the analysis of its role in the transport of amino acids and amino acid-based prodrugs. Glycine was used as the substrate for ATB$^{0,+}$ because previous studies (Hatanaka, T. et al., (2001) *J. Clin. Invest.* 107(8):1035-1043; Hatanaka, T. et al., (2002) *Biochem. Biophys. Res. Commun*, 291:291-295; Nakanishi, T. et al., (2001) J. *Physiol.* 532(Pt2):297-304) have shown that glycine transport in HRPE cells was induced more than 30-fold in cells transfected without ATB$^{0,+}$ in cDNA-transfected HRPE cells. Transport of glycine in cDNA-transfected cells was measured at 37° C. for 30 minutes. The transport buffer was 25 mM Hepes/Tris (pH 7.5) containing 140 mM NaCl, 5.4 mM KCl, 1.8 mM CaCl$_2$, 0.8 mM MgSO$_4$, and 5 mM glucose. Interaction of L-serine, O-acetyl-L-serine, O-propionyl-L-serine as well as O-butyryl-L-serine with the ATB$^{0,+}$ transporter was accessed by monitoring the ability of these compounds to compete with glycine uptake for ATB$^{0,+}$-mediated transport. Transport measurements were made in parallel in vector-transfected and in ATB$^{0,+}$ cDNA-transfected HRPE cells to account for transport activity of endogenous L-serine or its esters. The ATB$^{0,+}$-specific transport of L-serine and its esters was determined by subtracting the transport values measured in vector-transfected cells from the transport values measured in cDNA-transfected cells.

Amino Acid Analysis:

Amino acid analysis was carried out by using Beckman High Performance Amino Acid Analyzers (7300 Series). The procedure was according to the Laboratory Manual (Techniques in Diagnostic Human Biochemical Genetics), Frits A. Hommes (Wiley-Liss, Inc., A. John Wiley & Sons, Inc., New York).

Thin Layer Chromatography:

8 cm×20 cm silica, polyester plates (Cat #T-6520, Sigma) 0.1 mm thick were used. Standard solutions of the L-serine and its SCFA esters (5 mM) were prepared in the uptake buffer and applied with a micropipette. Separation was carried out in a saturated TLC chamber using an n-butanol-acetic acid-water (4:1:1v/v/v) mixture as the mobile phase. After the run was over, the plates were dried in hot air. Detection was carried out by spraying the plates with a 2% ninhydrine solution in acetone and drying at room temperature. Identification of the L-serine or its SCFA α-carboxyl ester was achieved by comparing relative positions.

Data Analysis:

Experiments with HRPE cells were repeated at least three times with three independent transfections and transport measurements made in duplicate in each experiment. Electrophysiological measurements of substrate-induced currents were repeated at least three times with separate oocytes. The data are presented as means±S.E.M. of these replicates. The kinetic parameters, Michaelis constant ($K_t$) and maximal velocity ($V_{max}$) were calculated by fitting the ATB$^{0,+}$-specific transport data to the Michaelis-Menten equation describing a single saturable transport system. Na$^+$ and Cl$^-$-activation kinetics were analyzed by fitting the ATB$^{0,+}$-specific transport data to the Hill equation for the determination of $K_{0.5}$ values for Na$^+$ and Cl$^-$ (concentration of Na$^+$ and Cl$^-$ necessary for half-maximal activation) and the Hill coefficient (nH; the number of Na$^+$ or Cl$^-$ ions involved in the activation process). The kinetics parameters were first determined by non-linear regression methods and subsequently confirmed by linear regression methods using the commercially-available computer program SigmaPlot, version 6.0 (SPSS Inc., Chicago, Ill., US).

Results

Interaction of L-serine, O-acetyl-L-serine, O-propionyl-L-serine and O-butyryl-L-serine with ATB$^{0,+}$ Transporter Expressed in HRPE Cells.

Figure 8:
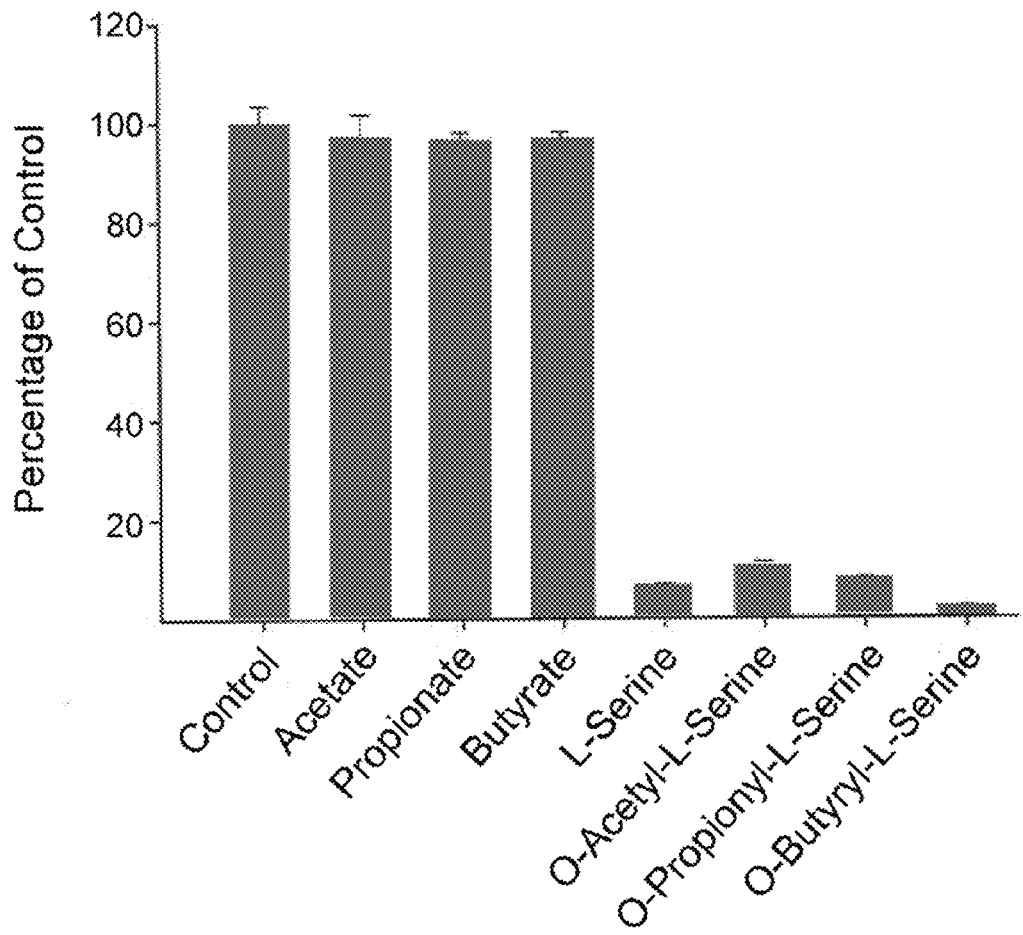
FIG. 8. Inhibition of ATB$^{0,+}$-mediated glycine uptake by short-chain fatty acids and their esters with L-serine. Rat ATB$^{0,+}$ was expressed in mammalian cells and the $^3$H-glycine uptake inhibition studies were conducted in the presence of 5 mM acetate, propionate, butyrate, L-serine, O-acetyl-L-serine, O-propionyl-L-serine and O-butyryl-L-serine.

Serine is a neutral amino acid which is an excellent substrate for ATB$^{0,+}$. Therefore, we first investigated the commercially-available α-carboxyl derivative of serine, O-acetyl-L-serine with cloned rat ATB$^{0,+}$ to check transport of this molecule by ATB$^{0,+}$. As expected, serine at a concentration of 5 mM inhibited ATB$^{0,+}$-mediated glycine transport significantly (>93%) (FIG. 8). Similarly, the α-carboxyl ester of L-serine, O-acetyl-L-serine also inhibited glycine transport to the same extent (~90%). Under similar conditions, sodium acetate, sodium propionate and sodium butyrate did not inhibit glycine transport, which indicates that the acetates, propionates, and butyrate groups are not recognized by the ATB$^{0,+}$ transporter (FIG. 8).

Two other short-chain fatty acid esters of L-serine, namely O-propionyl-L-serine and O-butyryl-L-serine were synthesized, keeping the ester bond at the α-carboxyl group of the serine as in the O-acetyl-L-serine. These short-chain fatty acid esters also inhibited glycine transport significantly, and the inhibition was comparable to that of L-serine (FIG. 8).

Figure 9A:
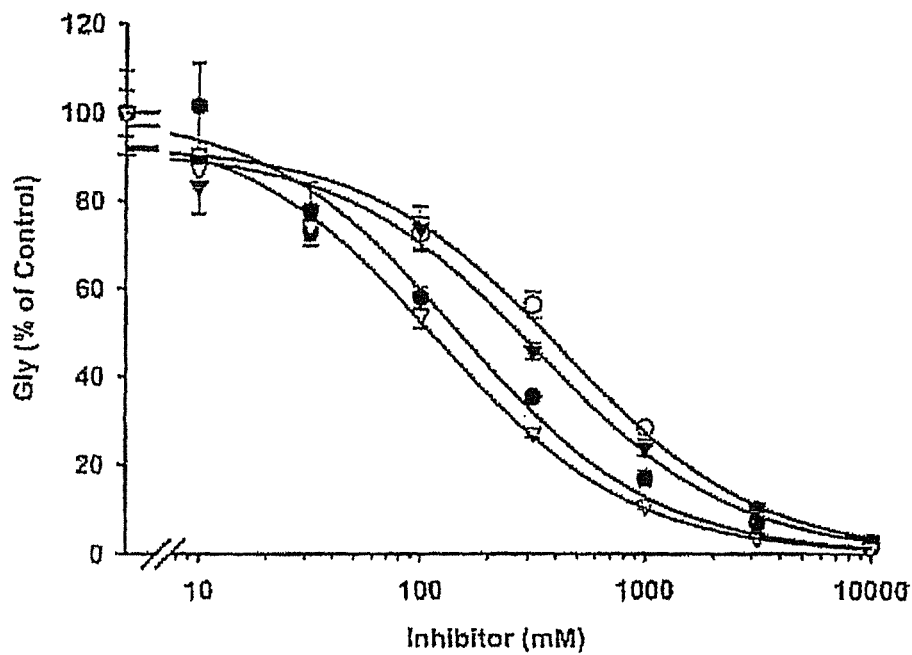
FIG. 9A shows a dose-response relationship for the inhibition of ATB$^{0,+}$-mediated uptake of glycine (10 μM) by L-serine (•), O-acetyl-L-serine (○), O-propionyl-L-serine (▼), and O-butyryl-L-serine (∇). Transport in the absence of inhibitors was taken as 100%.
Figure 9B:
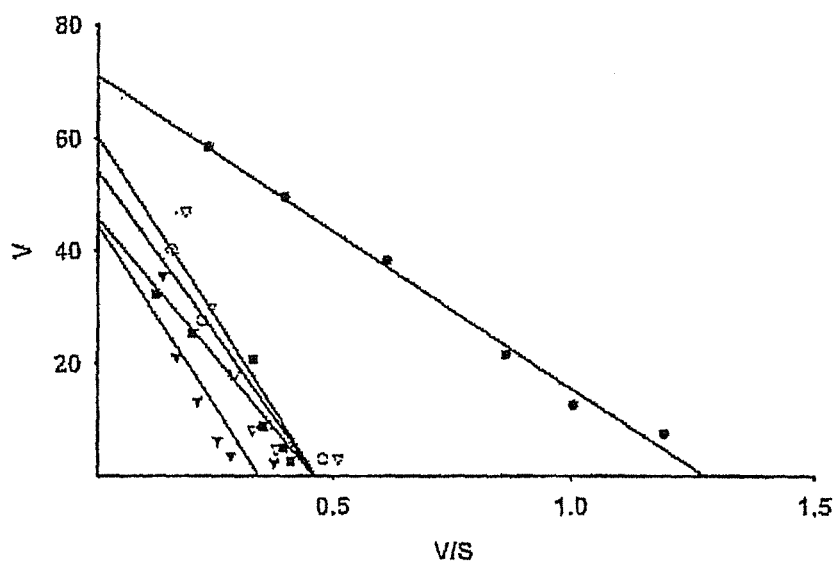
FIG. 9. Kinetic analysis of the interaction of L-serine and its short-chain fatty acid esters with ATB$^{0,+}$. Rat ATB$^{0,+}$ was expressed in Xenopus oocytes heterologously in HRPE cells and its transport function was monitored by the uptake of glycine.

Studies of the dose response relationship for the inhibition of ATB$^{0,+}$-mediated glycine transport by L-serine and the short-chain fatty acids showed IC$_{50}$ values (i.e., concentration of the inhibitor necessary for 50% inhibition) as follows: L-serine, 148±28; O-acetyl-L-serine, 423±72; O-propionyl-L-serine, 332±59; and O-butyryl-L-serine, 118±8 (FIG. 9A). Kinetic analysis revealed that the inhibition caused by the L-serine of its short-chain fatty acid esters was competitive (FIG. 9B). The Michaelis-Menten constant ($K_t$) and the maximal velocity ($V_{max}$) for ATB$^{0,+}$-mediated glycine transport in the absence or in the presence of 5 mM inhibitors is shown in Table 2. The results indicate that the short-chain fatty acid esters of L-serine inhibited ATB$^{0,+}$-mediated glycine transport primarily by reducing substrate affinity.

Interaction of L-serine, O-acetyl-L-serine, O-propionyl-L-serine and O-butyryl-L-serine with ATB$^{0,+}$ in the *X. laevis* Oocyte Expression System.

Figure 10:
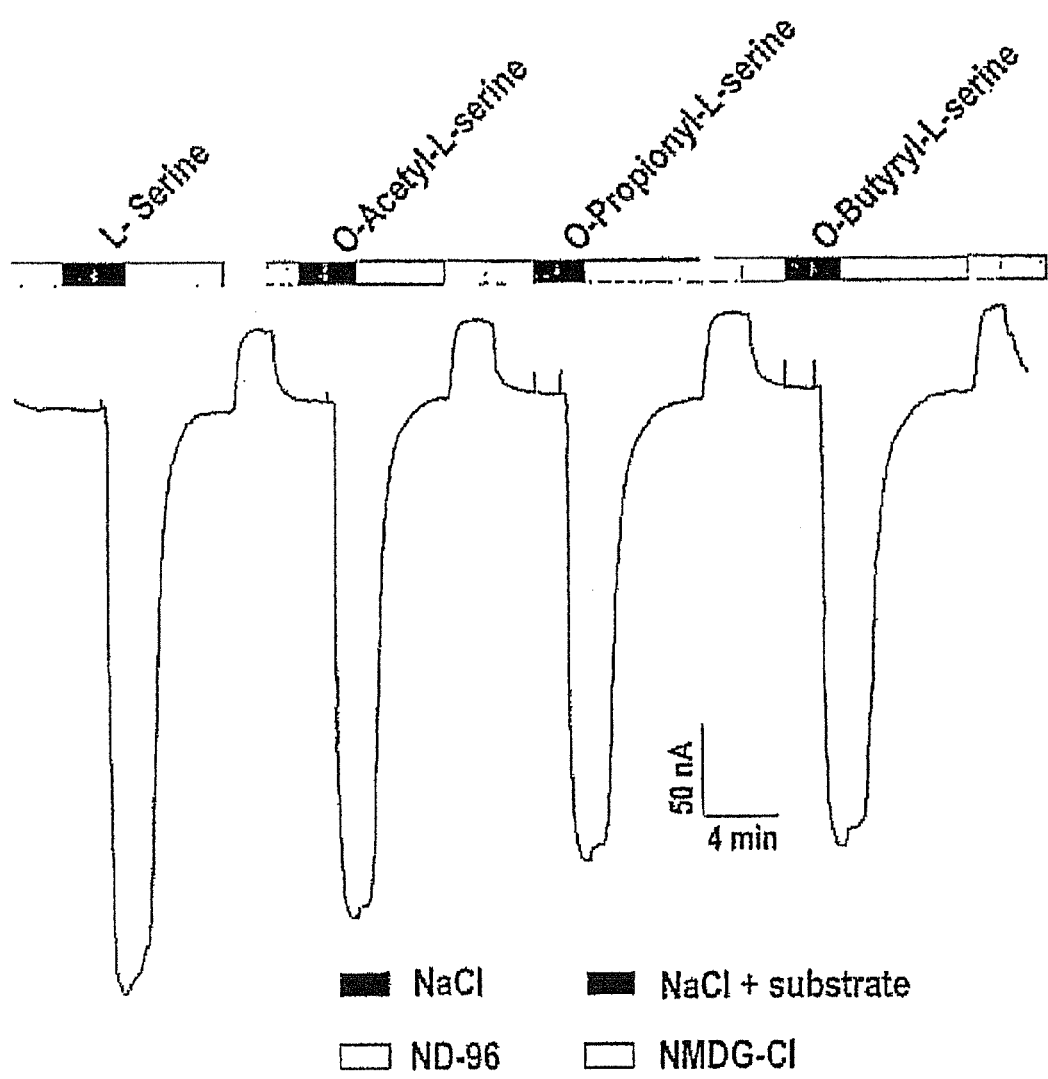
FIG. 10. Transport of L-serine, O-acetyl-L-serine, O-propionyl-L-serine and O-butyryl-L-serine via ATB$^{0,+}$ as assessed by substrate-induced currents in Xenopus oocytes. Rat ATB$^{0,+}$ was expressed in Xenopus oocytes heterologously and the currents induced by L-serine and its derivatives (5 mM) in these oocytes were measured.

The results obtained above with the mammalian cell expression system clearly show that the α-carboxyl esters of neutral amino acid L-serine and its short-chain fatty acid esters interact with ATB$^{0,+}$ as evidenced by their ability to inhibit glycine transport via the ATB$^{0,+}$ transporter. However, these studies do not prove that the amino acid derivatives are actually transported by ATB$^{0,+}$. It was possible that these amino acid derivatives might by competing with the glycine for binding to the substrate-binding site without themselves being actually translocated across the membrane. Therefore, it was necessary to determine whether or not the α-carboxyl esters of neutral amino acids are transportable substrates for ATB$^{0,+}$. For this purpose, we used the *X. laevis* oocyte expression system. Cloned rat ATB$^{0,+}$ was functionally expressed in oocytes by injection of corresponding cRNA, and the transport of substrates via the transporter was monitored by inward currents when the oocytes were exposed to putative substrates under voltage-clamp conditions. Exposure of ATB$^{0,+}$-expressing oocytes to L-serine or its short-chain fatty cid esters O-acetyl-L-serine, O-propionyl-L-serine and O-butyryl-L-serine induced marked inward currents. (FIG. 10). Acetate, propionate and butyrate did not induce detectable current. These data corroborated the finding from the mammalian cell expression studies in which acetate, propionate and butyrate failed to inhibit ATB$^{0,+}$-mediate glycine uptake.

Water-injected oocytes did not show any detectable currents upon exposure to L-serine or its ester derivatives (data not shown). These studies provide clear evidence for the transport of L-serine or its ester derivatives via ATB$^{0,+}$. The magnitude of inward currents induced by short-chain fatty acid esters of L-serine was similar to that induced by L-serine (FIG. 10). These results reconfirm the data from mammalian cells (FIG. 8). The results obtained by the short-chain fatty acid esters of L-serine were consistent in both experiments as they showed significant glycine uptake inhibition in the mammalian system and also markedly induced inward current in the oocyte expression system.

Figure 11A:
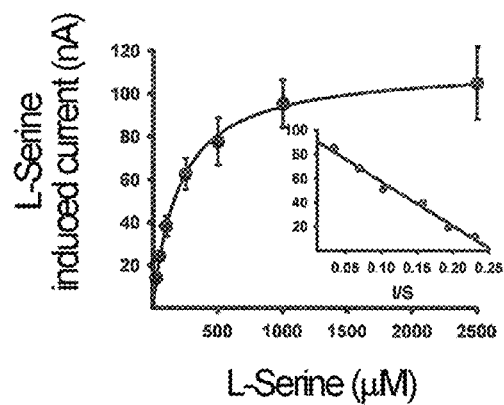
FIG. 11. Saturation kinetics of the transport of L-serine (FIG. 11A), O-acetyl-L-serine (FIG. 11B), O-propionyl-L-serine (FIG. 11C) and O-butyryl-L-serine (FIG. 11D) via rat ATB$^{0,+}$ in Xenopus oocytes. Rat ATB$^{0,+}$ was expressed in Xenopus oocytes heterologously and the currents induced by increasing concentrations of L-serine, O-acetyl-L-serine, O-propionyl-L-serine and O-butyryl-L-serine were measured. Insets: Edie-Hoftee plot (I, currents induced by O-propionyl-L-serine and O-butyryl-L-serine in Na; S, concentration of O-propionyl-L-serine and O-butyryl-L-serine in mM).
Figure 11B:
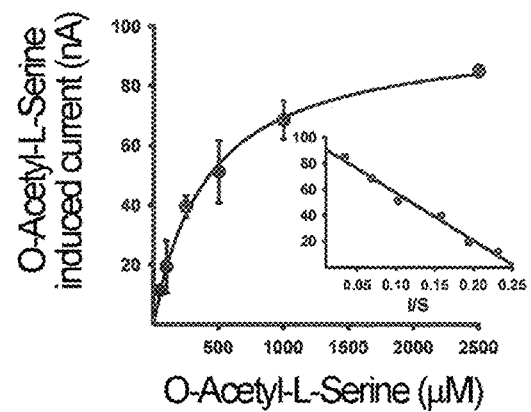
Figure 11C:
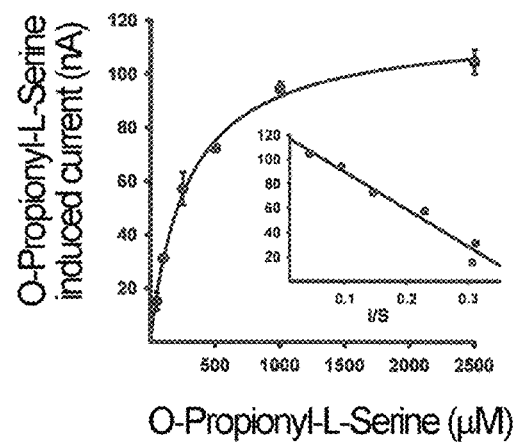
Figure 11D:
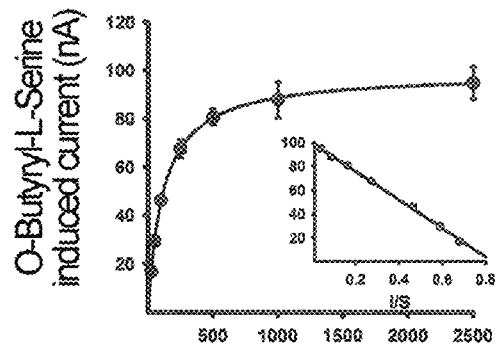

Since the preliminary studies provided the evidence for the transport of L-serine and its short-chain fatty acid esters via ATB$^{0,+}$, the kinetics of this transport process were analyzed in detail. The currents induced by L-serine, O-acetyl-L-serine, O-propionyl-L-serine and O-butyryl-L-serine in ATB$^{0,+}$-expressing oocytes were saturable with increasing concentrations of the substrate (FIG. 11). The values for $K_{0.5}$ (i.e., concentration of the substrate necessary for induction of half-maximal current) were: 175±6 μM for L-serine (FIG. 11A); 369±25 for O-acetyl-L-serine (FIG. 11B); 305±31 for O-propionyl-L-serine (FIG. 11C); and 119±2 for O-butyryl-L-serine (FIG. 11D).

The values obtained for O-acetyl-L-serine and O-propionyl-L-serine are significantly different from the $IC_{50}$ value obtained in HRPE cells for the inhibition of ATB$^{0,+}$-mediated glycine transport by O-acetyl-L-serine and O-propionyl-L-serine. The most likely reason for this difference is that while the inward currents in oocytes were measured under voltage-clamp conditions, uptake measurements in HRPE cells were not made under similar conditions. Membrane potential may have significant influence on the affinity of the transporter for the substrate. However, the values obtained from both the systems for L-serine and O-butyryl-L-serine are quite similar.

Interestingly, O-butyryl-L-serine has better affinity (199±2) for the ATB$^{0,+}$ transporter than L-serine (175±6). Analysis of activation of O-butyryl-L-serine (2 mM)-induced currents by increasing concentrations of Na$^+$ showed sigmoidal relationship, indicating involvement of multiple Na$^+$ ions in the activation process (FIG. 12A). The Hill coefficient (h) for Na$^+$, which is an estimate of the number of Na$^+$ ions involved in the activation process, was 1.74±0.23. The value for $K_{0.5}$ for Na$^+$ (i.e., concentration of Na$^+$ needed for half-maximal activation) was 5.02±0.25 mM. We carried out similar studies for the activation of O-butyryl-L-serine (2 mM)-induced currents by Cl$^-$ (FIG. 12B). In contrast to the kinetics of Na$^+$ activation, the relationship between O-butyryl-L-serine-induced currents and or concentration were hyperbolic, indicating involvement of a single Cl$^-$-ion in the activation process. Accordingly, the Hill coefficient for Cl$^-$ was 1.33±0.02. The value for $K_{0.5}$ for Cl$^-$ (i.e., concentration of Cl$^-$ needed for half-maximal activation) was found to be 6.28±0.33 mM. Thus, the Na$^+$:Cl$^-$:O-butyryl-L-serine stoichiometry for the transport of O-butyryl-L-serine via ATB$^{0,+}$ appears to be 2 or 3:1:1.

Figures 14A, 14B, 14C:
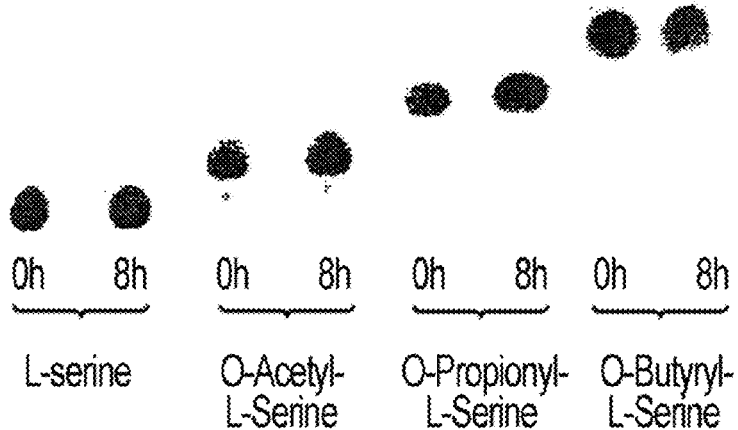
FIG. 14. Stability of SCFA esters of L-serine. L-serine, O-acetyl-L-serine, O-propionyl-L-serine and O-butyryl-L-serine were prepared at 5 mM ♦ and analyzed for the purity using thin layer chromatography (TLC) plates. The solvent system used was butanol:acetic acid:water (4:1:1). The run was stopped when the solvent reached the top of the TLC sheet and air dried and sprayed with ninhydrin (2% in acetone).

Purities of the short-chain fatty acid esters of L-serine were analyzed to check the possibility of L-serine contamination in the custom-synthesized O-propionyl-L-serine and O-butyryl-L-serine. We employed amino acid analysis techniques to check the purities. The results are shown in FIG. 13. The retention times (RT) were 13.67 minutes for L-serine, 14.03 minutes for O-propionyl-L-serine, and 20.33 minutes for O-butyryl-L-serine. Both O-propionyl-L-serine and O-butyryl-L-serine appeared to be pure, as there was an L-serine peak. However, we also employed TLC to further check the purities. O-acetyl-L-serine was also included in TLC to check its purity. TLC results indicated that all the compounds tested were pure as shown in FIG. 14A. These findings reconfirmed the results obtained by amino acid analysis.

To address the stability issue, the short-chain fatty acid esters (5 mM) were incubated with uptake buffer for eight hours at room temperature. An aliquot was also taken at 0 hours and kept on ice until use. TLC was conducted after the incubation period and the results are shown in FIG. 14B. These compounds appeared to be quite stable at room temperature for several hours.

A further experiment was conducted to see whether the cells produced esterases into the medium and cleave the ester bond from the short-chain fatty acids when incubated with the cells during uptake studies, and whether the product L-serine would be transported into the cells instead of short-chain fatty acid esters of L-serine by ATB$^{0,+}$. For this study, HRPE cells were seeded into 96-well plates. Next day, the growth medium was replaced with uptake buffer containing 5 mM of L-serine and its esters (O-acetyl-L-serine, O-propionyl-L-serine and O-butyryl-L-serine) for two hours. At the end of this time, the uptake buffer was carefully removed from the wells and analyzed by TLC (FIG. 14C). These results demonstrated the transport of short-chain fatty acid esters of L-serine via ATB$^{0,+}$.

HRPE cells were transiently transfected with rat ATB$^{0,+}$ and the 3H-glycine uptake inhibition was studied using 5 mM of L-serine, O-acetyl-L-serine, O-propionyl-L-serine and O-butyryl-L-serine (Table 2).

While this example exemplifies L-serine and a variety of α-carboxyl esters of L-serine, such as O-acetyl-L-serine, O-propionyl-L-serine and O-butyryl-L-serine, it is understood that this invention provides esters of amino acids other than L-serine, including but not limited to threonine and tyrosine. Additionally, it is understood that this invention also provides amino acid esters of other short-chain fatty adds, small hydrocarbon molecules, and anticancer molecules, including but not limited to pyruvate and 3-bromopyruvate.

TABLE 2

Kinetic analysis of L-serine, O-acetyl-L-serine, O-propionyl-L-serine and O-butyryl-L-serine

|  | $K_t$ (μM) | $V_{max}$ (nmol/10$^6$ cells/30 minutes) |
|---|---|---|
| Control | 56 ± 3 | 72 ± 2 |
| L-serine | 119 ± 15 | 55 ± 5 |
| O-acetyl-L-serine | 133 ± 36 | 46 ± 9 |

TABLE 2-continued

Kinetic analysis of L-serine, O-acetyl-L-serine,
O-propionyl-L-serine and O-butyryl-L-serine

|  | $K_t$ (µM) | $V_{max}$ (nmol/$10^6$ cells/30 minutes) |
|---|---|---|
| O-propionyl-L-serine | 132 ± 37 | 61 ± 13 |
| O-butyryl-L-serine | 102 ± 17 | 47 ± 5 |

Example 3

Functional Identification of SLC5A8, a Tumor Suppressor Downregulated in Colon Cancer, as a $Na^+$-coupled Transporter for Short-chain Fatty Acids Since all members of the SLC5 gene family, with the exception of SLC5A3 which is a glucose-sensitive $Na^+$ channel and SLC5A9 whose transport function has not yet been established (Wright, E. M., and Turk, E. (2003) *Pflugers Arch. Eur. J. Physiol.* (Epub ahead of print, May 14, 2003), are $Na^+$-coupled cotransporters for organic or inorganic solutes, we hypothesized that SLC5A8 is most likely a $Na^+$-coupled transporter for a hitherto unidentified organic or inorganic solute. The abundant expression of SLC5A8 in the colon and its suggested role as a tumor suppressor (Li, H., et al. (2003) *Proc. Natl. Acad. Sci. USA* 100:8412-8417) led us to question its purported role as a passive iodide transporter. Based on the tissue expression pattern, we hypothesized that SLC5A8 is likely to be a $Na^+$-coupled transporter as suggested by Li et al. (2003, supra) and that short-chain fatty acids may be the co-transported substrates. Short-chain fatty acids such as acetate, propionate, and butyrate are generated at high levels in the colon by bacterial fermentation of dietary fiber and unabsorbed carbohydrates and these fatty acids are the preferred metabolic fuel in colonic epithelial cells (Mortensen, P. B., and Clausen, M. R. (1996). *Scand. J. Gastroenterol* 216: 132-148; Velazquez, et al. (1997) *Adv. Exp. Med. Biol.* 427: 123-134; Topping, D. L., and Clifton, P. M. (2001) *Physiol. Rev.* 81:1031-1064).

It has been shown that short-chain fatty acids prevent colonic cell proliferation and reduce the incidence of colon cancer (Wachtershauser, A., and Stein, J. (2000) *Eur. J. Nutr.* 39:164-171; Blottiere, H. M., et al. (2003) *Proc. Nutr. Soc.* 62:101-106; Chen, J. S., et al. (2003) *Curr. Cancer Drug Targets* 3:219-236). Methylation-dependent silencing of the gene expression in the colon will decrease the availability of short-chain fatty acids to colonic epithelial cells and thus influence the metabolic profile and proliferation of these cells. These findings provided the rationale for our hypothesis that SLC5A8 might be a $Na^+$-coupled transporter for short-chain fatty acids. Here we provide evidence that human SLC5A8 does indeed function as a $Na^+$-coupled transporter for short-chain fatty acids.

Experimental Procedures
Materials.

The following radiolabeled substrates were obtained from commercial sources: [14C]-L-lactate, [14C]-D-lactate, [14C] acetate, and [3H]propionate from American Radiolabeled Chemicals (St Louis, Mo.) and [14C]pyruvate and [14C] butyrate from Moravek Biochemicals (Brea, Calif.).

Amplification of the Coding Region of Human SCL5A8

To amplify the coding region of human SLC5A8 mRNA by RT1-PCR, we designed primers based on the published sequence (Li, H., et al. (2003) *Proc. Natl. Acad. Sci. USA* 100:8412-8417) in GenBankTM data base (accession number AF526216). The sense primer, containing the initiation codon (shown in bold), was 5-GATATATAGCCATGGA-CACGCCA CGGGGCAT-3 (SEQ ID NO:7), and the antisense primer, located downstream of the stop codon, was 5-CGCGAAGCTTCACAAACGAGTCCCATTGCT-3 (SEQ ID NO:8). The underlined sequence in the antisense primer is a HindIII site, added to the 5-end of the primer for cloning purpose. RT-PCR with these primers and human intestinal mRNA as the template yielded a 1.9-kb product as expected from the positions of the primers in the published sequence (sense, 361-383; antisense, 2176-2204). This product was subcloned into pGEM-T Easy vector. The insert was then released from the plasmid by digestion with EcoRI and HindIII and subcloned into the vector pGH19 at the EcoRI/HindIII site. The pGH19 vector contains the 3-untranslated region of the *Xenopus* globin gene downstream of the cloning site. The cDNA were sequenced by the Taq DyeDeoxy terminator cycle method using an automated PerkinElmer Applied Biosystems 377 Prism DNA sequencer.

Functional Analysis of SLC5A8 in *Xenopus* Oocytes

The amplified human SLC5A8 cDNA was expressed heterologously in *Xenopus* oocytes by cRNA injection. Capped cRNA from SLC5A8 cDNA was synthesized using the mMESSAGE mMACHINE kit (Ambion Inc., Austin, Tex.). Mature oocytes (stage 1V or V) from *Xenopus laevis* were injected with 50 ng cRNA. Uninjected oocytes served as controls. The oocytes were used for uptake and electrophysiological studies 3-6 days after cRNA injection. Uptake of radiolabeled substrates in uninjected and cRNA-injected oocytes was determined as described previously (Fei, Y. J., et al., (1995) *Biochemistry* 34, 8744-8751).

Eight oocytes were used for each uptake measurement. Electrophysiological studies were performed by the two-microelectrode voltage clamp method (11. Wang, H., Fei, et al., (2000) *Am. J. Physiol.* 278:C1019-C1030; Inoue, K, et al. (2004) *Biochem. J.* 378:949-957).

Oocytes were perfused with a NaCl-containing buffer (100 mM NaCl, 2 mM KCl, 1 mM MgCl2, 1 mM CaCl2, 3 mM Hepes, 3 mM Mes, and 3 mM Tris, pH 7.5), followed by the same buffer containing different fatty acids. The membrane potential was clamped at −50 mV. The differences between the steady-state currents measured in the presence and absence of substrates were considered as the substrate-induced currents. To investigate the current-membrane potential (I—V) relationship, step changes in membrane potential were applied, each for a duration of 100 ms in 20-mV increments. The kinetic parameter K0.5 (i.e. the substrate concentration necessary for the induction of half-maxima) current) was calculated by fitting the values of the substrate-induced currents to Michaelis-Menten equation. The $Na^+$-activation kinetics was analyzed by measuring the substrate-specific currents in the presence of increasing concentrations of $Na^+$. The data were analyzed by the Hill equation to determine the Hill coefficient (h; the number of $Na^+$ ions involved in the activation process). The kinetic parameters were determined using the computer program Sigma Plot, version 6.0 (SPSS, Inc., Chicago, Ill.). Electrophysiological measurements of substrate-induced currents were repeated at least four times with separate oocytes. The data are presented as means±S.E. of these replicates.

Determination of Charge/Substrate Transfer Ratio

The charge-to substrate transfer ratio was determined for propionate in four different oocytes as described previously (Wang, H., et al. (2000) *Am. J. Physiol.* 278:C1019-C1030 12. Inoue, K., Fei, Y. J., Zhuang, L., Gopal, E., Miyauchi, S., and Ganapathy, V. (2004) *Biochem. J.* 378:949-957). The oocytes were perfused with 25 μM propionate (unlabeled plus radiolabeled propionate), and inward currents were monitored over a period of 8-10 min. At the end of the experiment, the amount of propionate transported into the oocytes was calculated by measuring the radioactivity associated with the oocytes. The area within the curve describing the relationship between the time and inward current was integrated to calculate the charge transferred into the oocyte during incubation with propionate. The values for substrate transfer and charge transfer were used to determine the charge to substrate transfer ratio.

Results

Amplification of the Coding Region of Human SLC5A8mRNA for Functional Expression in *Xenopus* Oocytes We amplified the coding region of SLC5A8 mRNA by RT-PCR using human intestinal mRNA as the template. The amino acid sequence of the amplified product was identical to the published sequences (Li, H., et, al. (2003) *Proc. Natl. Acad. Sci. USA* 100:8412-8417; Rodriguez, A. M., et al. (2002) *J. Clin. Endocrinol. Metab.* 87:3500-3503) except for the amino acids at positions 193 and 251. Our amplified cDNA contains Ile at position 193 and Val at position 251. The corresponding amino acids are Ile and Phe in the clone reported by Li, H., et al. (2003) *Proc. Natl. Acad. Sci. USA* 100:8412-84171, and Val and Phe in the clone reported by Rodriguez, A. M., et al. (2002) *J. Clin. Endocrinol. Metab.* 87:3500-3503.

Identification of SLC5A8 as a $Na^+$-Coupled Transporter for Short-Chain Fatty Acids We tested our hypothesis that SLC5A8 is a $Na^+$-coupled transporter for short-chain fatty acids by measuring the uptake of several fatty acids in uninjected oocytes and in oocytes injected with SLC5A8 cRNA (Table 3). The uptake of all fatty acids tested (L-lactate, D-lactate, pyruvate, acetate, propionate, and butyrate) was higher in cRNA-injected oocytes than in uninjected oocytes. The cRNA-induced increase in uptake varied in the range of 2-45-fold depending on the fatty acid. This increase was not observed when the uptake was measured in the absence of $Na^+$ (data not shown).

Uptake of short-chain fatty acids in uninjected oocytes and in oocytes injected with SLC5A8 cRNA was measured with 1 h incubation. Concentration of substrates (labeled plus unlabeled) varied in the range of 50-500 μM depending on the specific radioactivity of the substrates. Eight oocytes were used for each uptake measurement. Data represent means±SE.

TABLE 3

Uptake of short-chain fatty acids in uninjected oocytes and in oocytes injected with SLC5A8 cRNA

| Substrate | Uninjected oocytes | cRNA-injected oocytes | Fold increase |
|---|---|---|---|
| L-Lactate (50 μM) | 0.009 ± 0.001 | 0.402 ± 0.026 | 44.7 |
| D-Lactate (150 μM) | 0.028 ± 0.002 | 1.090 ± 0.041 | 38.9 |
| Pyruvate (500 μM) | 0.151 ± 0.017 | 2.622 ± 0.075 | 17.4 |
| Acetate (150 μM) | 0.032 ± 0.001 | 0.059 ± 0.003 | 1.8 |
| Propionate (50 μM) | 0.016 ± 0.001 | 0.255 ± 0.014 | 15.9 |
| Butyrate (150 μM) | 0.029 ± 0.001 | 0.116 ± 0.007 | 4.0 |

Electrophysiological Studies of SLC5A8

Figure 15A:
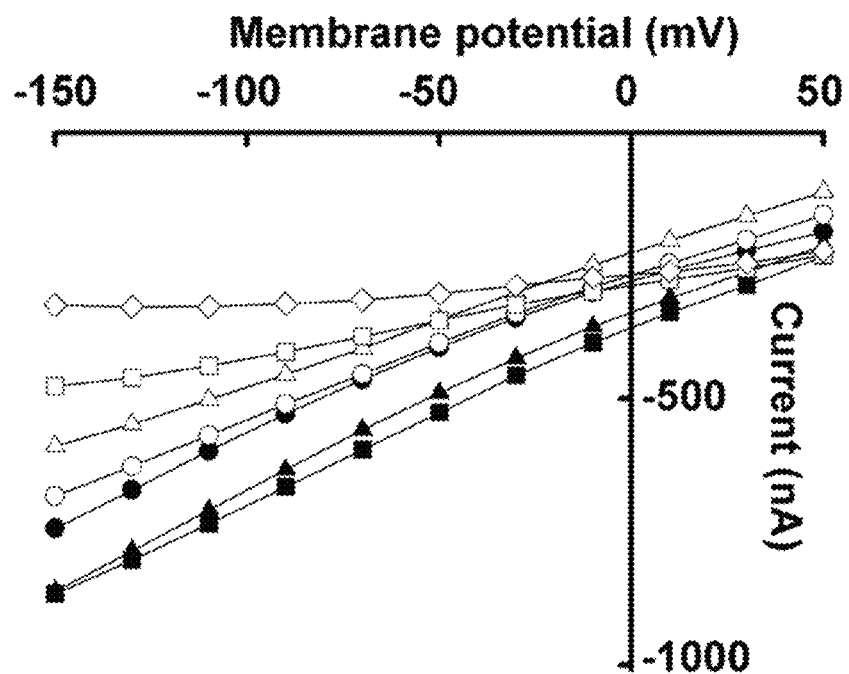
FIG. 15A illustrates a current-voltage relationship for substrate-induced currents in SLC5A8-expressing oocytes. Concentration of substrates in the perfusion medium was 5 mM. There were no detectable currents in uninjected oocytes under identical conditions. (●) L-lactate; (○) D-lactate; (▲) pyruvate; acetate; (■) propionate; (□) butyrate; (♦) pentanoate.
Figure 15B:
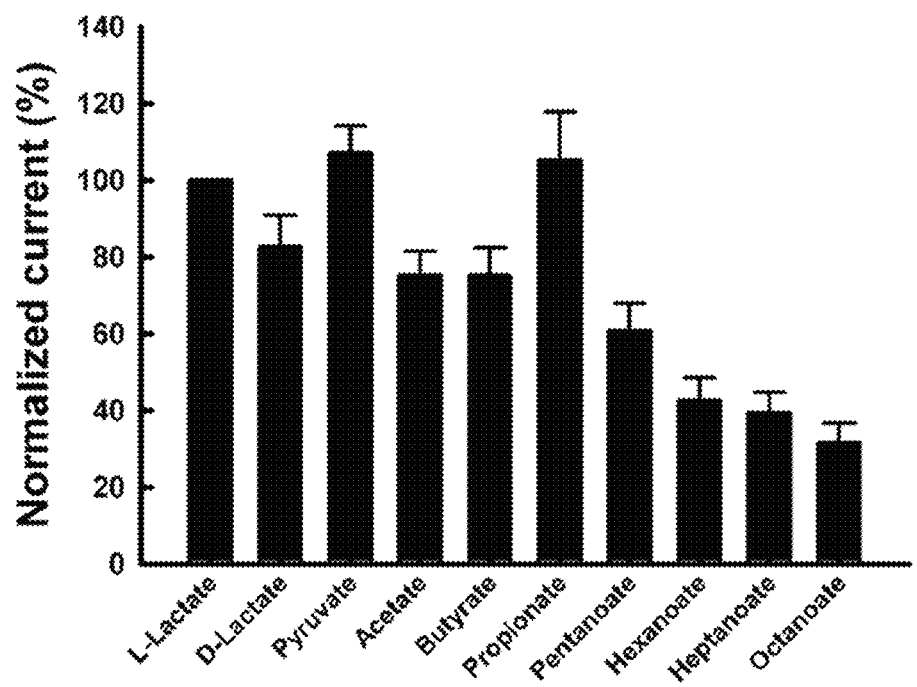
FIG. 15B shows relative magnitude of inward currents induced at −50 mV by various short-chain fatty acids (5 mM) with the current induced by L-lactate normalized to 100% (489±94 nA).
Figure 16A:
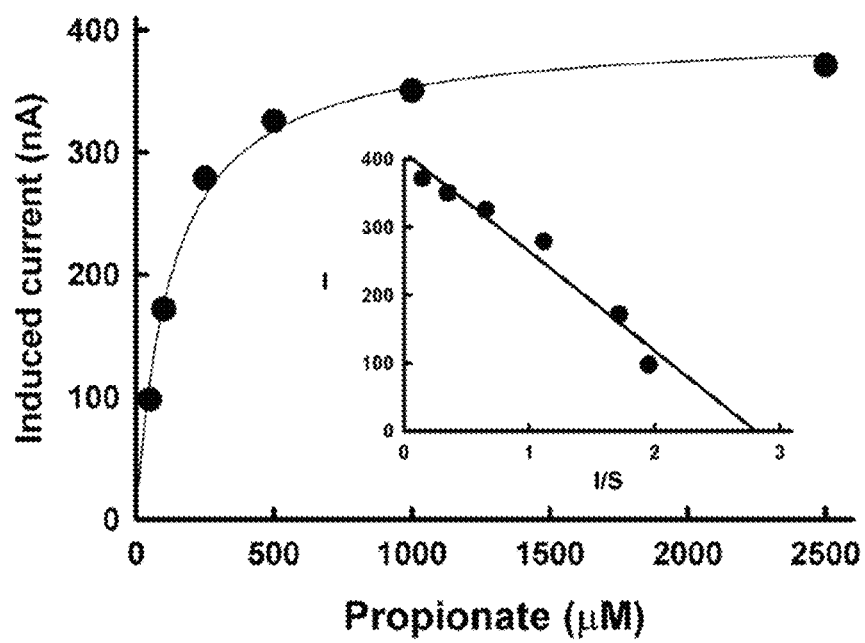
FIG. 16A shows saturation kinetics for propionate in SLC5A8-expressing oocytes at a Na$^+$ concentration of 100 mM. Inset, Eadie-Hofstee plot
Figure 16B:
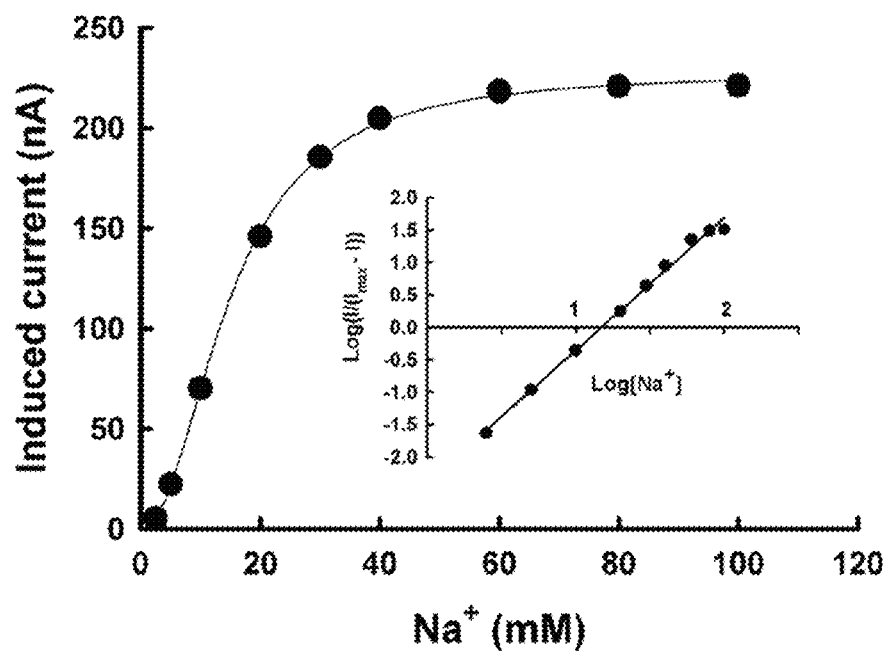
FIG. 16B illustrates Na$^+$-activation kinetics for propionate (5 mM) in SLC5A8-expressing oocytes. Inset, Hill plot. Data are from a representative oocyte. Similar results were obtained in three other oocytes.
Figure 17A:
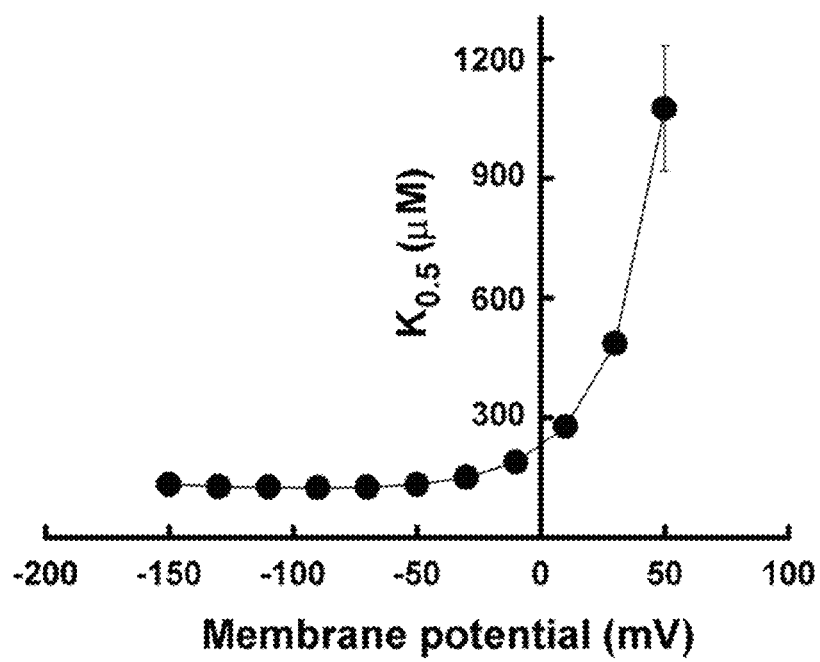
FIG. 17A illustrates the influence of membrane potential on K$_{0.5}$ (i.e. concentration of propionate needed for the induction of half-maximal current).

We then examined the transport function of SLC5A8 by electrophysiological methods. Exposure of cRNA-injected oocytes to various short-chain fatty acids induced marked inward currents under voltage clamp conditions and the magnitude of these currents increased as the testing membrane potential was changed from positive values to negative values (FIG. 15A). Exposure of uninjected oocytes to these fatty acids did not induce detectable currents (data not shown). We then compared the substrate-induced currents in cRNA-injected oocytes among several fatty acids (5 mM). The currents, measured at −50 mV, were maximal for L-lactate, pyruvate, and propionate, intermediate for D-lactate, acetate, butyrate, and pentanoate and lowest for hexanoate, heptanoate, and octanoate (FIG. 15B). With propionate as the substrate, we analyzed the saturation kinetics and $Na^+$-activation kinetics. Results from a representative oocyte are given in FIG. 16 and similar results were obtained in three different additional oocytes. Propionate-induced currents were saturable with a $K_{0.5}$ value of 127±14 μM (FIG. 16A). The relationship between propionate-induced currents and $Na^+$ concentration was sigmoidal and the value for Hill coefficient (h) was 2.0±0.1 (FIG. 16B). The $K_{0.5}$ value was not influenced significantly by the testing membrane potential between −30 mV and −150 mV (FIG. 17A). But, the value increased dramatically when the testing membrane potential became more positive.

Figure 17B:
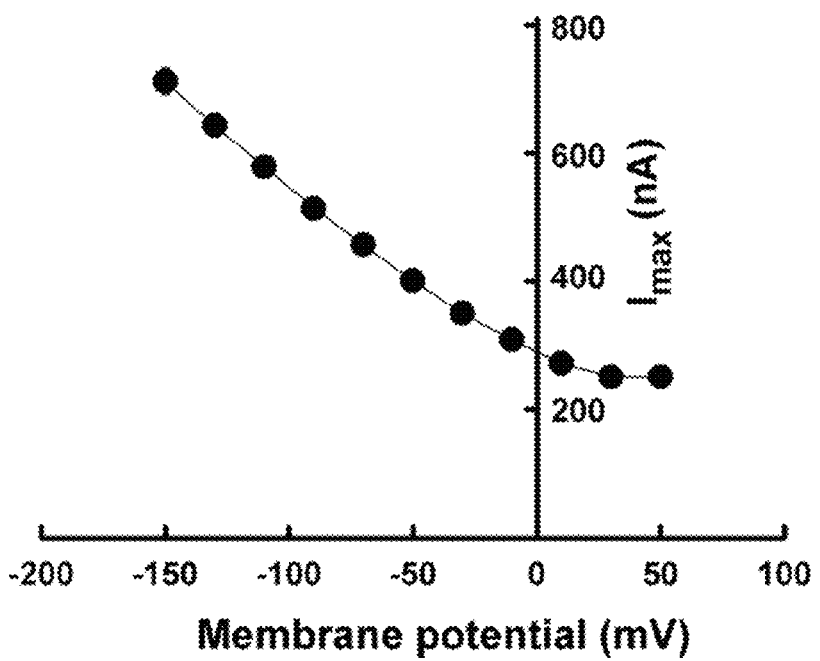
FIG. 17B illustrates the influence of membrane potential on Imax (i.e. current induced by maximal concentrations of propionate) in SLC5A8-expressing oocytes.

The $I_{max}$ value (i.e. the current induced by the substrate at maximal concentrations) was however influenced by the testing membrane potential profoundly, the values being higher at hyperpolarized membrane potentials than at depolarized membrane potentials (FIG. 17B).

Comparative Affinities of Short-chain Fatty Acids for SLC5A8

We determined the $K_{0.5}$ values for L-lactate, D-lactate; acetate, propionate, and butyrate to compare the affinities of these fatty acids for interaction with SLC5A8. The affinities were found to be in the following order: butyrate (81±17 μM)>propionate (127±14 μM)>L-lactate (235±24 μM)>D-lactate (742±330 μM)>acetate (2.46±0.89 mM). These data were from four different oocytes.

Charge-to-Substrate Transfer Ratio

Figure 18A:
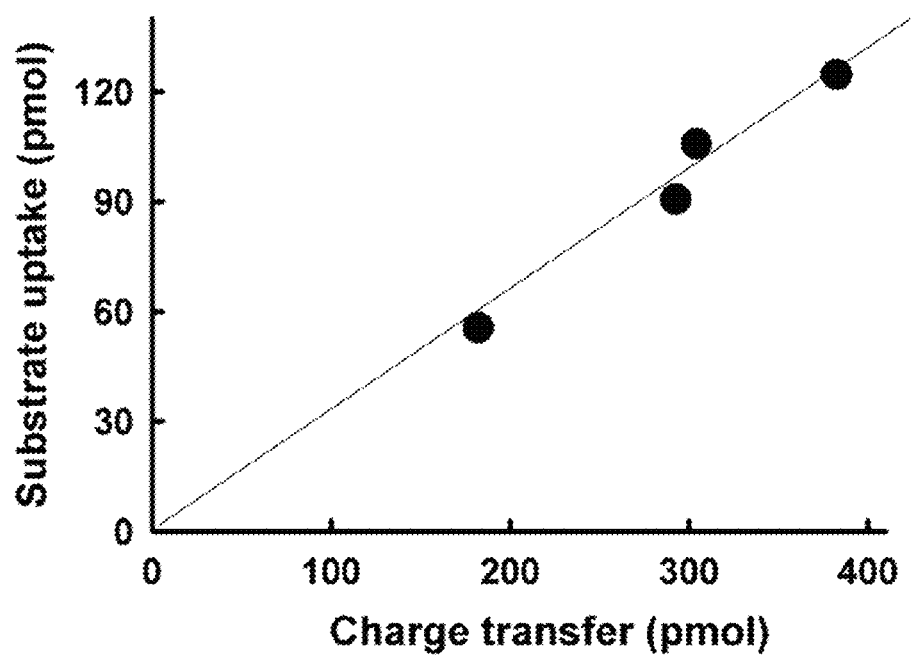
FIG. 18A shows the relationship between substrate transfer and charge transfer in four different SLC5A8-expressing oocytes. Propionate (25 μM) was used as the substrate.
Figure 18B:
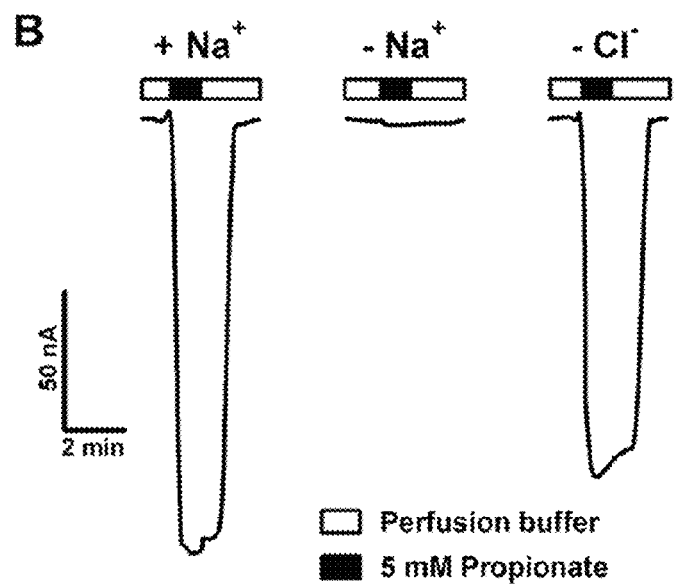
FIG. 18B illustrates Na$^+$ and Cl$^-$ dependence of propionate (5 mM)-induced current in SLC5A8-expressing oocytes. The perfusion medium contained 100 mM NaCl (+Na$^+$), 100 mM N-methyl-D-glucamine chloride (−Na$^+$), or 100 mM sodium gluconate (−Cl$^-$).

The $Na^+$-activation kinetics with propionate suggested that at least two $Na^+$ are involved in the activation process. Propionate exists as a monovalent anion at pH 7.5 and co-transport of two $Na^+$ with one propionate molecule would predict the transport process to be electrogenic and explain the observed propionate-induced inward currents under voltage-clamp conditions. However, the Hill coefficient is only an estimate and does not always predict the exact number of coupled ions involved in the transport process. Therefore, we directly measured the transfer of propionate and charge simultaneously in the same oocytes to determine the exact value for the charge-to-substrate ratio (FIG. 18A). The value for this ratio determined with four different oocytes for propionate was 3.1±0.1. To determine whether any other anions such as $Cl^-$ or $OH^-$ are involved in the transport process, we examined the ionic dependence of propionate-induced currents (FIG. 18B). The substrate-induced currents were obligatorily dependent on the presence of $Na^+$, but there appeared to be no involvement of $Cl^-$ as there was no significant change in the magnitude of the currents when $Cl^-$ was replaced by gluconate in the perfusion medium. We also investigated whether the currents were influenced by external pH. The propionate-induced currents remained the same over the pH range 6-8, suggesting that anions such as $OH^-$ are not likely to be involved in the transport process (data not shown).

Interaction of Iodide with SLC5A8

Since studies by Rodriguez et al. (Rodriguez, A. M., et al. (2002) *J. Clin. Endocrinol. Metab.* 87:3500-3503) have shown that SLC5A8 functions as a passive transporter for iodide, we examined the potential interaction of this inorganic anion with SLC5A8 in cRNA-injected oocytes. The presence of 5 mM NaI did not induce any detectable current (inward or outward) in these oocytes (data not shown).

Discussion

The present studies have established the functional identity of human SLC5A8 as a Na$^+$-coupled transporter for short-chain fatty acids with a Na$^+$:substrate stoichiometry of 4:1. This is evident from the uptake of radiolabeled substrates as well as from substrate-induced inward currents. The inward currents induced by short-chain fatty acids are obligatorily dependent on Na$^+$. Neither Cl$^-$ nor OH$^-$ is involved in the transport process. The magnitude of the substrate-induced currents is maximal for fatty acids containing 2-5 carbon atoms and the currents decrease as the carbon chain length increases. Under the experimental conditions employed in our studies, we could not detect any interaction of iodide with SLC5A8. The reasons for the differences between our studies and those of Rodriguez et al. (Rodriguez, A. M., et al. (2002) *J. Clin. Endocrinol. Metab.* 87, 3500-3503) are not known. Li et al. (Li, H., et al. (2003) *Proc. Natl. Acad. Sci. USA* 100, 8412-8417) have shown that SLC5A8-expressing oocytes had higher levels of Na$^+$, leading to the conclusion that SLC5A8 is a Na$^+$ transporter even though their studies did not establish the identity of the co-transported ion. Sodium pyruvate is normally added to the medium used in the maintenance of oocytes following cRNA injection, and incubation of SLC5A8-expressing oocytes in pyruvate-containing medium during the maintenance of the oocytes is expected to increase intracellular Na$^+$ based on the functional identity of the transporter established in the present studies. However, it was not readily apparent whether or not the oocytes were maintained in the presence of pyruvate in the studies reported by Li et al. (Li, H., et al. (2003) *Proc. Natl. Acad. Sci. USA* 100, 8412-8417).

Our studies show unequivocally that SLC5A8 is a Na$^+$-coupled transporter for short-chain fatty acids. The substrate specificity of SLC5A8 is similar to that of H$^+$-coupled monocarboxylate transporters (MCTs) (Halestrap, A. P., and Price, N. T. (1999) *Biochem. J.* 343:281-299). Therefore, based on the functional identity of SLC5A8 as the Na$^+$-coupled transporter for monocarboxylates, we refer to this transporter as SMCT (for sodium-coupled monocarboxylate transporter). However, there is no sequence similarity between SMCT and MCTs. The functional identity of SMCT as a Na$^+$-coupled transporter for short-chain fatty acids is very important with regard to the abundant expression of the transporter in colon (Li, H., et al. (2003) *Proc. Natl. Acad. Sci. USA* 100, 8412-8417) where these fatty acids are generated at high levels by bacterial fermentation. In the past, several studies have focused on the transport routes available for the absorption of short-chain fatty acids in the colon (Rajendran, V. M., and Binder, H. J. (2000) *Ann. N.Y. Acad. Sci.* 915:15-29; Sellin, J. H. (1999) *News Physiol. Sci.* 14:58-64), but surprisingly none of these studies has identified the presence of a Na$^+$-coupled absorptive mechanism for these fatty acids. However, a Na$^+$-coupled lactate transport system has been demonstrated in renal brush border membrane vesicles (Barac-Nieto, M., Murer, H., and Kinne, R. (1980) *Am. J. Physiol.* 239:F496-F506; Barbarat, B., and Podevin, R. A. (1988) *J. Biol. Chem.* 263:12190-12193), but the molecular identity of the transport system has not yet been established. Since SLC5A8 transcripts are expressed in kidney (Li, H., et al. (2003) *Proc. Natl. Acad. Sci. USA* 100, 8412-8417), this transporter is responsible for Na$^+$/lactate co-transport in kidney. The ability of SMCT to transport D-lactate is of physiological relevance, because while mammalian metabolism generates exclusively L-lactate, bacterial metabolism generates not only L-lactate but also D-lactate (Bongaerts, G. P., et al. (1997) *Microb. Pathog.* 22:285-293). Therefore, SMCT is responsible for the absorption of D-lactate from the intestinal tract. D-Lactate is found in human blood and elevated levels of D-lactate in blood (D-lactic acidosis) result from bacterial overgrowth in the small intestine under various clinical and pathological conditions (Uribarri, J., et al. (1998) *Medicine* (Baltimore) 77:73-82).

The functional identification of SMCT as a Na$^+$-coupled transporter for short-chain fatty acids is also relevant to recent studies by Li et al. (Li, H., et al. (2003) *Proc. Natl. Acad. Sci. USA* 100, 8412-8417). Their studies suggested that this transporter may function as a tumor suppressor because its expression is silenced in colon cancer. The absorption of short-chain fatty acids is impaired in colonocytes at the site of cancer. Several studies have shown that short-chain fatty acids in the colon are effective in reducing the incidence of colon cancer (Wachtershauser, A., and Stein, J. (2000) *Eur. J. Nutr.* 39:164-171; Blottiere, H. M., et al. (2003) *Proc. Nutr. Soc.* 62:101-106; Chen, J. S., et al. (2003) *Curr. Cancer Drug Targets* 3:219-236). The potential mechanisms of tumor suppression by these fatty acids include inhibition of histone deacetylases (Hinnebusch, B. F., et al. (2002) *J. Nutr.* 132:1012-101), induction of apoptosis (Jan, G., et al (2002) *Cell Death Differ.* 9:179-188; Augenlicht, L. H., et al. (1999) *Cancer Res.* 59:6005-6009), modulation of gene expression (Basson, M. D., et al., (2000) *J. Gastrointest. Surg.* 4:501-512), and induction of cell cycle arrest (Wang, J., and Friedman, E. A. (1998) *Gastroenterology* 114:940-946). These fatty acids are also involved in the prevention of colon cancer metastasis (Emenaker, N. J., et al. (2001) *J. Nutr.* 131:3041S-3046S).

Example 4

Preparation of O-Propionyl-L-Serine (2020370)

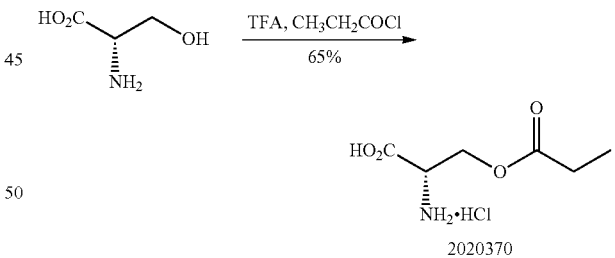

2020370

L-Serine (5.25 g, 50 mmol) was added with stirring to trifluoroacetic acid (35 ml) and the resultant was decanted from the insoluble material. Propionyl chloride (5.66 ml, 64.0 mmol) was then added to the solution and the mixture was stirred for 1 h at room temperature. Upon the addition of diethyl ether (6 ml), a white solid precipitated which redissolved upon stirring. The reaction vessel was sealed and left to stand overnight in a refrigerator. Further diethyl ether (30 ml) was added to the cold solution with stirring. The resultant fine white precipitate was collected by filtration, washed with diethyl ether, and dried under vacuum to afford 6.43 g (32.5 mmol, 65%) of 2020370, m.p. 148-150° C. (dec.). $^1$H NMR (300 MHz, d$_6$-DMSO) δ 0.96 (t, J 7 Hz, 3H), 2.29 (m, 2H), 4.21 (br s, 1H), 4.39 (m, 2H), 8.75 (br s, 3H). $^{13}$C NMR (75.5 MHz, d$_6$-DMSO) δ 8.7, 27.2, 52.0, 61.3, 168.9, 174.0. m/z 162.1 [M+H]$^+$.

Example 5

Preparation of O-Butyryl-L-serine (2020371)

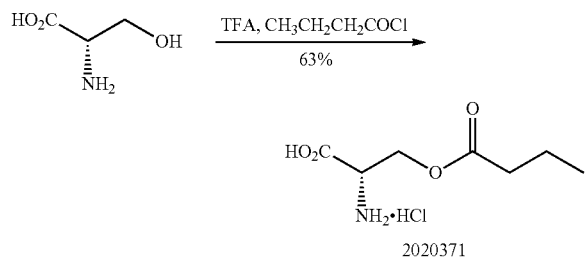

L-Serine (10.5 g, 0.10 mol) was added with stifling to trifluoroacetic acid (70 ml) and the resultant solution was decanted from the insoluble material. Butyryl chloride (13.5 ml, 0.123 mol) was then added to the solution and the mixture was stirred for 1 h at room temperature. Upon the addition of diethyl ether (20 ml), a white solid precipitated which redissolved upon stirring. The reaction vessel was sealed and left to stand overnight in a refrigerator. Further diethyl ether (60 ml) was added to the cold solution with stirring. The resultant fine white precipitate was collected by filtration, washed with diethyl ether, and dried under vacuum to afford 13.4 g (60.0 mmol, 63%) of 2020371, m.p. 165-168° C. (dec.). $^1$H NMR (300 MHz, d$_6$-DMSO) δ 0.80 (t, J 7 Hz, 3H), 1.46 (m, 2H), 2.24 (m, 2H), 4.21 (br s, 1H), 4.38 (m, 2H), 8.75 (br s, 3H). $^{13}$C NMR (75.5 MHz, d$_6$-DMSO) δ 13.5, 18.1, 35.1, 57.7, 62.1, 168.3, 173.0. m/z 176.1 [M+H]$^+$.

Other prodrugs of this invention may be prepared by analogous methods, with modifications as understood by those of ordinary skill in the art of chemical synthesis.

Example 6

Induction of Histone Acetylation and Apoptosis in Mammary Epithelial Cells by C/EBPδ and SLC5A8

C/EBPδ, a transcription factor, regulates pro-apoptotic gene expression during mammary gland involution, and is down-regulated in breast cancer (Kuramoto, T. et al. (2002) *Cancer Res.* 62:3592-3597; Porter, D. et al. (2003) *Mol. Cancer. Res.* 1:362-375). SLC5A8 (also referred to as SMCT1) is a Na$^+$-coupled transporter for short-chain monocarboxylates, including butyrate and pyruvate (Miyauchi, S., Gopal, E., Fei, Y. J. & Ganapathy, V. (2004) *J. Biol. Chem.* 279:13293-13296; Coady, M. J. et al. (2004) *J. Physiol. (Lond.)* 557, 719-731; Gopal, E. et al. (2004) *J. Biol. Chem.* 279:44522-41532; Gopal, E. et al. (2005) *Biochem. J.* 388:309-316). It represents the first plasma membrane transporter with a suggested role in tumor suppression (Ganapathy, V., Gopal, E., Miyauchi, S. & Prasad, P. D. (2005) *Biochem. Soc. Trans.* 33:237-240; Gupta, N., Martin, P. M., Prasad, P. D. & Ganapathy, V. "SLC5A8 (SMCT1)-mediated transport of butyrate forms the basis for the tumor suppressive function of the transporter," (2005) *Life Sci.* in press). Its expression is also silenced in cancer (Li, H. et al. (2003) *Proc. Natl. Acad. Sci. USA* 100:8412-8417; Ueno, M. et al. (2004) *Tumour Biol.* 25:134-140; Hong, C. et al. (2005) *Cancer Res.* 65:3617-3623; Porra, V. et al. (2005) *J. Clin. Endocrinol. Metab.* 90:3028-3035).

Here we show a direct relationship between the expressions of C/EBPδ and SMCT1 (also referred to as SLC5A8) in the mammary gland. c/ebpδ and SMCT1 are co-ordinately up-regulated in the mouse mammary gland during involution. SMCT1 expression is markedly reduced in c/ebpδ$^{-/-}$ mice. The up-regulation of c/ebpδ and SMCT1 during mammary gland involution is associated with an increase in histone acetylation in wild type mice. Both genes are expressed at higher levels in non-transformed mammary epithelial cell lines than in tumor cell lines. Transient expression of SMCT1 in MCF7 cells, a breast tumor cell line with deficient expression of C/EBPδ and SMCT1, causes apoptosis and the process is associated with pyruvate-dependent inhibition of histone deacetylases (HDACs), stimulation of C/EBPδ expression, and suppression of colony formation. Lactate, present at high levels in tumor cells, has no effect on HDAC activity and on colony formation in MCF7 cells under similar conditions. These studies provide evidence for the following: i) the control of expression of C/EBPδ and SMCT1 in the mammary gland is inter-dependent, ii) these two proteins are critical determinants of histone acetylation and apoptosis in involuting mammary gland and in breast cancer cell lines, iii) pyruvate is an inhibitor of HDACs and colony formation in tumor cells whereas lactate is not, and iv) SMCT1 controls histone acetylation and apoptosis by mediating the entry of endogenous HDAC inhibitors (e.g., butyrate and pyruvate) into cells. These data provide important insights into the mechanism of the tumor suppressive role of SMCT1.

Figure 1B:
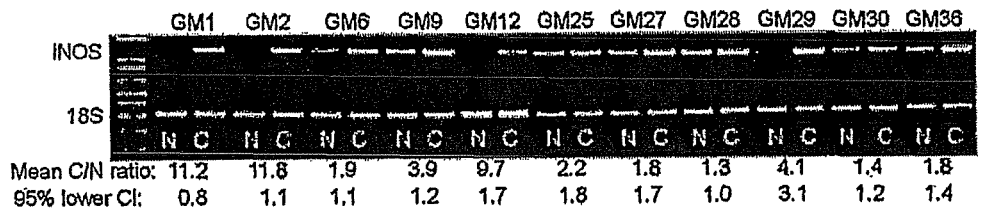
Figure 1C:
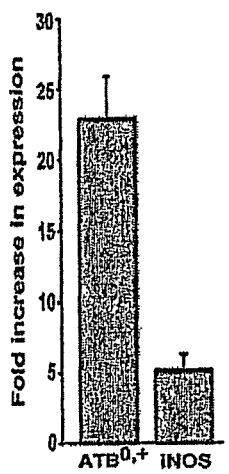
Figure 19A:
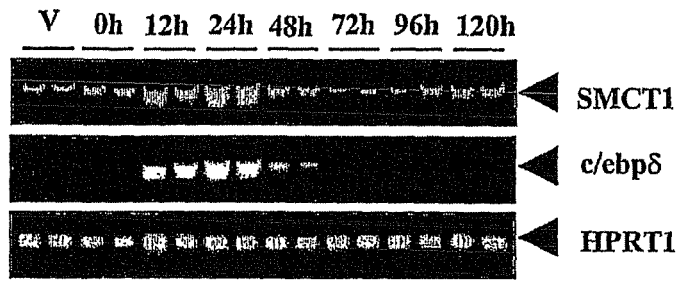
FIG. 19A, shows expression of SMCT1 mRNA in mammary gland in wild type virgin mice (V), lactating mice (0 h), and during different periods of involution (12, 24, 48, 72, 96 and 120 h). Abdominal mammary glands from C57BL/6 mice were harvested for extraction of RNA. Semi-quantitative RT-PCR was used to analyze the expression of SMCT1 mRNA and c/ebpδ mRNA with hypoxanthine guanine phosphoribosyl transferase 1 (HPRT1) mRNA as an internal control.
Figure 19B:
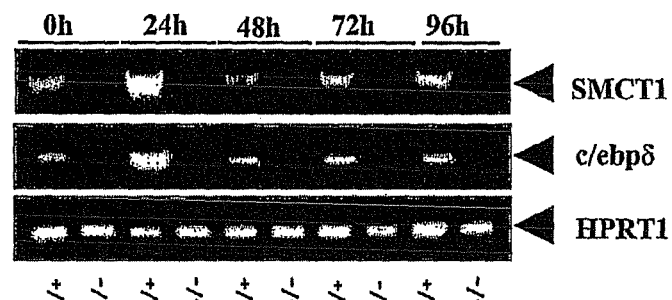
FIG. 19B shows expression of SMCT1 in mammary gland during different periods of involution in wild type (+/+) and c/ebpδ$^{-/-}$ (-/-) mice.
Figure 19C:
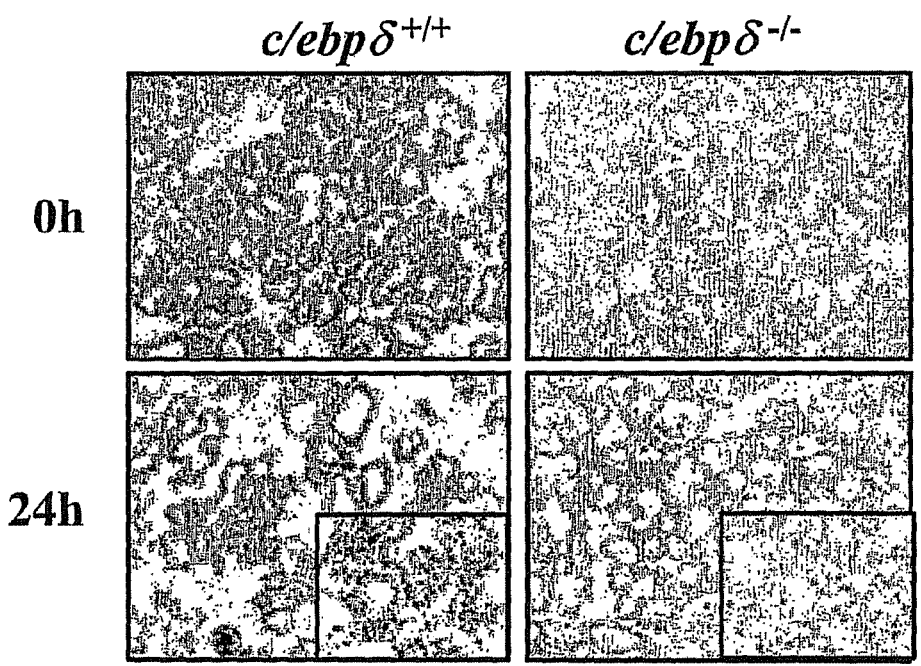
FIG. 19C is an immunohistochemical analysis of expression of SMCT1 in mammary gland in wild type and c/ebpδ$^{-/-}$ mice at 0 and 24 h of involution.
Figure 26:
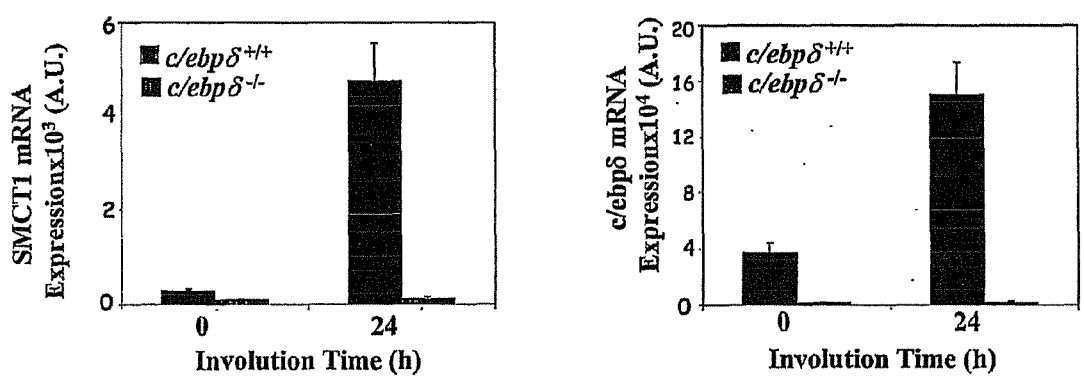
FIG. 26 shows SMCT1 and c/ebpδ mRNA in the mammary gland of wild type and c/ebpδ$^{-/-}$ mice at 0 and 24 h following induction of involution.

Breast milk contains triglycerides with butyrate as a fatty acid component (Glass, R. L., Jenness, R. & Lohse, L. W. (1969) *Comp. Biochem. Physiol.* 28, 783-786; Smith, L. M. & Hardjo, S. (1974) *Lipids* 9, 674-678). Mammary gland involution following termination of suckling is associated with apoptosis of mammary epithelial cells. c/ebpδ is highly induced during involution, and targeted disruption of this gene leads to delaying of the involution process (Thangaraju, M. et al. "C/EBPδ is a crucial regulator of pro-apoptotic gene expression during mammary gland involution," *Development* 132, in press (2005)). Therefore, it is hypothesized that SMCT1 may be expressed in the mammary gland during involution to facilitate butyrate entry into mammary epithelial cells with consequent HDAC inhibition and apoptosis and that the expression of SMCT1 in this tissue may be under the control of c/ebpδ. To test this hypothesis, SMCT1 expression in the mammary gland in normal mice and in c/ebpδ$^{-/-}$ mice at different periods of involution were analyzed. The expression of c/ebpδ and SMCT1 in the mammary gland is low in virgin mice and at the beginning of mammary gland involution; the expression increases several-fold at 12 and 24 h following initiation of involution and declines at subsequent periods (FIG. 1a). Thus, the expression of c/ebpδ and that of SMCT1 exhibit a parallel temporal pattern in the mammary gland during involution. The involution-dependent up-regulation of SMCT1, evident at the mRNA level and protein level in normal mice, is not seen in c/ebpδ$^{-/-}$ mice (FIGS. 19B, 19C and 26); the expression of SMCT1 is nearly undetectable in these mice. In normal mice, the transporter is detectable only in lactating lobules, and the expression is restricted to the luminal membrane of the epithelial cells (FIG. 19C).

Figure 20A:
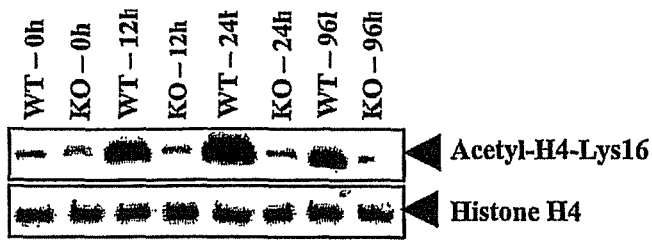
FIG. 20A shows an increase in the acetylation status of histone H4 during mammary gland involution in wild type (WT, c/ebpδ$^{+/+}$) and c/ebpδ knockout (KO, c/ebpδ$^{-/-}$) mice. Mammary glands were harvested from c/ebpδ$^{+/+}$ and c/ebpδ$^{-/-}$ mice at different periods of involution (0, 12, 24 and 96 h) and proteins were extracted. Western blot analysis was carried out with these protein samples using antibodies against histone H4 and acetylated histone H4 (Lys16).
Figure 20B:
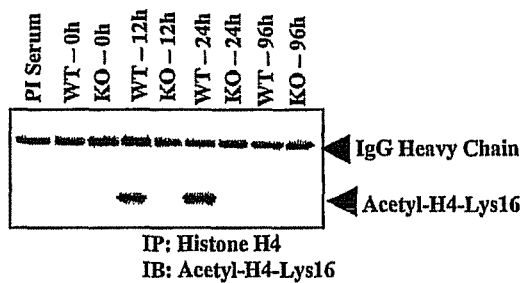
FIG. 20B shows protein samples from the above experiment were immunoprecipitated with an anti-histone H4 antibody and the immunoprecipitate was subjected to western blot with an antibody against acetylated histone H4 (Lys16).
Figure 20C:
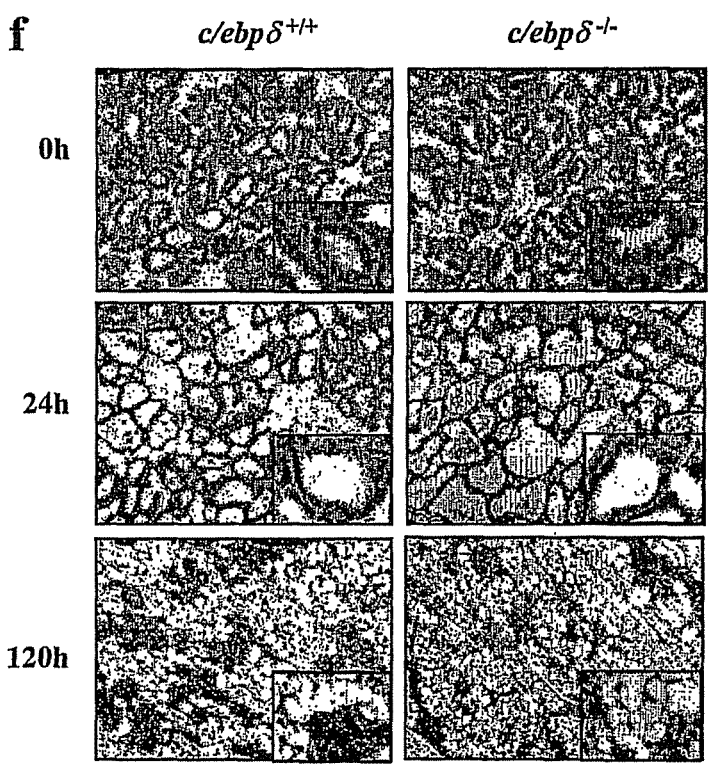
FIG. 20C is an immunohistochemical analysis of the acetylation status of histone H4 in intact mammary gland during different periods of involution in wild type (c/ebpδ$^{+/+}$) and c/ebpδ knockout (c/ebpδ$^{-/-}$) mice. Tissue sections were analyzed with an antibody against acetylated histone H4 (Lys16).

To determine whether the up-regulation of SMCT1 during mammary gland involution is associated with HDAC inhibition, possibly through enhanced entry of butyrate from the lumen into epithelial cells, the acetylation status of Lys16 in histone H4 between wild type and c/ebpδ$^{-/-}$ mice during mammary gland involution were compared. The focused was on Lys16 of histone H4 because of the available evidence in support of a role for the acetylation of this particular residue in human cancer (Fraga, M. F. et al., (2005) *Nat. Genet.* 37:391-400), Loss of acetylation at Lys16 of histone H4 is a hallmark of cancer in humans. There is significant similarity in terms of cellular processes between lactating mammary gland and tumor and between mammary gland involution and tumor regression. Analysis of the acetylation status of Lys16 of histone H4 show that, in parallel to the temporal pattern of SMCT1 expression during involution in normal mice, there is an increase in acetylation at Lys16 of histone H4 (FIGS. 20A-20C). As the expression of SMCT1 is drastically reduced in the mammary gland in c/ebpδ$^{-/-}$ mice, there is no change in the acetylation status of histone H4 in these animals during mammary gland involution. These data show that the co-ordinated up-regulation of c/ebpδ and SMCT1 in the mammary gland during involution is associated with HDAC inhibition. Earlier studies have shown that c/ebpδ expression in the mammary gland is critical for the expression of pro-apoptotic genes (p53, BAK, IGFBP5, and SGP2/clusterin), for the repression of anti-apoptotic genes (BFL1 and cyclin D1), and for the induction of cell death associated with involution of the gland (Thangaraju, M. et al. *Development* 132, in press (2005)). The present studies indicate that SMCT1 may play a critical role in mediating the biologic effects of c/ebpδ in the mammary gland through HDAC inhibition.

Figure 21A:
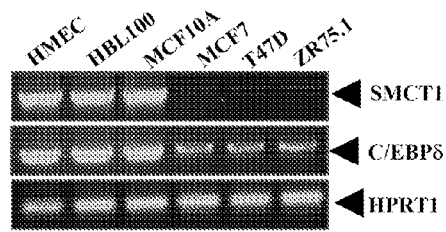
FIG. 21A shows RT-PCR analysis of SMCT1 mRNA and C/EBPδ mRNA in human normal mammary epithelial cell lines (HMEC, HBL100 and MCF10A) and human breast cancer cell lines (MCF7, T47D and ZR75.1).
Figure 21B:
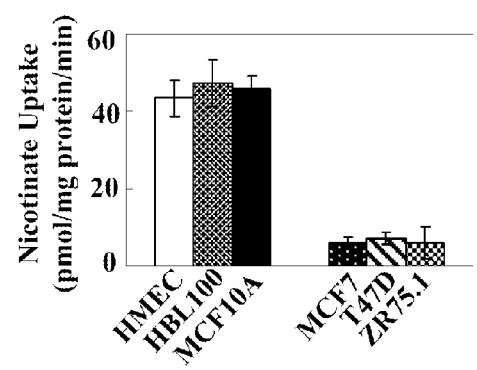
FIG. 21B shows functional activity of SMCT1 in human normal mammary epithelial cell lines and human breast cancer cell lines. Activity was monitored by measuring the ability of the cells to take up nicotinate (20 µM) in a Na$^+$-dependent manner.
Figure 21C:
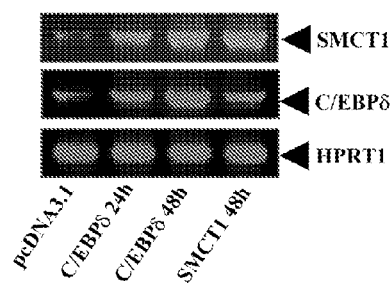
FIG. 21C illustrates induction of SMCT1 expression by C/EBPδ and vice versa in MCF7 cells. Cells were transiently transfected with pcDNA3.1, C/EBPδ cDNA, or SMCT1 cDNA. 24 h or 48 h following transfection, expression of SMCT1 and C/EBPδ was analyzed by RT-PCR.
Figure 21D:
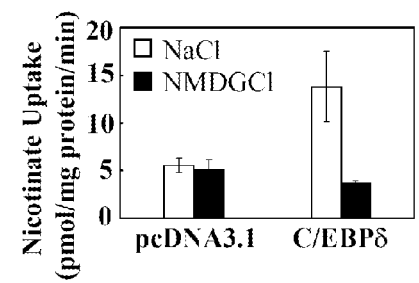
FIG. 21D shows confirmation of SMCT1 induction by C/EBPδ using Na$^+$-dependent uptake of nicotinate as a read-out of the transporter function.
Figure 22A:
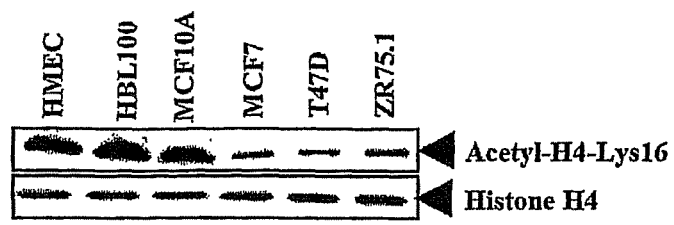
FIG. 22A shows acetylation status of histone H4 in human normal mammary epithelial cell lines (HMEC, HBL100 and MCF10A) and human breast cancer cell lines (MCF7, T47D and ZR75.1). Protein extracts from these cells were subjected to western blot analysis using antibodies against histone H4 and acetylated histone H4 (Lys 16).
Figure 22B:
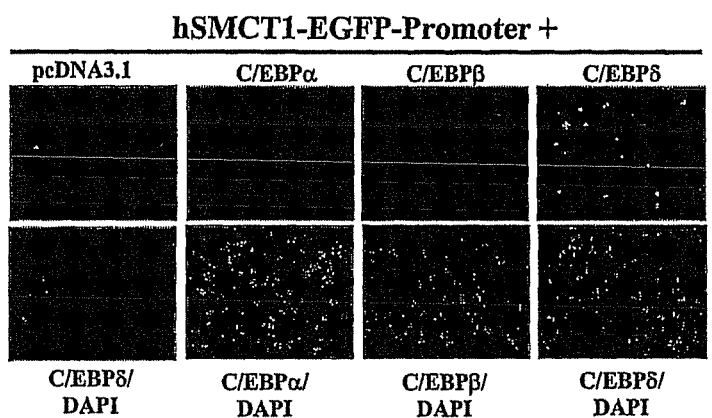
FIGS. 22B and 22C show transactivation of human SMCT1 promoter specifically by C/EBPδ. Human SMCT1 promoter, 2.4 kb upstream of transcriptional start site, was cloned into pUII-EGFP vector construct. The promoter construct was transiently transfected into MCF7 cells along with pcDNA3.1, C/EBPα cDNA, C/EBPβ cDNA, or C/EBPβ cDNA. At 48 h following transfection, cells were visualized under fluorescence microscope for GFP expression. DAPI was used as a nuclear stain. The expression of C/EBP isoforms (α, β, and δ) was monitored by immunofluorescence (red) with isoform-specific antibodies. Primary antibody was omitted to serve as the negative control (first row, bottom panel). The transactivation was also studied using luciferase as a reporter. Human SMCT1 promoter was cloned into pUBT-Luc vector and transiently transfected into MCF7 cells along with pcDNA3.1, C/EBPα cDNA, C/EBPβ cDNA, or C/EBPδ cDNA. At 24 h following transfection, cells, were lysed and used for luciferase assay (Promega luciferase assay kit). Luciferase activity was normalized with protein and results are given as means±SE for three independent experiments.
Figure 22C:
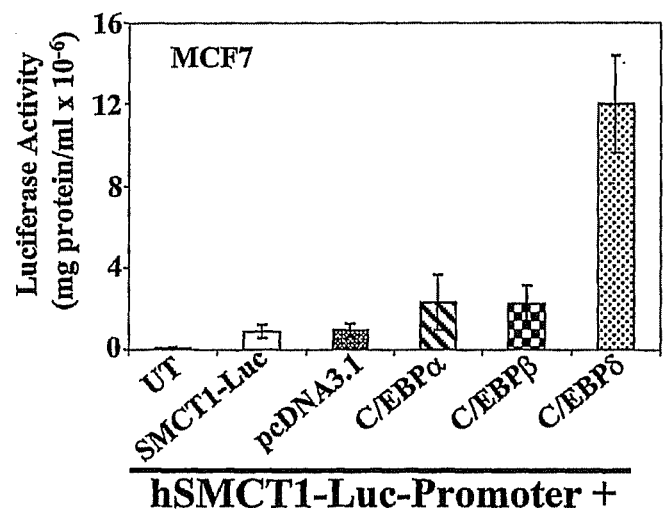
Figure 27:
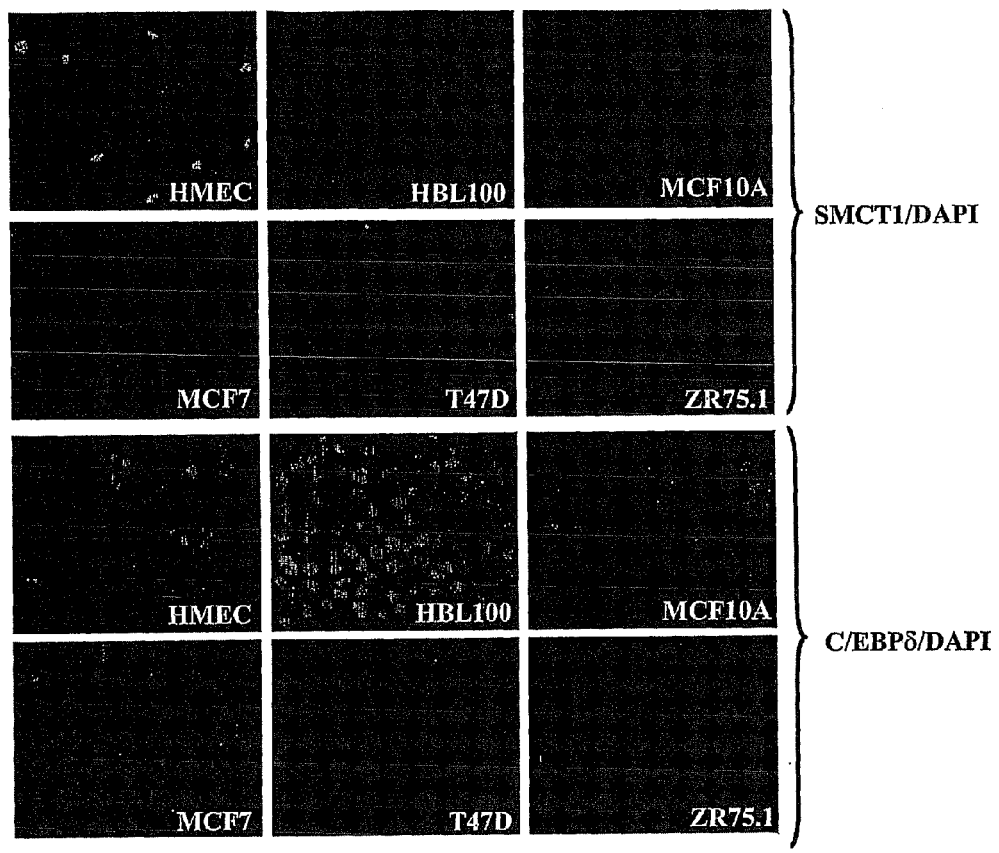
FIG. 27 shows immunofluorescence analysis of the expression of SMCT1 and C/EBPδ in non-transformed (HMEC, HBL100, and MCF10A) and transformed (MCF7, T47D, and ZR75.1) breast epithelial cell lines. DAPI was used as a nuclear stain (blue).
Figure 28:
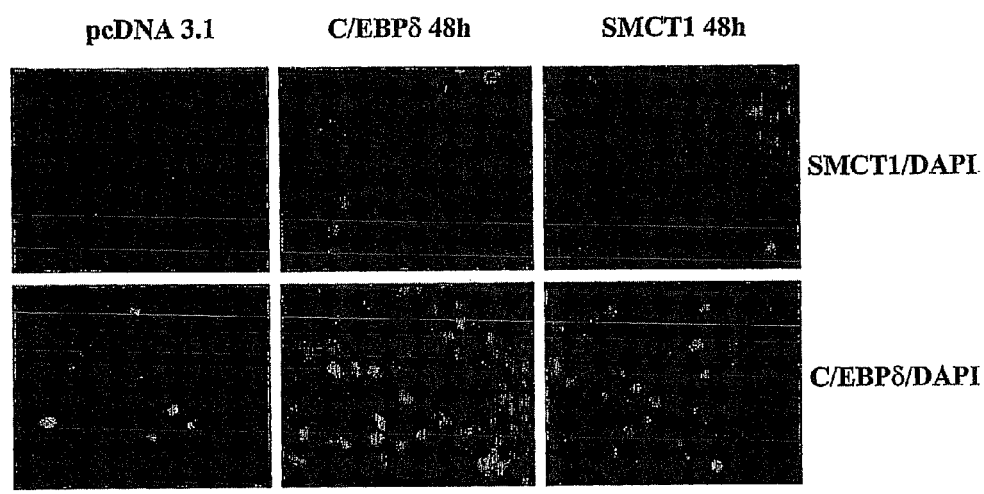
FIG. 28 shows evidence for the induction of SMCT1 by C/EBPδ and for the induction of C/EBPδ by SMCT1 in MCF7 cells. The proteins were detected by immunofluorescence using specific antibodies. DAPI was used as a nuclear stain (blue).

It was then examined whether the functional relationship between C/EBPδ and SMCT1 and its role in inducing HDAC inhibition have any relevance to the postulated tumor suppressive role of the transporter. To address this issue, the expression of C/EBPδ and SMCT1 between normal, non-transformed, mammary epithelial cell lines (HMEC, HBL100, and MCF10A) and transformed breast cancer cell lines (MCF7, T47D, and ZR75.1) (FIGS. 21A and 21B) were compared. Both genes are expressed in normal epithelial cell lines and their expression is decreased markedly in transformed cell lines. With SMCT1, this is evident at the mRNA level (FIG. 21A), protein level (FIG. 27), and functional level (FIG. 21B). With C/EBPδ, this is evident at the mRNA level (FIG. 21A) and protein level (FIG. 27). In MCF7 cells, which express very low levels of C/EBPδ and SMCT1, transient expression of C/EBPδ induces SMCT1 expression (FIGS. 21C, 21D and 28). Quite unexpectedly, exogenous expression of SMCT1 in these cells stimulates C/EBPδ expression (FIGS. 21C and 28). Since SMCT1 expression during mammary gland involution correlates with HDAC inhibition, it was examined whether such a correlation would also be apparent in mammary epithelial cell lines. Here we show that the normal epithelial cell lines, which express SMCT1 abundantly, show enhanced acetylation at Lys16 of histone H4; in contrast, the transformed cancer cell lines, which express little or no SMCT1, exhibit markedly reduced acetylation of histone H4 (FIG. 22A). It was then investigated whether the SLC5A8 gene is regulated by C/EBPδ, by evaluating the influence of C/EBPδ on human SLC5A8 promoter. With both GFP and luciferase as the reporters, the induction of SLC5A8 promoter activity by C/EBPδ is readily demonstrable (FIGS. 22B and 22C). This activity is specific for the C/EBPδ isoform as no detectable effects are seen with C/EBPα and C/EBPβ.

Figure 23A:
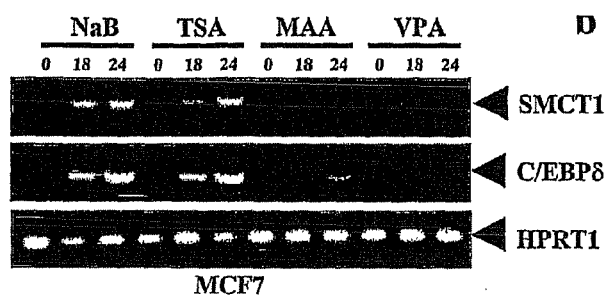
FIG. 23A shows induction of SMCT1 and C/EBPδ expression by HDAC inhibitors in MCF7 cells. Cells were treated with sodium butyrate (NaB, 5 mM), trichostatin A (TSA, 1 µM), methoxyacetic acid (MAA, 5 mM), and valproic acid (VPA, 2 mM) for 18 or 24 h and the levels of SMCT1 mRNA and C/EBPδ mRNA were monitored by RT-PCR.
Figure 29:
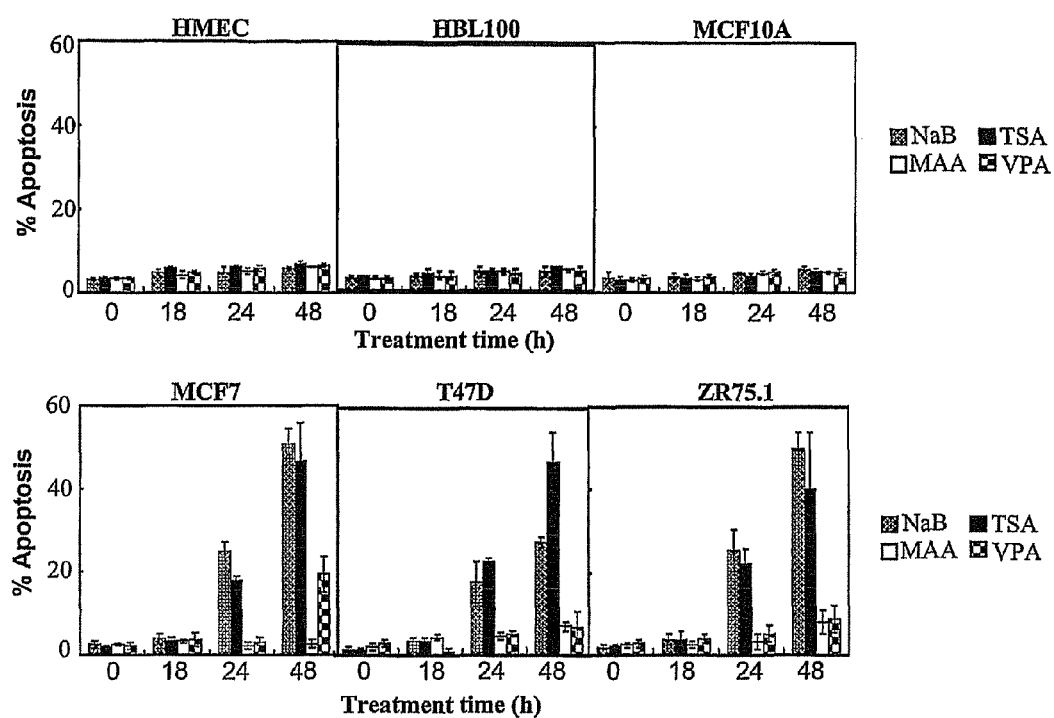
FIG. 29 illustrates the influence of HDAC inhibitors (NaB, sodium butyrate; TSA, trichostatin A; MAA, methoxyacetic acid; VPA, valproic acid) on apoptosis in non-transformed (HMEC, HBL100, and MCF10A) and transformed (MCF7, T47D, and ZR75.1) breast epithelial cell lines.
Figure 30:
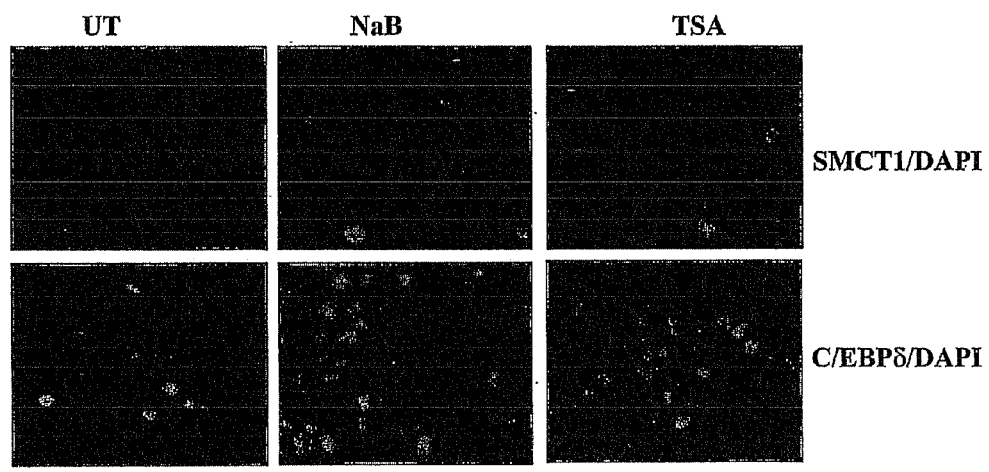
FIG. 30 shows induction of SMCT1 and C/EBPδ by sodium butyrate (NaB) and trichostatin A (TSA) in MCF7 cells as assessed by immunofluorescence using specific antibodies. DAPI was used as a nuclear stain.
Figure 31:
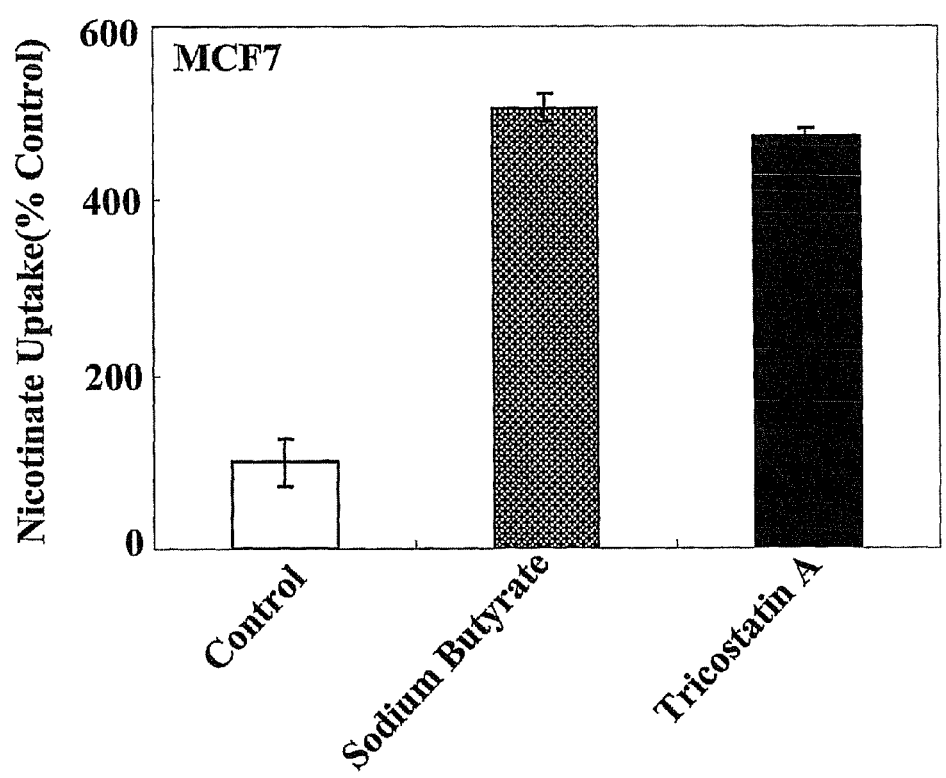
FIG. 31 illustrates functional evidence for the induction of SMCT1 in MCF7 cells by HDAC inhibitors as assessed by $NA^+$-dependent uptake of nicotinate.

HDAC inhibitors are known to induce apoptosis specifically in tumor cells (Nakata, S. et al. (2004) *Oncogene* 23:6261-6271; Insinga, A. et al. (2005) *Nat. Med.* 11:71-76; Nebbioso, A. et al. (2005) *Nat. Med.* 11:77-84). The direct relationship between the expression of SMCT1 and the histone acetylation status in mammary epithelial cell lines led to the examination of whether there is a differential influence of HDAC inhibitors on tumor cells in inducing apoptosis. These studies have shown that, in spite of abundant expression of SMCT1 in normal mammary epithelial cells, exposure of these cells to the HDAC inhibitors butyrate or trichostatin A does not induce apoptosis, but does so in breast tumor cell lines (FIG. 29). The HDAC inhibitors methoxyacetate and valproate do not have any effect on apoptosis in these cells. Thus, butyrate and trichostatin A cause apoptosis specifically in tumor cell lines. It was then investigated whether these HDAC inhibitors influence the expression of SMCT1 and C/EBPδ in MCF7 cells, a breast tumor cell line (FIGS. 23A and 30). Butyrate and trichostatin A were found to induce the expression of both genes. However, the HDAC inhibitors methoxyacetate and valproate show no or little activity in terms of the expression of these two genes. The increase in the expression of SMCT1 in response to butyrate and trichostatin A is demonstrable also at the functional level (FIG. 31). Thus, only those HDAC inhibitors which are capable of inducing SMCT1 expression, cause apoptosis in MCF7 cells.

Figure 23B:
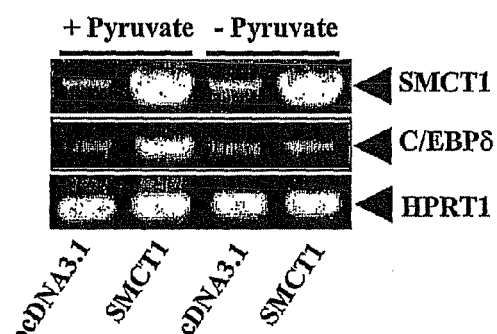
FIG. 23B shows the requirement of pyruvate in the culture medium for SMCT1-dependent induction of C/EBPδ expression in MCF7 cells.
Figure 23C:
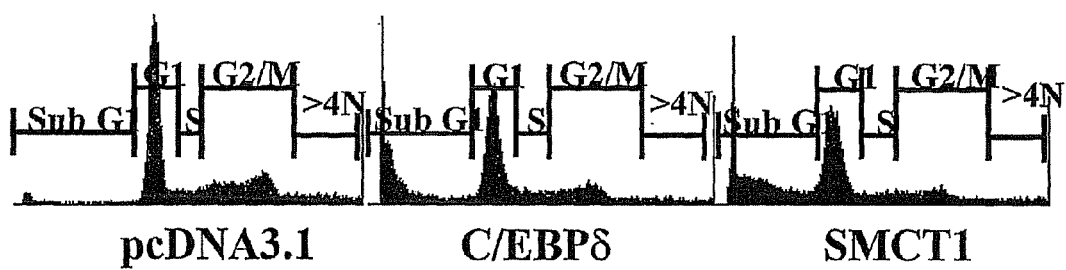
FIG. 23C shows induction of apoptosis by transient expression of C/EBPδ and SMCT1 in MCF-7 cells. Cells were transiently transfected with pcDNA3.1, C/EBPδ cDNA, or SMCT1 cDNA. 48 h following transfection, cells were collected and faced with 50% ethanol and stained with propidium iodide. Apoptotic cells (sub-G1 populations) were analyzed by FACS.
Figure 24A:
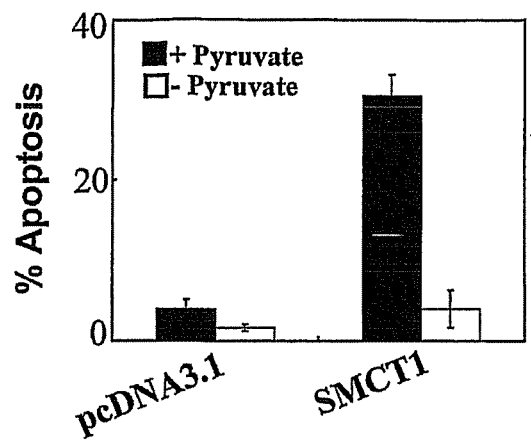
FIG. 24A illustrates the requirement of pyruvate in the culture medium for SMCT1-dependent apoptosis in MCF7 cells.
Figure 24B:
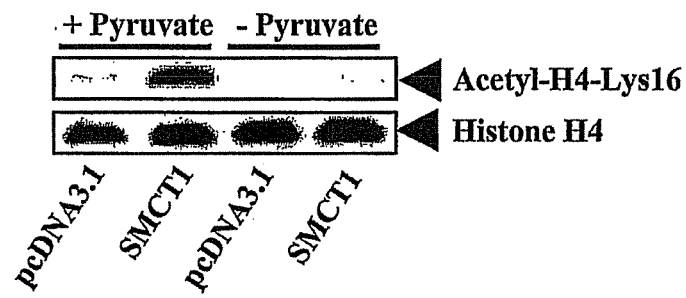
FIG. 24B shows the association of SMCT1 expression with HDAC inhibition in intact MCF7 cells is dependent on the presence of pyruvate in the culture medium. MCF7 cell lysate was immunoprecipitated with an antibody specific for histone H4 and the immunoprecipitate was probed with an antibody specific for acetylated histone H4 (Lys16) on western blot.
Figure 24C:
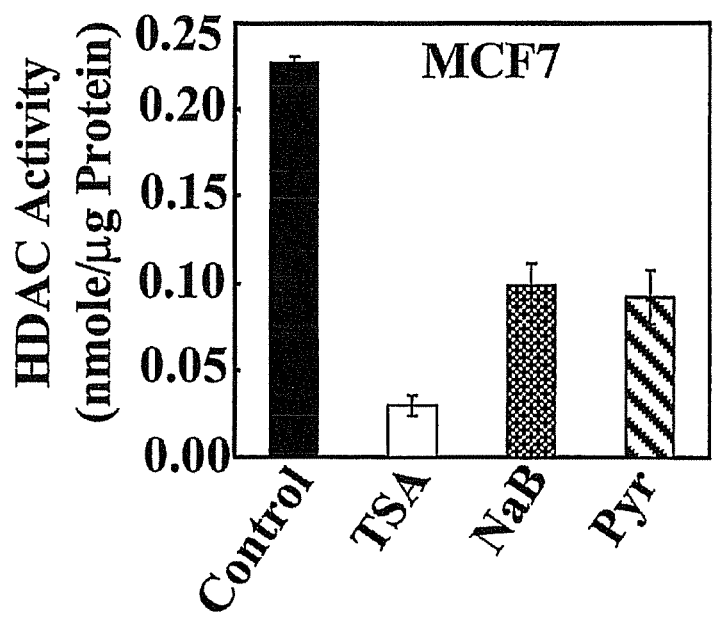
FIG. 24C illustrates inhibition of HDAC by pyruvate (Pyr) in a cell-free assay system using MCF7 cell lysate as a source of HDAC. Trichostatin A (TSA) and sodium butyrate (NaB) were used as positive controls.

The induction of SMCT1 by C/EBPδ in MCF7 cells is easily understandable because of the enhanced activity of the SLC5A8 promoter by the transcription factor (FIGS. 21C, 22B and 22C). But, the induction of C/EBPδ by SMCT1 was quite unexpected. The findings that HDAC inhibitors such as butyrate can induce C/EBPδ expression in MCF7 cells suggest that the expression of SMCT1 in these cells may facilitate the entry of a hitherto unknown HDAC inhibitor from the cell culture medium into the cells. Butyrate, a known substrate for SMCT1, is not present in the cell culture medium. However, MCF7 cells are usually cultured in the presence of pyruvate, a known substrate for SMCT1. Therefore, it was hypothesized that pyruvate may function as an inhibitor of HDAC. To test this hypothesis, the effects of exogenous expression of SMCT1 on C/EBPδ expression in MCF7 cells in the presence and absence of pyruvate were compared (FIG. 23B). SMCT1 induces C/EBPδ expression only in the presence of pyruvate. The exogenous expression of C/EBPδ and SMCT1 in these cells induces apoptosis (FIG. 23G), and this phenomenon is dependent on the presence of pyruvate (FIG. 24A). To determine if pyruvate is a HDAC inhibitor, the level of acetylation at Lys16 in histone H4 in MCF7 cells in the presence and absence of pyruvate following exogenous expression of SMCT1 were analyzed (FIG. 24B). The acetylation status of histone H4 is low in these cells irrespective of the presence or absence of pyruvate when transfected with vector alone. Expression of SMCT1 enhances the acetylation status in these cells but only when pyruvate is present. This suggests that the expression of SMCT1 facilitates the entry of pyruvate into cells and causes HDAC inhibition and apoptosis. The ability of pyruvate to inhibit HDAC is demonstrable in a cell-free system (FIG. 24C).

Figure 25A:
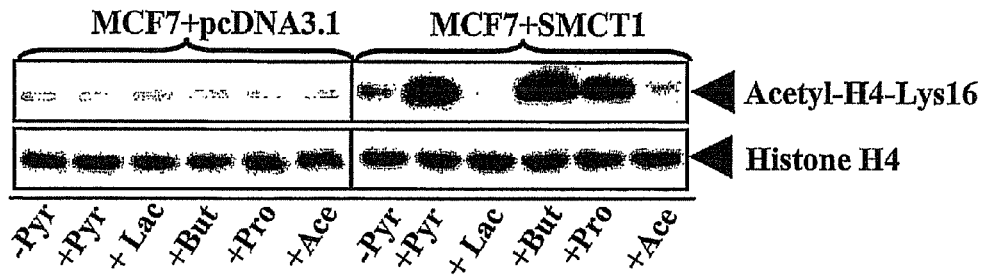
FIG. 25A shows acetylation status of histone H4 in vector-transfected and SMCT1 cDNA-transfected MCF7 cells when cultured in the absence or presence of pyruvate, lactate, butyrate, propionate, and acetate (1 mM). Protein extracts from these cells were subjected to western blot analysis using antibodies against histone H4 and acetylated histone H4 (Lys16).
Figure 25B:
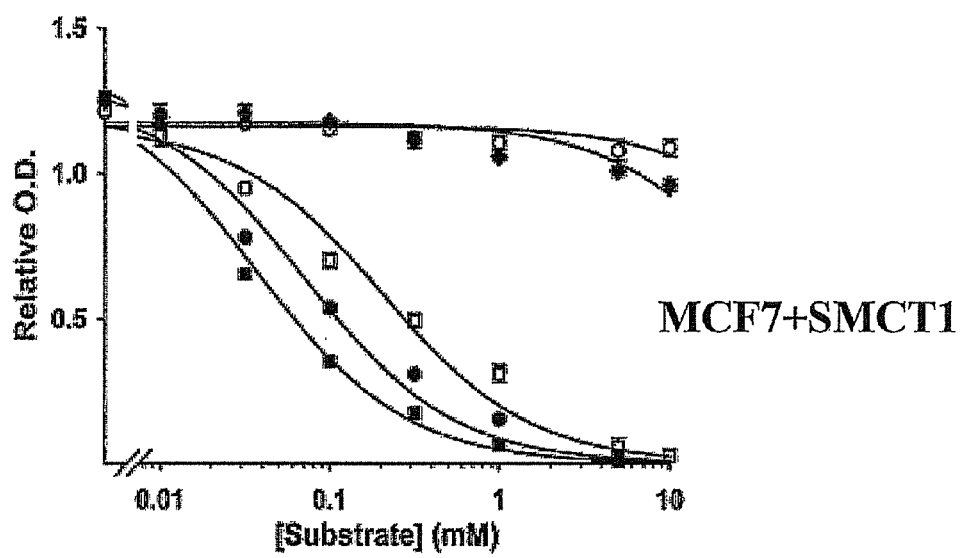
FIG. 25B shows a dose-response relationship for the effects of butyrate (■), pyruvate (●), propionate (□), lactate (♦), and acetate (○) on colony formation in MCF7 cells transfected with SMCT1 cDNA.
Figure 25C:
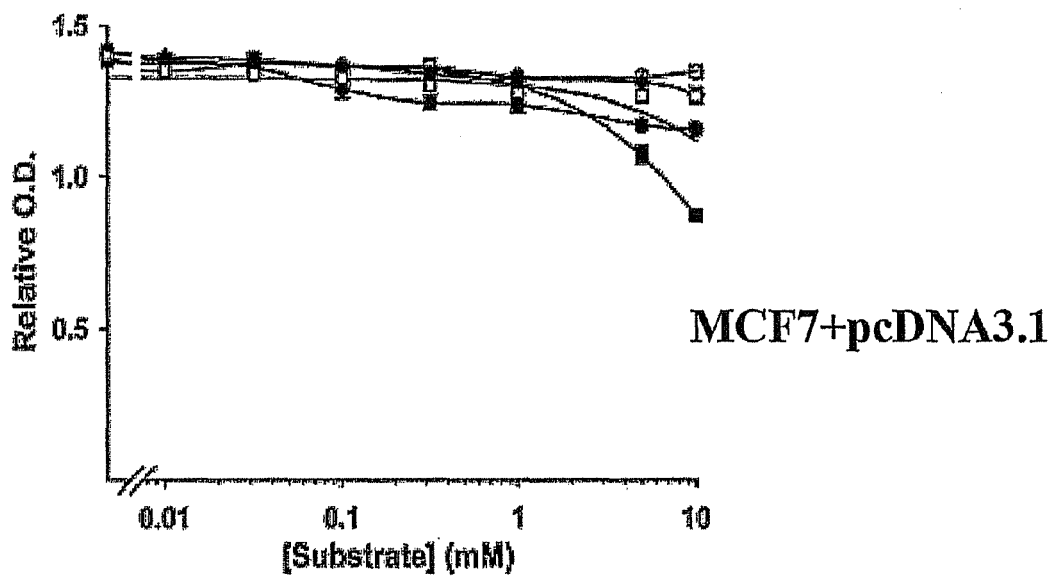
FIG. 25C shows a dose-response relationship for the effects of butyrate (■), pyruvate (●), propionate (□), lactate (♦), and acetate (○) on colony formation in MCF7 cells transfected with pcDNA.
Figure 25D:
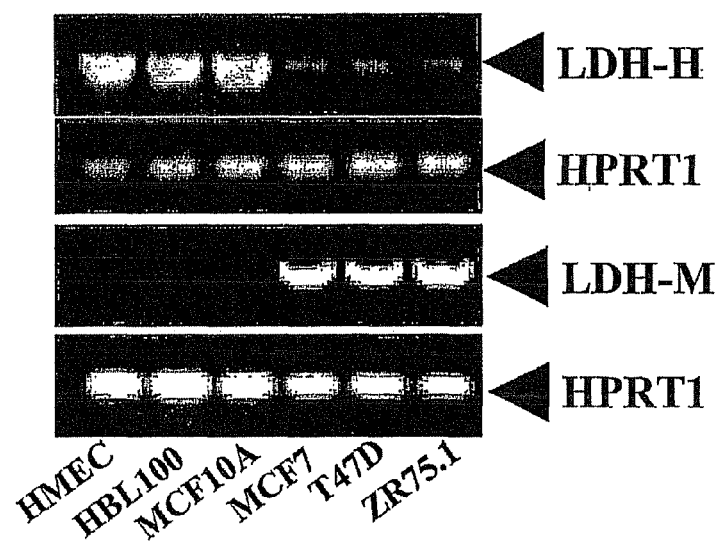
FIG. 25D is a semi-quantitative RT-PCR analysis of steady-state mRNA levels for lactate dehydrogenase subunits LDH-H and LDH-M in non-transformed (HMEC, HBL100, and MCF10A) and transformed (MCF7, T47D, and ZR75.1) breast epithelial cell lines.
Figure 32:
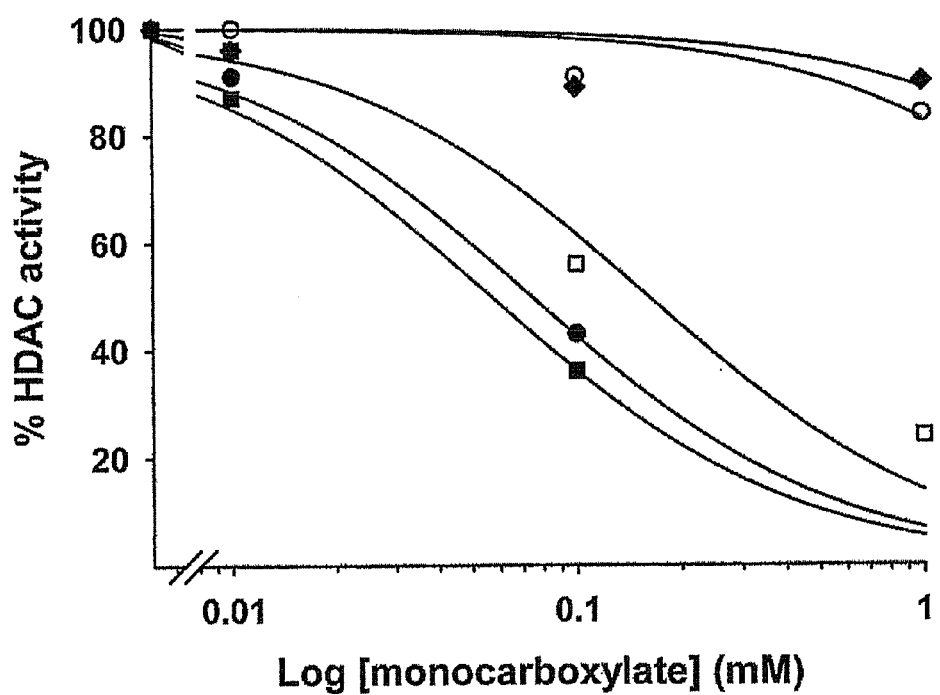
FIG. 32 shows a dose-response relationship for the inhibition of HDAC by butyrate (■), pyruvate (●), propionate (□), lactate (○), and acetate (♦) in a cell-free assay system.
Figure 33:
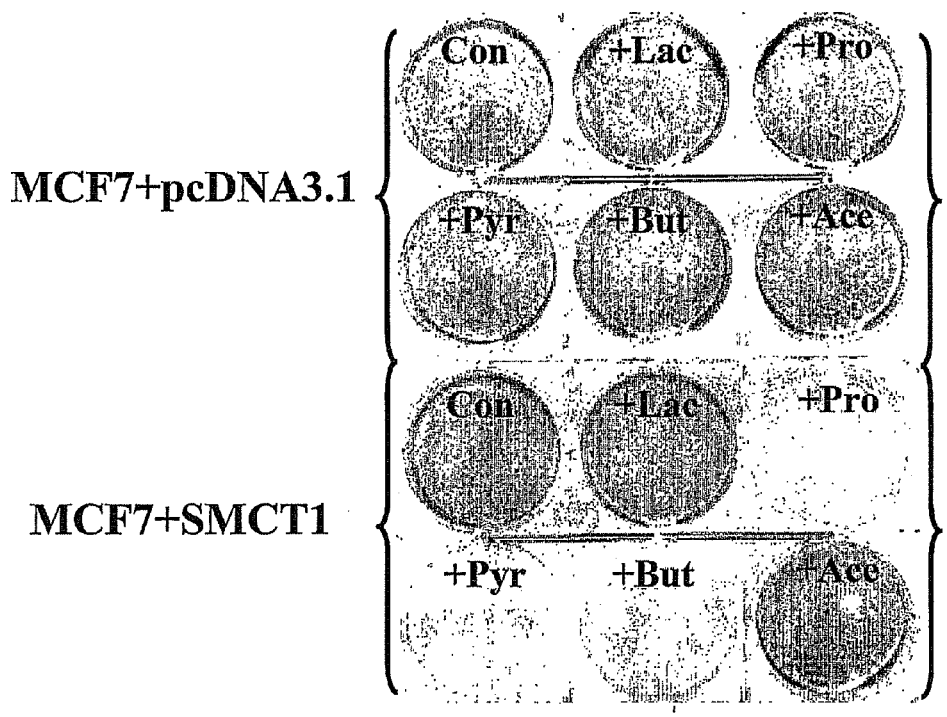
FIG. 33 shows effects of lactate (Lac), proprionate (Pro), pyruvate (Pyr), butyrate (But), and actetate (Ace) on colony formation in MCF7 cells transfected either with vector alone (pcDNA3.1) or with SMCT1 cDNA.

The findings that pyruvate is an endogenous HDAC inhibitor and a tumor suppressor have important implications in cancer biology. It is well known that tumor cells up-regulate glycolysis and convert the glycolytic end product pyruvate effectively into lactate (Stubbs, M., McSheehy, P. M. J., Griffiths, J. R. & Bashford, C. L. (2000) *Mol. Med. Today* 6:15-19). Therefore, the potencies of pyruvate and lactate to inhibit HDAC in a cell-free system were compared (FIG. 32). While pyruvate inhibits HDAC activity ($IC_{50}$, ~80 μM), lactate does not. The potencies of acetate, propionate, and butyrate as HDAC inhibitors were also compared (FIG. 32). These studies show that butyrate is the most potent HDAC inhibitor ($IC_{50}$, ~60 μM) whereas acetate is the least potent. The potencies of pyruvate, lactate, and the three short-chain fatty acids to function as HDAC inhibitors in the cell-free system correlate with their abilities to inhibit HDAC in SMCT1-expressing MCF7 cells as evident from the changes in the acetylation status of histone H4 (FIG. 25A). In vector-transfected cells, none of these monocarboxylates has any effect on the histone H4 acetylation status. The potencies of these monocarboxylates as HDAC inhibitors with their abilities to function as tumor suppressors in MCF7 cells were then compared (FIG. 33). None of these monocarboxylates has any effect on cell growth, as determined using a colony formation assay, in MCF7 cells in the absence of SMCT1 expression; however, in SMCT1-expressing MCF7 cells, pyruvate, butyrate, and propionate, which are HDAC inhibitors, induce apoptosis whereas acetate and lactate, which possess no or lithe HDAC inhibitory activity, have no effect on cell growth. The potencies of these monocarboxylates to inhibit HDAC parallel their potencies to inhibit colony formation in SMCT1-expressing MCF7 cells (FIG. 25B). The $IC_{50}$ values for butyrate, pyruvate, and propionate in the colony formation assay are 37±5, 72±12, and 205±40 µM, respectively. Even at the highest concentration tested (10 mM), these monocarboxylates show no or little effect on vector-transfected cells under identical conditions (FIG. 25C). Since pyruvate and lactate have differential effects on apoptosis in MCF7 cells, a breast tumor cell line, the expression of the two subunits of lactate dehydrogenase (LDH-H and LDH-M) in non-transformed breast epithelial cell lines and in breast tumor cell lines were investigated. LDH1 is a homotetramer of LDH-H and its kinetic features are suitable for the conversion of lactate into pyruvate; on the other hand, LDH5 is a homotetramer of LDH-M and its kinetic features are suitable for the conversion of pyruvate into lactate. Here it is shown that the non-transformed cell lines express LDH-H more abundantly than the tumor cell lines; in contrast, LDH-M is expressed at much higher levels in tumor cell lines than in non-transformed cell lines (FIG. 25D). Thus, breast tumor cell lines have an effective mechanism to convert pyruvate into lactate and maintain intracellular concentrations of pyruvate at very low levels in spite of the tumor-associated up-regulation of glycolysis.

These studies have produced a number of new and important findings that are relevant to mammary gland involution and breast cancer. First, it has been demonstrated here a functional relationship between SMCT1 and C/EBPδ. The expressions of both genes exhibit a parallel temporal pattern during mammary gland involution. It is also shown that the expression of SLC5A8 gene coding for SMCT1 is under the control of c/ebpδ. Thus, c/ebpδ and SMCT1 are involved in mammary gland involution. Butyrate, an abundant component of breast milk and a substrate for SMCT1, is likely to be a key determinant of SMCT1-induced changes in histone acetylation and apoptosis associated with the involution process.

The findings that SMCT1 controls the expression of C/EBPδ and that the SMCT1-induced cell death is specific for, tumor cells are very important. The effects of SMCT1 are dependent on the transporter-mediated entry of HDAC inhibitors (e.g., butyrate, pyruvate, and propionate) into tumor cells. This is the first time that pyruvate is recognized as an endogenous inhibitor of HDAC. In normal mammary epithelial cells which express SMCT1, pyruvate does not induce apoptosis. In contrast, in tumor cells which do not express SMCT1, exogenous expression of the transporter induces apoptosis but only in the presence of pyruvate. Tumor cells are known to up-regulate glycolysis and accumulate lactic acid in the culture medium (Stubbs, M., McSheehy, P. M. J., Griffiths, J. R. & Bashford, C. L. (2000) *Mol. Med. Today* 6:15-19 (2000); Gatenby; R. A. & Gillies, R. J. (2004) *Nat. Rev. Cancer* 4:891-899). The enhanced conversion of pyruvate into lactate is the result of induction of the lactate dehydrogenase isoform LDH5 in tumor cells. The relationship between the enhanced conversion of pyruvate into lactic acid and tumor growth is not well understood. The present findings that pyruvate is an inhibitor of HDAC and that it induces apoptosis specifically in tumor cells provide a logical explanation for the relevance of LDH5 induction to tumor progression. Since pyruvate is a MAC inhibitor and is pro-apoptotic in cancer cells, induction of LDH5 as a means to prevent the accumulation of pyruvate inside the cells despite the up-regulation of the glycolytic process offers a mechanism for the tumor cells to evade the pyruvate-induced cell death. Pharmacologic means to increase the intracellular concentration of pyruvate inside the tumor cells may have potential in the treatment of cancer.

Methods c/ebpδ knockout mice: c/ebpδ$^{-/-}$ mice (Sterneck, E. et al. "Selectively enhanced contextual fear conditioning in mice lacking the transcriptional regulator CCAAT/enhancer binding protein delta," (1998) *Proc. Natl. Acad. Sci. USA* 95:10908-10913), backcrossed for at least 11 generations into C57BL/6, were intercrossed to generate wild type and homozygous mice. Female mice were mated at approximately 7 weeks of age, and males were removed post-coitum. Litters were standardized to six pups at birth and these pups were removed on day 7 of lactation (Thangaraju, M., Sharan, S. & Sterneck, E. (2004) *Oncogene* 23, 2548-2553). Females were euthanized by $CO_2$ at different time periods following the induction of mammary gland involution as indicated, and the #4 mammary glands removed for analysis. All animals were housed and handled according to approved protocols established by the NCI Animal Care and Use Committee and NIH guidelines. Details for the tissue preparation for the immunohistochemistry and extraction of RNA and protein from mammary glands have been described previously (Thangaraju, M. et al., *Development* 132, in press (2005)).

RT-PCR: Two µg of RNA was reverse transcribed using the Gene Amp PCR system (Roche) according to the manufacturer's instructions. Amplification of cDNA corresponding to mouse SMCT1 [5'-GAT ATA TAG CCA TGG ACG CGT CGC GG-3' (sense) (SEQ ID NO:9), 5'-AAG CTT CAC AAG CGA GTC CCA TTG AT-3' (anti-sense) (SEQ ID NO: 10)], mouse c/ebpδ [5'-GAC GCC GCC ATG AGC GCC GCT CTT TT-3' (sense) (SEQ ID NO:11), 5'-AAG CTT TTA CCG GCA GTC GOC GCC GC-3' (anti-sense) (SEQ ID NO:12)], human SMCT1 [5'-ACG CGT ATA GCC ATG GAC ACG CCA CC-3' (sense) (SEQ ID NO:13), 5'-CAG CTG TCA CAA ACG AGT CCC ATT GC-3' (anti-sense) (SEQ ID NO:14)], and human C/EBPδ [5'-GAC GCC GCC ATG AGC GCC GCTG CTC TT-3' (sense) (SEQ ID NO:15), 5'-AAG CTT TTA CCG GCA GTC TGT CC-3' (anti-sense) (SEQ ID NO:16)] was carried out using HPRT1 (hypoxanthine guanine phosphoribosyl transferase 1) as an internal control.

Protein analysis: For Western blot analysis, 50 µg of protein was fractionated on SDS-PAGE gels and transferred to Protran nitrocellulose membrane (Schleicher & Schull). Membranes were blocked with bovine serum albumin and then exposed to primary antibody [anti-histone H4 (Upstate USA, Inc.) or anti-acetylated histone H4 (Lys16) (Santa Cruz)] at 4° C. overnight followed by treatment with appropriate secondary antibody, conjugated to horseradish peroxidase, at room temperature for 1 h. Proteins were visualized by ECL Super Signal Western System (Pierce).

Immunohistochemical analysis: Paraffin blocks were deparaffinized in xylene and rehydrated through graded alcohols. Endogenous peroxidase activity was quenched with 3% $H_2O_2$ in methanol at room temperature. Tissue sections were treated at 95° C. in Vector antigen-unmasking solution for antigen retrieval. Normal goat serum (5%) was applied for 30 min to block non-specific protein-binding sites. Primary rabbit anti-SMCT1, raised against the peptide ELNFTDHSGK-INGTRL corresponding to the last 16 amino acids in the carboxy tail of mouse SMCT1, and goat anti-acetylated histone H4 (Lys16) antibodies were applied for 2 h, followed by biotinylated panspecific secondary antibody for 10 min. Immunodetection was accomplished with the Dako Envision System, followed by chromogen detection with diaminobenzidine. Negative controls without the primary antibodies were processed in the same manner.

Measurement of SMCT1 transport function in mammary epithelial cell lines: The transport function of SMCT1 was monitored by $Na^+$-coupled nicotinate uptake. Uptake of [$^{14}C$]-nicotinate (20 μM) was measured in the presence or absence of $Na^+$ in monolayer cell cultures. $Na^+$-dependent uptake was calculated by subtracting the uptake measured in the absence of $Na^+$ from the uptake measured in the presence of $Na^+$. A similar procedure was used to determine SMCT1 transport function in MCF7 cells, which were treated with HDAC inhibitors or transfected with different cDNA constructs.

Cell cycle analysis: Cells were fixed in 50% ethanol, treated with 0.1% sodium citrate, 1 mg/ml RNase A, and 50 μg/ml propidium iodide, and subjected to FACS (Becton Dickinson FacsCaliber) analysis. Cells with DNA content below Cl were scored as apoptotic population.

Measurement of HDAC activity in a cell-free system: This was done using a commercially available assay kit (BioVision). MCF7 cell lysate was used as a source of HDAC activity. 50 μg of lysate protein was incubated with various monocarboxylates (1 mM), or trichostatin A (20 μM), and the reaction was initiated by the addition of HDAC substrate. The reaction was then terminated and the deacetylated product was measured according to the manufacturer's instructions. The activity is expressed in nmoles of deacetylated product formed per μg of MCF7 cell lysate protein per 30 min.

Plasmid construction and reporter assays: The cDNAs for human SMCT1, C/EBPα, C/EBPβ and C/EBPδ were cloned into the pcDNA3.1 vector. The human SLC5A8 promoter-EGFP and SLC5A8 promoter-Luciferase constructs were generated by first subcloning the 2.4 kb SLC5A8 promoter (obtained by PCR using human genomic DNA as the template) into the TOPO-cloning vector and then using the HindIII/EcoRI-digested insert to clone into pUIIR3-EGFP and pLUC vectors. For the transactivation assays, MCF7 cells were seeded ($2\times10^5$ cells) in 35-mm tissue-culture dishes and allowed to grow in DMEM medium containing 10% FBS for 24 h. The effector and reporter plasmids were transfected using Fugene-6 according to the manufacturer's instructions (Roche). The EGFP expression was monitored after 36 h post-transfection under the fluorescence microscope. With the luciferase reporter, cells were collected after 36 h transfection and the lysates were used for measurement of luciferase activity. The activity was normalized for protein levels and compared with vector-transfected cells.

Colony formation assay: MCF7 cells ($2.5\times10^6$ cells/well) were seeded into 10-cm culture dishes and grown in the absence of pyruvate in DMEM medium containing 10% FBS. After 24 h, cells were transfected with pcDNA3.1 and SLC5A8 expression constructs, along with pEGFP-N1 to check the transfection efficiency, using Fugene 6 and OPTI-MEM. At 24 h post-transfection, cells were trypsinized and seeded into 6-well plates (10,000 cells/well) or 24-well plates (1,000 cells/well) and grown in DMEM medium without pyruvate. After 24 h, cells were exposed to 750 μg/ml G418 and different concentrations of pyruvate, lactate, butyrate, propionate and acetate for two weeks with change of medium every three days. After 2 weeks, cells were washed twice with 1×PBS and fixed in 100% methanol for 30 min followed by staining with KaryoMax Giemsa stain for 1 h. The unbound Giemsa dye was removed by washing the plates with water and the wells were dried overnight at room temperature. Finally, cells were lysed with cell lysis buffer (1% SDS in 0.2N NaOH) for 1 h and the optical density of the released dye was measured at 630 nm.

All references cited herein are hereby incorporated by reference in their entirety to the extent that there is no inconsistency with the disclosure of this specification. All patents and publications mentioned in the specification are indicative of the levels of skill of those skilled in the art to which the invention pertains, and are herein incorporated by reference to the same extent as if each individual publication, patent or patent application was specifically and individually indicated to be incorporated by reference. References cited herein are incorporated by reference herein in their entirety to indicate the state of the art as of their publication or filing date and it is intended that this information can be employed herein, if needed, to exclude specific embodiments that are in the prior art.

The invention has been illustrated by specific examples; however, as will be appreciated by those skilled in the art, alternative compounds, reagents, and methods may be substituted for those disclosed herein within the scope of the appended claims and their equivalents. It will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

We claim:

1. A method for treating a disease condition characterized by upregulation of transporter ATB$^{0,+}$ selected from the group consisting of colon cancer, inflammatory bowel disease, ulcerative colitis, Crohn's disease, lung cancer, cervical cancer, and cancers resulting from metastases from primary colon cancer sites in a patient, the method comprising:
   administering an effective amount of a prodrug or pharmaceutically acceptable salts of said prodrug to said patient, wherein said prodrug comprises an amino acid capable of intracellular transport by $ATB^{0,+}$ attached to a short-chain fatty acid;

wherein said amino acid capable of intracellular transport by $ATB^{0,+}$ is attached to said short-chain fatty chain acid by a hydroxyl group of the amino acid to form an ester with the amino acid, or said amino acid capable of intracellular transport by $ATB^{0,+}$ is attached said short-chain fatty chain acid by the amino group of the amino acid to form an amide with the amino acid.

2. The method of claim 1 wherein said disease condition is further characterized by downregulation of SLC5A8.

3. The method of claim 1 wherein said prodrug is administered in a pharmaceutically acceptable carrier selected from the group consisting of an oral delivery carrier, a suppository delivery carrier, an intravenous delivery carrier, and an aerosol carrier.

4. The method of claim 1 comprising administering said prodrug in a pharmaceutically acceptable carrier.

5. The method of claim 1, wherein said short-chain fatty acid is selected from the group consisting of butyrate, pyruvate, acetate, and propionate.

6. The method of claim 1, wherein said prodrug comprises serine butyrate, serine pyruvate, serine acetate, or serine propionate.

7. The method of claim 1, wherein said prodrug comprises serine butyrate.

8. The method of claim 1, wherein said short-chain fatty acid thereof comprises 3-bromopyruvate.

9. The method of claim 1, wherein said amino acid is selected from the group consisting neutral and cationic L- and D-amino acids.

10. The method of claim 1, wherein said amino acid is selected from the group consisting of the L-enantiomers of alanine, serine, methionine, leucine, tryptophan, threonine, histidine, phenylalanine, glutamine, asparagine, lysine, arginine, valine and isoleucine and the D-enantiomers of alanine, serine, methionine, leucine, and tryptophan.

11. The method of claim 1, wherein said amino acid is selected from the group consisting of the L-enantiomers of serine, threonine and tyrosine.

12. The method of claim 1 wherein said amino acid is a modified amino acid modified to comprise a hydroxyl group, and said short-chain fatty acid is attached to said modified amino acid through said hydroxyl group to foam a fatty acid ester of said modified amino acid.

13. A method for treating cancer characterized by upregulation of transporter $ATB^{0,+}$ by targeting a short-chain fatty acid to cancer cells in a patient, the method comprising:

administering an effective amount of a prodrug or pharmaceutically acceptable salts of said prodrug to said patient;

wherein said prodrug comprises an amino acid capable of intracellular transport by $ATB^{0,+}$ attached to a short-chain fatty acid;

wherein said amino acid capable of intracellular transport by $ATB^{0,+}$ is attached to said short-chain fatty chain acid by a hydroxyl group of the amino acid to form an ester with the amino acid, or said amino acid capable of intracellular transport by $ATB^{0,+}$ is attached said short-chain fatty chain acid by the amino group of the amino acid to form an amide with the amino acid.

14. The method of claim 13, wherein said cancer is further characterized by downregulation of SLC5A8.

15. The method of claim 13, wherein said short-chain fatty acid is selected from the group consisting of butyrate, pyruvate, acetate, and propionate.

16. The method of claim 13, wherein said amino acid is selected from the group consisting of the L-enantiomers of alanine, serine, methionine, leucine, tryptophan, threonine, histidine, phenylalanine, glutamine, asparagine, lysine, arginine, valine and isoleucine and the D-enantiomers of alanine, serine, methionine, leucine, and tryptophan.

17. The method of claim 13 comprising administering said prodrug in a pharmaceutically acceptable carrier.

18. The method of claim 13 wherein said prodrug is administered in a pharmaceutically acceptable carrier selected from the group consisting of an oral delivery carrier, a suppository delivery carrier, an intravenous delivery carrier, and an aerosol carrier.

19. The method of claim 13, wherein said prodrug comprises serine butyrate, serine pyruvate, serine acetate, or serine propionate.

20. The method of claim 13, wherein said prodrug comprises serine butyrate.

21. The method of claim 13, wherein said short-chain fatty acid thereof comprises 3-bromopyruvate.

22. The method of claim 13, wherein said amino acid is selected from the group consisting neutral and cationic L- and D-amino acids.

23. The method of claim 13 wherein said amino acid is a modified amino acid modified to comprise a hydroxyl group, and said short-chain fatty acid is attached to said modified amino acid through said hydroxyl group to form a fatty acid ester of said modified amino acid.

* * * * *